US007041459B2

(12) United States Patent
Singh et al.

(10) Patent No.: US 7,041,459 B2
(45) Date of Patent: May 9, 2006

(54) ANALYZING PHOSPHORYLATED PROTEINS

(75) Inventors: Sharat Singh, San Jose, CA (US); Robert Allan Zivin, Skillman, NJ (US)

(73) Assignee: Monogram Biosciences, Inc., South San Francisco, CA (US)

( * ) Notice: Subject to any disclaimer, the term of this patent is extended or adjusted under 35 U.S.C. 154(b) by 452 days.

(21) Appl. No.: 10/153,312

(22) Filed: May 21, 2002

(65) Prior Publication Data

US 2003/0040016 A1    Feb. 27, 2003

Related U.S. Application Data

(60) Provisional application No. 60/334,902, filed on Oct. 24, 2001, provisional application No. 60/292,548, filed on May 21, 2001.

(51) Int. Cl.
*G01N 33/53* (2006.01)
(52) U.S. Cl. .................... 435/7.1; 435/6; 435/7.72; 435/7.95; 435/21; 436/436; 436/161; 436/808
(58) Field of Classification Search ................. 435/6, 435/7.1, 7.72, 55, 56; 436/161, 808
See application file for complete search history.

(56) References Cited

U.S. PATENT DOCUMENTS

| | | | |
|---|---|---|---|
| 4,274,240 A | 6/1981 | Soum | 52/583 |
| 4,331,590 A | 5/1982 | Bocuslaski | 260/112 B |
| 4,444,879 A | 4/1984 | Foster et al. | |
| 4,650,750 A | 3/1987 | Giese | 435/7 |
| 4,675,300 A | 6/1987 | Zare | 436/172 |
| 4,709,016 A | 11/1987 | Giese | 530/389 |
| 4,780,421 A | 10/1988 | Kameda | 436/518 |
| 5,057,412 A | 10/1991 | Rabin | 435/6 |

(Continued)

FOREIGN PATENT DOCUMENTS

EP    0 484 027 A1    5/1992

(Continued)

OTHER PUBLICATIONS

Posewitz et al, Immobilized Gallium(III) Affinity Chromatography of Phosphopeptides, 1999, Analytical Chemistry, vol. 71, pp. 2883-2892.*

(Continued)

*Primary Examiner*—Long V. Le
*Assistant Examiner*—Deborah A. Davis
(74) *Attorney, Agent, or Firm*—Jones Day

(57) ABSTRACT

Methods, compositions and kits are disclosed for determining one or more target polypeptides in a sample where the target polypeptides have undergone phosphorylation. A mixture comprising the sample and a first reagent comprising a cleavage-inducing moiety and an IMAC resin for a binding site on a target polypeptide is subjected to conditions under which binding of respective binding moieties occurs. The binding site is the result of phosphorylation activity involving the target polypeptide. The method may be employed to determine the target polypeptide itself. In another embodiment the presence and/or amount of the target polypeptide is related to the presence and/or amount and/or activity of an agent such as an enzyme involved in phosphorylation of the target polypeptide. The interaction between the IMAC resin and the binding site brings the cleavage-inducing moiety into close proximity to a cleavable moiety, which is associated with the polypeptide and is susceptible to cleavage only when in proximity to the cleavage-inducing moiety. In this way, an electrophoretic tag for each of the polypeptides may be released. Released electrophoretic tags are separated and the presence and/or amount of the target polypeptides are determined based on the corresponding electrophoretic tags.

22 Claims, 35 Drawing Sheets

U.S. PATENT DOCUMENTS

| | | | |
|---|---|---|---|
| 5,137,609 A | 8/1992 | Manian | |
| 5,254,469 A | 10/1993 | Warren, III | 435/188 |
| 5,324,401 A | 6/1994 | Yeung | 204/180.1 |
| 5,340,716 A | 8/1994 | Ullman | 435/6 |
| 5,360,819 A | 11/1994 | Giese | 514/538 |
| 5,470,705 A | 11/1995 | Grossman | 435/6 |
| 5,494,793 A | 2/1996 | Schindele | 435/6 |
| 5,514,543 A | 5/1996 | Grossman | 435/6 |
| 5,516,636 A | 5/1996 | McCapra | 435/6 |
| 5,516,931 A | 5/1996 | Giese | 560/59 |
| 5,536,834 A | 7/1996 | Singh | 544/98 |
| 5,560,811 A | 10/1996 | Briggs | 204/451 |
| 5,565,324 A | 10/1996 | Still | 435/6 |
| 5,567,292 A | 10/1996 | Madabhushi | 204/451 |
| 5,571,680 A | 11/1996 | Chen | |
| 5,573,906 A | 11/1996 | Bannwarth | 435/6 |
| 5,573,921 A | 11/1996 | Behnke et al. | |
| 5,578,498 A | 11/1996 | Singh | 436/518 |
| 5,580,732 A | 12/1996 | Grossman | 435/6 |
| 5,602,273 A | 2/1997 | Giese | 560/60 |
| 5,604,104 A | 2/1997 | Giese | 435/7.1 |
| 5,610,020 A | 3/1997 | Giese | 435/7.1 |
| 5,616,719 A | 4/1997 | Davalian | 546/334 |
| 5,624,800 A | 4/1997 | Grossman | 435/6 |
| 5,650,270 A | 7/1997 | Giese | 435/6 |
| 5,691,151 A | 11/1997 | Braun | 435/7.2 |
| 5,703,222 A | 12/1997 | Grossman | 536/24.3 |
| 5,705,622 A | 1/1998 | McCapra | 536/23.1 |
| 5,709,994 A | 1/1998 | Pease | 435/4 |
| 5,719,028 A | 2/1998 | Dahlberg | 435/6 |
| 5,721,099 A | 2/1998 | Still | 435/6 |
| 5,723,591 A | 3/1998 | Livak | 536/22.1 |
| 5,756,726 A | 5/1998 | Hemmi | 540/474 |
| 5,763,602 A | 6/1998 | Li | 540/128 |
| 5,766,481 A | 6/1998 | Zambias | 210/656 |
| 5,777,096 A | 7/1998 | Grossman | 536/24.3 |
| 5,789,172 A | 8/1998 | Still | 435/6 |
| 5,807,675 A | 9/1998 | Davalian | 435/6 |
| 5,807,682 A | 9/1998 | Grossman | 435/6 |
| 5,811,239 A | 9/1998 | Frayne | 435/6 |
| 5,843,655 A | 12/1998 | McGall | 435/6 |
| 5,843,666 A | 12/1998 | Akhavan-Tafti | 435/6 |
| 5,843,680 A | 12/1998 | Manian | |
| 5,846,839 A | 12/1998 | Gallop | 436/518 |
| 5,849,878 A | 12/1998 | Cantor | 530/391.9 |
| 5,851,770 A | 12/1998 | Babon | 435/6 |
| 5,874,213 A | 2/1999 | Cummins | 435/6 |
| 5,876,930 A | 3/1999 | Livak | 435/6 |
| 5,916,426 A | 6/1999 | Madabhushi | 204/451 |
| 5,952,654 A | 9/1999 | Giese | 250/288 |
| 5,958,202 A | 9/1999 | Regnier | 204/451 |
| 5,986,076 A | 11/1999 | Rothschild | 536/22.1 |
| 5,989,871 A | 11/1999 | Grossman | 435/91.1 |
| 5,998,140 A | 12/1999 | Dervan | 435/6 |
| 6,001,567 A | 12/1999 | Brow | 435/6 |
| 6,001,579 A | 12/1999 | Still | 435/7.1 |
| 6,027,890 A | 2/2000 | Ness | 435/6 |
| 6,045,676 A | 4/2000 | Mathies | 204/603 |
| 6,090,947 A | 7/2000 | Dervan | 548/312.4 |
| 6,251,581 B1 | 6/2001 | Ullman | 435/4 |
| 6,312,893 B1 | 11/2001 | Van Ness | 435/6 |
| 6,322,980 B1 | 11/2001 | Singh | 435/6 |
| 6,331,530 B1 | 12/2001 | Breslow | 514/58 |
| 6,335,201 B1 | 1/2002 | Allbritton | 436/63 |
| 6,346,529 B1 | 2/2002 | Floyd | 514/226.2 |
| 6,368,874 B1 | 4/2002 | Gallop | 436/518 |
| 6,558,928 B1 | 5/2003 | Landegren | |
| 6,627,400 B1* | 9/2003 | Singh et al. | 435/6 |
| 2002/0037542 A1 | 3/2002 | Allbritton | 435/7.23 |
| 2002/0064779 A1 | 5/2002 | Landegren et al. | |
| 2002/0128465 A1 | 9/2002 | Lyamichev | 536/24.3 |

FOREIGN PATENT DOCUMENTS

| | | |
|---|---|---|
| WO | WO 93/06121 | 4/1993 |
| WO | WO 96/24061 | 8/1996 |
| WO | WO 97/27325 | 7/1997 |
| WO | WO 97/27327 | 7/1997 |
| WO | WO 97/28275 | 8/1997 |
| WO | WO 98/01533 | 1/1998 |
| WO | WO 98/15830 | 4/1998 |
| WO | WO 99/05319 | 2/1999 |
| WO | WO 99/13108 | 3/1999 |
| WO | WO 99/42838 | 8/1999 |
| WO | WO 99/64519 | 12/1999 |
| WO | WO 00/56925 | 9/2000 |
| WO | WO 00/66607 | 11/2000 |

OTHER PUBLICATIONS

Adam et al., "Photooxygenation (Singlet Oxygen) of Tetrathioethylenes", Journal of the American Chemical Society, vol. 94:4, 1972, pp. 1206-1208.

Adam et al., "Photooxygenation of Vinyl Sulfides: Substituent Effects on the [2+2] Cycloaddition versus Schenck Ene Reaction Modes", Tetrahedron Letters, vol. 36, No. 43, Pergamon Press 1995, pp. 7853-7854.

Ando et al., "Photosensitized Oxygenation of Vinylic Sulphides", J.C.S. Chem. Comm., 1972, pp. 477-478.

Ando et al., "Singlet Oxygen Reaction—II Alkylthiosubstituted Ethylene[1]", Tetrahedron, vol. 29, Pergamon Press 1973, pp. 1507-1513.

Ando et al., "Singlet Oxygen Reaction. III. Solvent and Temperature Effects on the Photosensitized Oxygenation of Vinyl Sulfides and Vinyl Ethers", Journal of the American Chemical Society, vol. 96:21, 1974, pp. 6766-6768.

Ando et al., "Singlet Oxygen Reaction. IV. Photooxygenation of Enamines Involving a Two-Step Cleavage of a 1, 2-Dioxetane Intermediate[1]", Journal of American Chemical Society, vol. 97:17, 1975, pp. 5028-5029.

Ando et al., "Singlet Oxygen Reaction V. Ring Size Effects on the Decomposition of Sulfur Substituted 1, 2-Dioxetane[1]", Tetrahedron Letters, No. 47, Pergamon Press 1975, pp. 4127-4130.

Brenner et al., "Encoded Combinatorial Chemistry", Proc. Natl. Acad. Sci. USA, vol. 89, 1992, pp. 5381-5383.

Fitch et al., "Improved Methods for Encoding and Decoding Dialkylamine-Encoded Combinatorial Libraries", J. Comb. Chem., 1, 1999, pp. 188-194.

Giese, "Electrophoric Release Tags: Ultrasensitive Molecular Labels Providing Multiplicity", Trends in Analytical Chemistry, vol. 2, No. 7, 1983, pp. 166-168.

Gomer, "Preclinical Examination of First and Second Generation Photosensitizers Used in Photodynamic Therapy", Photochemistry and Photobiology, vol. 54, No. 6, 1991, pp. 1093-1107.

Hacia et al., "Detection of Heterozygous Mutations in BRCA1 Using High Density Oligonucleotide Arrays and Two-Colour Fluorescence Analysis", Nature Genetics, vol. 14, 1996, pp. 441-447.

Haff et al., "Multiplex Genotyping of PCR Products with MassTag-Labled Primers", Nucleic Acids Research, vol. 25, No. 18, 1997, pp. 3749-3750.

Holland et al., "Detection of Specific Polymerase Chain Reaction Product by Utilizing the 5' → 3' Exonuclease Activity of *Thermus Aquaticus* DNA Polymerase", Proc. Natl. Acad. Sci. USA, vol. 88, 1991, pp. 7276-7280.

Houghten et al., "Human β-Endorphin: Synthesis and Characterization of Analogs Iodinated and Tritiated at Tryosine Residues 1 and 27", Int. J. Peptide Protein Res., vol. 16, 1980, pp. 311-320.

Kochevar et al., "Photosensitized Production of Singlet Oxygen", Methods in Enzymology, vol. 319, 2000, pp. 20-29.

Lee et al., "Allelic Discrimination by Nick-Translation PCR with Fluorogenic Probes", Nucleic Acids Research, vol. 21, No. 16, 1993, pp. 3761-3766.

Liu et al., "Capillary Electrochromatography-laser-induced Fluorescence Method for Separation and Detection of Dansylated Dialkylamine Tags in Encoded Combinatorial Libraries", Journal of Chromatorgraphy, Art. 924, 2001, pp. 323-329.

Lu et al., "Polymerizable Fab' Antibody Fragments for Targeting of Anticancer Drugs", Nature Biotechnology, vol. 17, 1999, pp. 1101-1104.

Lum et al., "Ability of Specific Monoclonal Antibodies and Conventional Antisera Conjugated to Hematoporphyrin to Label and Kill Selected Cell Lines Subsequent to Light Activation", Cancer Research, vol. 45, 1985, pp. 4380-4386.

Marglin et al., "Chemical Synthesis of Peptides and Proteins", Art. 739, 1970, pp. 841-866.

Marino et al., "Characterization of Mitochondrial DNA Using Low-Stringency Single Specific Primer Amplification Analyzed by Laser Induced Fluoroscence—Capillary Electrophoresis", Electrophoresis, vol. 17, 1996, pp. 1499-1504.

Matthews et al., "Analytical Strategies for the Use of DNA Probes", Analytical Biochemistry, vol. 169, 1988, pp. 1-25.

Merrifield, "Solid Phase Peptide Synthesis. I. The Synthesis of a Tetrapeptide", Synthesis of a Tetrapeptide, vol. 85, 1963, pp. 2149-2154.

Ni et al., "Versatile Approach to Encoding Combinatorial Organic Synthesis Using Chemically Robust Secondary Amine Tags", J. Med. Chem., vol. 39, 1996, pp. 1601-1608.

Olejnik et al., "Photocleavable Affinity Tags for Isolation and Detection of Biomolecules", Methods in Enzymology, vol. 291, 1998, pp. 135-154.

Oseroff et al., "Antibody-Targeted Photolysis: Selective photodestruction of Human T-Cell Leukemia Cells Using Monoclonal Antibody-Chlorin e Conjugates", Proc. Natl. Acad. Sci. USA, vol. 83, 1986, pp. 8744-8748.

Pastinen et al., "Multiplex, Fluorescent, Solid-Phase Minisequencing for Efficient Screening of DNA Sequence Variation", Clinical Chemistry, vol. 42:9, 1996, pp. 1391-1397.

Posewitz et al., "Immobilized Gallium(III) Affinity Chromatography of Phosphopeptides", Anal. Chem., vol. 71, 1999, pp. 2883-2892.

Rakestraw et al., "Antibody-Targeted photolysis: *In vitro* Studies with Sn(IV) Chlorin e6 Covalently Bound to Monoclonal Antibodies Using a Modified Dextran Carrier", Proc. Natl. Acad. Sci. USA, vol. 87, 1990, pp. 4217-4221.

Da Ros et al., "DNA-Photocleavage Agents", Current Pharmaceutical Design, vol. 7, 2001, pp. 1781-1821.

Ross et al., "Discrimination of Single-Nucleotide Polymorphisms in Human DNA Using Peptide Nucleic Acid Probes Detected by MALDI-TOF Mass Spectrometry", Anal. Chem., vol. 69, 1997, pp. 4197-4202.

Sharman et al., "Role Activated Oxygen Species in Photodynamic Therapy", Methods in Enzymology, vol. 319, 2000, pp. 376-400.

Still, "Discovery of Sequence-Selective Peptide Binding by Synthetic Receptors Using Encoded Combinatorial Libraries", Acc. Chem. Res., vol. 29, 1996, pp. 155-163.

Strong, "Antibody-Targeted Photolysis", Annals New York Academy of Sciences, vol. 745, 1994, pp. 297-320.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Wang et al., "Large-Scale Identification, Mapping, and Genotyping of Single-Nucleotide Polymorphisms in the Human Genome", Science, vol. 280, 1998, pp. 1077-1082.

Wasserman et al., "Enamine-Single Oxygen Reactions. α-Diketones from Intermediate Amino Dioxetanes", Tetrahedron Letters, No. 21, 1975, pp. 1735-1738.

Wetmur, "DNA Probes: Applications of the Principles of Nucleic Acid Hybridization", Critical Reviews in Biochemistry and Molecular Biology, vol. 26, 1991, pp. 227-259.

White, "The Future of PCR Technology: Diversification of Technologies and Applications", Tibtech, vol. 14, 1996, pp. 478-483.

Wöhrle, "Porphyrins, Phthalocyanines, and Naphthalocyanines for Various Processes fo Visible Light Driven Conversion Processes", Chimia, vol. 45, 1991, pp. 307-310.

Woolley et al., "Functional Integration of PCR Amplification and Capillary Electrophoresis in a Microfabricated DNA Analysis Device", Anal. Chem., vol. 68, 1996, pp. 4081-4086.

Yarmush et al., "Antibody Targeted Photolysis", Critical Reviews in Therapeutic Drug Carrier Systems, vol. 10, 1993, pp. 197-252.

Yemul et al., "Selective Killing of T Lymphocytes by Phototoxic Liposomes", Proc. Natl. Acad. Sci. USA, vol. 84, 1987, pp. 246-250.

Zaklika et al., "Mechanisms of 1,2-Dioxetane Decomposition: The Role of Electron Transfer", Photochemistry and Photobiology, vol. 30, 1979, pp. 35-44.

Caslavska, J. et al., "Analysis of Urinary Drugs of Abuse by a Multianalyte Capillary Electrophoretic Immunosassay," *J Chromatogr A*. Apr. 9, 1999;838(1-2):197-211.

Chen, FT. et al., "Feasibility Studies for Simultaneous Immunochemical Multianalysis Drug Assay by Capillary Electrophoresis with Laser-Induced Fluorescence." Clin Chem. Sep. 1994;40(9):1819-22.

Glickman et al, "Baculovirus-mediated High Level Expression of a Mammalian DNA Methyltransferase", Biochemical and Biophysical Research Communications, Nov. 15, 1994, vol. 204, No. 3, pp. 1003-1008.

Cao, P et al, "Phosphopeptide Analysis by On-line Immobilized Methal-ion Affinity Chromatography-capillary Electrophoresis-electrospray Ionization Mass Spectrometry", Journal of Chromatography A, 1999, vol. 853, pp. 225-235.

* cited by examiner

Pro1-NHS

Pro2-NHS

Pro3-NHS

Pro4-NHS

Pro5-NHS

Pro6-NHS

Pro7-NHS

Pro8-NHS

Pro13-NHS

Pro14-NHS

ANALYZING PHOSPHORYLATED PROTEINS

This application claims priority to U.S. Provisional Application No. 60/292,548, filed May 21, 2001, and U.S. Provisional Application No. 60/334,902, filed Oct. 24, 2001, both of which are incorporated herein by reference.

The present invention relates to subject matter developed pursuant to a Joint Research Agreement between the Perkin Elmer Corporation, the R. W. Johnson Pharmaceutical Research Institute, and Aclara Biosciences, Inc. The Joint Research Agreement was executed by the parties on or about Mar. 23, 1999 or Mar. 24, 1999, and became effective Oct. 1, 1998.

The Joint Research Agreement related to Microfluidic Devices and assays suitable for use in connection with Microfluidic Devices. The present invention relates to an assay suitable for use in connection with a Microfluidic Device, e.g., an assay suitable for detecting and/or analyzing phosphorylated proteins, though one skilled in the art will readily recognize that practice of the claimed invention does not require use of a Microfluidic Device.

BACKGROUND OF THE INVENTION

The present invention relates to separable compositions, methods, and kits for use in detection and quantitation of polypeptides. The invention finds particular application to the area of multiplexed assays for polypeptides including proteins involved in phosphorylation.

The need to determine many analytes including polypeptides and nucleic acid sequences in blood or other biological fluids has become increasingly apparent in many branches of medicine. Most multi-analyte assays, such as assays in the genomics area that detect multiple nucleic acid sequences, involve multiple steps, have poor sensitivity, a limited dynamic range (typically on the order of 2 to 100-fold differences, and some require sophisticated instrumentation. Some of the known classical methods for multianalyte assays include the following:

a. The use of two different radioisotope labels to distinguish two different analytes.
b. The use of two or more different fluorescent labels to distinguish two or more analytes.
c. The use of lanthanide chelates where both lifetime and wavelength are used to distinguish two or more analytes.
d. The use of fluorescent and chemiluminescent labels to distinguish two or more analytes.
e. The use of two different enzymes to distinguish two or more analytes.
f. The use of enzyme and acridinium esters to distinguish two or more analytes.
g. Spatial resolution of different analytes, for example on arrays, to identify and quantify multiple analytes.
h. The use of acridinium ester labels where lifetime or dioxetanone formation is used to quantify two different viral targets.

Proteomics has come of interest over the last few years. While proteomics is more complex than genomics, the study of proteins gives more accurate pictures of cell biology than studying mRNA. The field of proteomics is very broad and involves areas such as, for example, protein profiling by the use of two-dimensional gel electrophoresis and mass spectrometry to study proteins expressed in the cell, protein-protein interaction using yeast two-hybrid method, pathway analysis to understand signal transduction and other complex cell processes, large scale protein folding and 3-D structure studies and high-throughput expression and purification of proteins, cellular expression during metabolism, mitosis, meiosis, in response to an external stimulus, e.g., drug, virus, change in physical or chemical condition, involving excess or deficient nutrients and cofactors, stress, aging, presence of particular strains of an organism and identifying the organism and strain, multiple drug resistance, protein-DNA interactions, protein-peptide interactions, and the like. It is necessary to have a means for identifying a large number of proteins in a single sample, as well as providing some quantitation of the different proteins being detected.

As the human genome is elucidated, there will be numerous opportunities for performing diagnostic procedures relating to the coding sequences of genes. One major function of genes is to generate proteins, which play a major role in the work carried out in a cell. Because the protein functions in a cell are dynamic, the structure, concentration, location, and so forth of a particular protein at a particular point in time is constantly changing. Analysis of protein expression patterns is the subject of ongoing genomics projects. Studies of physiologically active forms of proteins and their spatial and temporal interaction in the cell Is an important aspect of the overall study.

One post-translational modification of proteins is the addition or removal of phosphate groups. Protein phosphorylation and de-phosphorylation reactions have been established as major components of metabolic regulation and signal transduction pathways. Variations in protein phosphorylation provide the predominant means of enzymatic regulation now known in biological systems, especially in the regulation of signal transduction from cell surface receptors. Reversible phosphorylation is important for transmitting regulatory signals, including proliferative ones, in all living cells. To understand the molecular basis of these regulatory mechanisms, it is necessary to identify the specific amino acid residues that become phosphorylated. By identifying the substrates and sites of phosphorylation, diagnostic tools may be developed for some tumors and the modification of the process itself could be a target for therapeutic intervention.

Polypeptides such as growth factors, differentiation factors and hormones are crucial components of the regulatory system that coordinates development of multicellular organisms. Many of these factors mediate their pleiotropic actions by binding to and activating cell surface receptors with an intrinsic protein tyrosine kinase activity. Changes in cell behavior induced by extracellular signaling molecules such as growth factors and cytokines require execution of a complex program of transcriptional events. To activate or repress transcription, transcription factors must be located in the nucleus, bind DNA, and interact with the basal transcription apparatus. Accordingly, extracellular signals that regulate transcription factor activity may affect one or more of these processes. Most commonly, regulation is achieved by reversible phosphorylation. Phosphorylation of a transcription factor by several different kinases (or by a kinase linked to more than one pathway) is a simple mechanism that allows different signals to converge at the same factor.

There are a number of approaches in the literature directed to the analysis of phosphorylation. One such method is two-dimensional phosphopeptide mapping of $^{32}$P-labeled proteins. Another approach relies on mass spectrometry for analysis of non-radiolabeled phosphoproteins. In another approach (Cao, et al, Rapid Commun. Mass Spectrom. (2000) 14:1600–1606) phosphorylation sites of proteins are mapped using on-line immobilized metal affinity chromatography (IMAC)/capillary electrophoresis (CE)/electrospray ionization multiple stage tandem mass spectrometry (MS). The IMAC resin retains and preconcentrates phosphorylated proteins and peptides, CE separates the phosphopeptides of a mixture eluted from the IMAC resin, and MS provides information including the phosphorylation sites of each component.

A procedure for micropurification of phosphorylated peptides, as a front end to mass spectrometric analysis, is disclosed by Posewitz, et al., Anal. Chem. (1999) 71:2883–2892. Immobilized metal affinity chromatography in a microtip format and more specifically, in combination with gallium III ions is employed. Phosphopeptides are retrieved in near quantitative and highly selective manner, to yield a concentrated sample for direct analysis by matrix-assisted laser desorption/ionization time of flight and nanoelectrospray ionization mass spectrometry.

A need still exists, however, for methods for identifying and/or determining activity of and/or determining the presence and/or amounts of polypeptides involved in post-translational modification processes, such as phosphorylation. The methods should be able to identify the modification that has occurred, the site or sites of modification and the location of the sites of modification. The methods should utilize class-specific reagents where possible and be able to detect multiple polypeptides in a single assay, i.e., have a high degree of multiplexing capability. The methods should allow information to be determined in real time and allow a determination of the importance of certain polypeptides in biological pathways. Furthermore, it is important that the method permit multiplexing in order to determine whether a particular pathway is activated.

SUMMARY OF THE INVENTION

In one aspect the present invention is directed to a method for determining the presence and/or amount of one or more target polypeptides in a sample suspected of containing the target polypeptides. A mixture is formed comprising (i) the sample; (ii) a first reagent (also referred to herein as a "class-specific reagent") comprising a cleavage-inducing moiety and an immobilized metal affinity chromatography (IMAC) support specific for phosphate groups on one or more target polypeptides; and (iii) one or more electrophoretic probes each having a binding moiety specific for a target polypeptide and one or more electrophoretic tags each attached thereto by a cleavable linkage. The mixture is subjected to conditions under which binding of respective binding agent and moieties occurs. The interaction between the first binding agent and the phosphate group brings the cleavage-inducing moiety into close proximity (also referred to herein as "effective proximity") with a cleavable linkage, which is on a probe associated with the polypeptide and is susceptible to cleavage only when in proximity to the cleavage-inducing moiety. In this way, unique electrophoretic tags for each of the polypeptides may be released from the electrophoretic probe only when binding occurs. The released electrophoretic tags are then separated and the presence and/or amount of the target polypeptides are determined based on the identities and amounts of the corresponding tags. Preferably, each electrophoretic tag has unique optical and/or charge-mass characteristics.

BRIEF DESCRIPTION OF THE DRAWINGS

FIG. 13A illustrates the device; FIGS. 13B and 13C illustrate exemplary high voltage configurations utilized in the device for injection and separation, respectively.

DEFINITIONS

Figure 1:
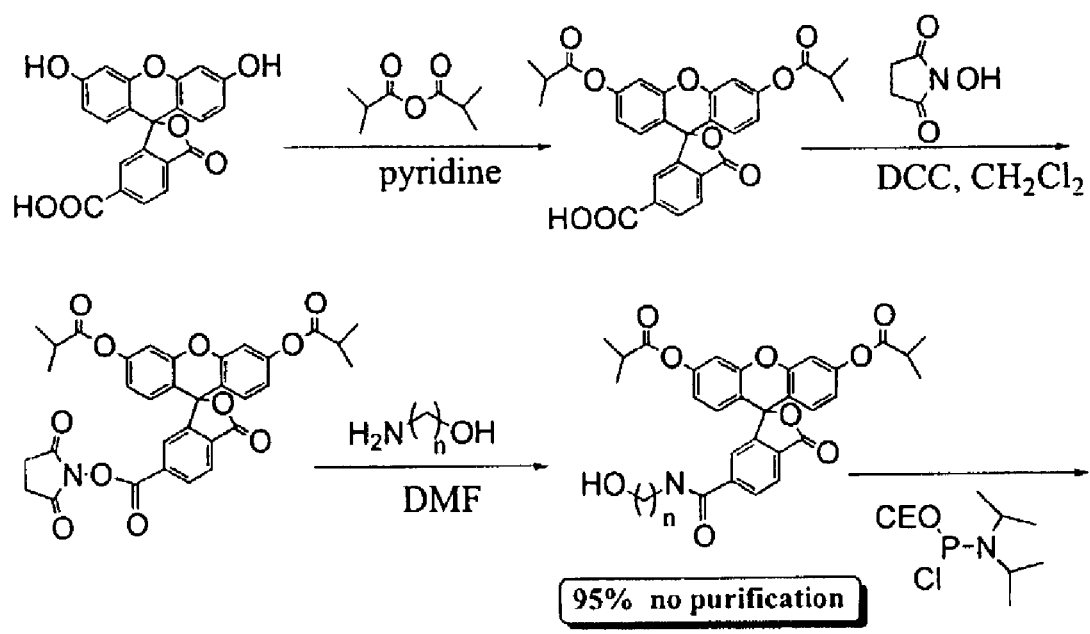
FIG. 1 illustrates one exemplary synthetic approach starting with commercially available 6-carboxy fluorescein, where the phenolic hydroxyl groups are protected using an anhydride. Upon standard extractive workup, a 95% yield of product is obtained. This material is phosphitylated to generate the phosphoramidite monomer.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained.

"Antibody binding composition" means a molecule or a complex of molecules that comprise one or more antibodies and derives its binding specificity from an antibody. Antibody binding compositions include, but are not limited to, antibody pairs in which a first antibody binds specifically to a target molecule and a second antibody binds specifically to a constant region of the first antibody; a biotinylated antibody that binds specifically to a target molecule and streptavidin derivatized with moieties such as electrophoretic tags or photosensitizers; antibodies specific for a target molecule and conjugated to a polymer, such as dextran, which, in turn, is derivatized with moieties such as electrophoretic tags or photosensitizers; antibodies specific for a target molecule and conjugated to a bead, or microbead, or other solid phase support, which, in turn, is derivatized with moieties such as electrophoretic tags or photosensitizers, or polymers containing the latter.

"Capillary electrophoresis" means electrophoresis in a capillary tube or in a capillary plate, where the diameter of the separation column or thickness of the separation plate is between about 25–500 microns, allowing efficient heat dissipation throughout the separation medium, with consequently low thermal convection within the medium.

A "sieving matrix" or "sieving medium" means an electrophoresis medium that contains crosslinked or non-crosslinked polymers which are effective to retard electrophoretic migration of charged species through the matrix.

"Specific" in reference to the binding of two molecules or a molecule and a complex of molecules refers to the specific recognition of one for the other and the formation of a stable complex as compared to substantially less recognition of other molecules and the lack of formation of stable complexes with such other molecules. Preferably, "specific" in reference to binding means that to the extent that a molecule forms complexes with other molecules or complexes, it forms at least fifty percent of the complexes with the molecule or complex for which it has specificity. Generally, the molecules or complexes have areas on their surfaces or in cavities giving rise to specific recognition between the two molecules. Exemplary of specific binding are antibody-antigen interactions, enzyme-substrate interactions, polynucleotide interactions, cellular receptor-ligand interactions, and so forth.

As used herein, the term "spectrally resolvable" in reference to a plurality of fluorescent labels means that the fluorescent emission bands of the labels are sufficiently distinct, i.e. sufficiently non-overlapping, that electrophoretic tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21–76, in Flow Cytometry: Instrumentation and Data Analysis (Academic Press, New York, 1985).

"IMAC resin" means a hydrophilic, neutral matrix having one or more metal chelators covalently attached for binding metal ions. Preferably, an IMAC resin comprises a conventional chromatographic matrix such as agarose, acrylamide, silica, or the like. Metal chelators include iminodiacetic acid (IDA), nitriloacetic acid (NTA), tetradentate, and the like. Exemplary metal ions include $Cu^{2+}$, $Ni^{2+}$, $Zn^{2+}$, $Co^{2+}$, Fe(III), Sc(III), Al(III), Lu(III), Th(III), Ga(III), and the like Description of Specific Embodiments In one aspect the present invention is directed to a method for determining the presence and/or amount of phosphorylated target polypeptides in a sample suspected of containing such polypeptides.

In another aspect of the invention, it may be desired to determine what sites on the polypeptides have been phosphorylated, how many phosphates are present on the phosphorylated polypeptides, where the phosphates are on the polypeptides, the location of the polypeptides, and so forth. On the other hand, the presence and/or amount of a target polypeptide may be used to determine the presence and/or amount and/or activity of an agent involved in bringing about the phosphorylation of the target polypeptide. In this embodiment it is desired to know whether the agent is present and/or active.

Polypeptides are a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

Proteins are polypeptide chains folded into a defined three-dimensional structure. They are complex high polymers containing carbon, hydrogen, nitrogen, and sulfur and are comprised of linear chains of amino acids connected by peptide links. The proteins are generally from about 5,000 to about 5,000,000 or more in molecular weight, more usually from about 5,000 to about 1,000,000 molecular weight. A wide variety of proteins may be considered such as a family of proteins having similar structural features, proteins having particular biological functions, proteins related to specific microorganisms, particularly disease causing microorganisms, etc. Such proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, unclassified proteins, e.g., somatotropin, prolactin, insulin, pepsin, proteins found in human plasma, blood clotting factors, blood typing factors, protein hormones, cancer antigens, tissue specific antigens, peptide hormones, nutritional markers, tissue specific antigens, and synthetic peptides.

The preferred focus of the present invention is polypeptides that include amino acid sequences modified by phosphorylation. Such modifications are well-described in basic texts and in more detailed monographs, as well as in a voluminous research literature.

Class-Specific Reagent

One reagent for conducting methods in accordance with the present invention is a class-specific reagent, or generic reagent, that comprises a cleavage-inducing moiety and a binding agent for a binding site on all, or substantially all, members of a class of target polypeptide. This reagent is a generic in the sense that its binding agent binds to all or nearly all members of a particular class of proteins. Preferably, the binding agent of the class-specific reagent is selected so that unbound materials can be separated easily from the bound material if desired. The object of this invention is the analysis of the class of phosphorylated proteins.

In one embodiment, immobilized metal affinity chromatography (IMAC) is used to capture on a solid phase, such as beads, all phosphorylated proteins contained in a sample, such as a cell lysate, e.g. as disclosed in Holmes, J. Liquid Chromatography and Rel. Technol., 20: 123–142 (1997); Posewitz et al, Anal. Chem., 71: 2883–2892 (1999); or the like. Following binding, the beads are washed by filtration. The capture and wash steps serve to concentrate the phosphoproteins and remove contaminating non-phosphorylated proteins and other cellular debris from the assay. The proteins bound to the beads are resuspended in a solution containing antibody to the candidate protein(s) of interest. Antibody may be specific for one or more designated protein targets of interest, or may be a polyclonal antibody reagent prepared against whole-cell lysate. Preferably, a collection of monoclonal antibodies is employed wherein one or more different monoclonal antibodies are specific for each phosphorylated protein in a predetermined set of such proteins. The antibody reagent has one or more e-tag moieties cleavably-linked thereon, where the linkage is susceptible to cleavage by a cleavage-inducing moiety contained on an IMAC resin, such as IMAC-24 DNP. Multiple antibody reagents, each specific for a different designated protein and each linked to a designated e-tag moiety uniquely assigned to the designated protein, may be combined for a multiplexed, target-specific determination. Following antibody binding, the linkage to the e-tag moieties will be cleaved to release a corresponding e-tag reporter, indicating capture of the designated target by the IMAC-24 DNP bead. The protein-specific or epitope-specific monoclonal antibodies may have e-tag moieties attached directly, or the e-tags may be attached to a secondary antibody specific for a constant region of the monoclonal antibody bound to a selected protein.

Metal Affinity Agent

In one embodiment of the invention a metal affinity agent in combination with an appropriate metal may be employed as the binding agent. The metal affinity agent is one that is designed to chelate a certain metal ion that has selectivity for specific groups. Accordingly, any ligand having affinity for a metal ion that binds to a binding site resulting from post-translational modification may be employed. Thus, the nature of the chelating ligand is dependent on the metal ion, which in turn is dependent on the post-translational modification. The term "metal ion" refers to ions that are derived from, for example, simple salts (e.g., $AlCl_3$, $NiCl_2$, etc.), complex or mixed salts comprising both organic and inorganic ligands and metal complexes. Metal ions of use in practicing the present invention include, for example, main group metal ions, transition metal ions, lanthanide ions, etc. Zero valent metal precursors are included in this definition. Examples of such metal ions include, by way of illustration and not limitation, ions of gallium, aluminum, iron, lead, mercury, nickel, cadmium, thallium, antimony, silver, chromium, manganese, platinum, gold, bismuth, iron, copper, zinc, cobalt, molybdenum, selenium, vanadium, calcium, Eu, Gd, Th, Sm, and so forth.

For phosphate-containing moieties such as those arising from phosphorylation of polypeptides, suitable metal ions include those having a valency of 2 or 3. Particularly preferred metal ions are gallium III, aluminum III, iron III, $CO^{+3}$, $EU^{+3}$, $Gd^{+3}$, $SM^{+3}$, $Tb^{+3}$.

The chelating ligand is usually bidentate, tridentate, or quadradentate in that the chelating ligand comprises about 2 to about 4 metal coordinating sites. The coordinating sites my comprise nitrogen, such as imino, nitrilo, pyridinyl, pyrazolyl, imidazolyl, isocyanidyl, and so forth; oxygen, such as carboxy, hydroxy, ether, keto, and so forth; phosphorus, such as phosphine, and so forth; arsenic, such as arsine, and so forth; antimony, such as stilbines, and so forth; sulfur, such as thioether, thioketo, and so forth; selenium, such as selenoether, and so forth; tellurium, such as teluroether, and so forth; and the like. Also included are combinations of the aforementioned, such as, for example, thiocarboxy, phosphinimino, oxazoles, oxazolines, thiophenes, thiazoles, isoxazoles, isothrazoles, and the like. Also included are organic moieties such as arenes, acetylenes, olefins, and the like. Specific examples of chelating ligands comprising the aforementioned groups include, by way of illustration and not limitation, iminodiacetate, tris(carboxymethyl)ethylenediamine, nitrilotriacetic acid usually substituted in the alpha position by alkyl (1–30 carbon atoms), carboxymethylated aspartic acid, 2-hydroxy-3[N-(2-pyridylmethyl)glycine]propyl, and the like.

The chelating ligand may be a metal binding peptide such as, for example, $(GHHPH)_nG$ wherein n is 1 (SEQ ID NO: 1), 2 (SEQ ID NO:2), 3 (SEQ ID NO:3) or 5 (SEQ ID NO:4)) (see, for example, Hutchens, et al., J. Chromatogr. (1992) 604:125–132 and 133–141), and so forth.

Many of the aforementioned metal chelating ligands are commercially available, others have been synthesized and the synthesis is part of the literature. Other metal chelating ligands may be synthesized by procedures well known in the art.

Antibody Agent

In one embodiment the binding agent may be an antibody for the modification on the polypeptide. For example, antibodies that recognize phosphate groups may be employed for phosphorylated polypeptides, or antibodies that recognize a sugar moiety may be employed for glycosylated polypeptides, or antibodies that recognize acetylation may be employed for acetylated polypeptides, and so forth. The antibody can be monoclonal or polyclonal. Many suitable antibodies are known in the art and/or can be prepared by techniques that are well known in the art. Such techniques include immunization of a host and collection of sera (polyclonal), by preparing continuous hybrid cell lines and collecting the secreted protein (monoclonal) or by cloning and expressing nucleotide sequences or mutagenized versions thereof coding at least for the amino acid sequences required for specific binding of natural antibodies. Antibodies include complete immunoglobulins or fragments thereof, which immunoglobulins include the various classes and isotypes, such as IgA, IgD, IgE, IgG1, IgG2a, IgG2b, and IgG3, IgM, etc. Fragments thereof may include Fab, Fv and F(ab')$_2$ Gab', and the like. In addition, aggregates, polymers, and conjugates of immunoglobulins or their fragments can be used where appropriate so long as binding affinity for a particular molecule is maintained.

In one approach to the preparation of a suitable antibody, antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974). Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra). In another approach for the preparation of antibodies the sequence coding for antibody binding sites can be excised from the chromosome DNA and inserted into a cloning vector which can be expressed in bacteria to produce recombinant proteins having the corresponding antibody binding sites. In general, antibodies can be purified by known techniques such as chromatography, e.g., DEAE chromatography, ABx chromatography, and the like, filtration, and so forth.

Cleavage-Inducing Moiety

A cleavage-inducing moiety is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226–241(2000).

An important consideration for the cleavage-inducing moiety and the cleavable linkage is that they not be so far removed from one another when bound to a target protein that the active species generated by the sensitizer diffuses and loses its activity before it can interact with the cleavable linkage. Accordingly, a cleavable linkage preferably are within 1000 nm, preferably 20–100 nm of a bound cleavage-inducing moiety. This effective range of a cleavage-inducing moiety is referred to herein as its "effective proximity."

Generators of active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH. One cleavable linkage can be based on the oxidation of sulfur or selenium, where a thioether, sulfoxide, or selenium analog thereof, is present at the α- or β-position in relation to an activating group, which makes the hydrogen a to the activating group acidic and capable of being removed by base, so as to release the oxidized functionality to which is attached the releasable portion of the e-tag, or to be subject to oxidation with release of the e-tag. Alternatively, one may use metal chelates that are stable at one oxidation state and unstable at another oxidation state. Other compounds include a -substituted methylquinones, which have the releasable portion of a reagent bonded through a leaving group, such as sulfonyl, oxy, amino, etc.

A sensitizer is a molecule, usually a compound, that can be induced to generate a reactive intermediate, or species, usually singlet oxygen. Preferably, a sensitizer used in accordance with the invention is a photosensitizer. However, other sensitizers can be employed in the present invention such as, for example, chemi-activated (e.g., enzymes and metal salts) including, by way of example and not limitation, other substances and compositions that can produce singlet oxygen with or, less preferably, without activation by an external light source. Thus, for example, molybdate ($MoO_4^-$) salts and chloroperoxidase and myeloperoxidase plus bromide or chloride ion have been shown to catalyze the conversion of hydrogen peroxide to singlet oxygen and water. For the above examples of sensitizers, hydrogen peroxide may be included as an ancillary reagent, chloroperoxidase may be bound to a surface and molybdate may be incorporated in the aqueous phase of a liposome, respectively. Other sensitizers included within the scope of the invention are compounds that are not true sensitizers but which on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994)(peroxidases and oxygenases); Kanofsky, J. Biol. Chem. 258: 5991–5993 (1983)(lactoperoxidase); Pierlot et al, Meth. Enzymol., 319: 3–20 (2000) (thermal lysis of endoperoxides); and the like.

Attachment of a binding agent to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970). A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds is well known and is amply illustrated in the literature (see above). The length of a linking group to a binding agent may vary widely, depending upon the nature of the compound being linked, the effect of the distance on the specific binding properties and the like.

Lectins may be attached to the cleavage-inducing moiety by known covalent bonding techniques. Such binding is suitably performed by cross-linking the lectin with the cleavage-inducing moiety or a hub molecule through a bifunctional cross-linking agent. Suitable bifunctional compounds are found in Review by Peters, K. and Richards, F. M., (Ann. Rev. Biochim. 46 (1977) 523). Alkyl imidates show a high degree of specificity among the functional groups presented to them by a protein. The reaction is specific for primary amino groups. Specific coupling reagents include amidoesters such as dimethyl malonimidate, azides such as the acryl azide of tartryl diazide which reacts readily with amino groups to produce amidelinkages, aryl dihalides (e.g., 1,5-difluoro-2,4-dinitrobenzene, or 4,4'-difluoro-3,3'-dinitrophenyl sulfone), glutaraldehyde, dimaleimide, mixed anhydride, mixed aromatic or aliphatic dicarboxyl, N-hydroxysuccimide ester, and other known cross-linking agents. Catalytic reagents such as 1-ethyl-3(3-dimethylamino propyl)carbodiimide hydrochloride may be used to form covalent bonds between amino groups of one molecule to carboxyl groups of another.

The class-specific reagent may be preformed or formed in situ. In the former circumstance the class-specific reagent has all of its components bound together prior to use in the present methods. In the latter situation at least some of the components of the class-specific reagent are added separately to a medium in which the present methods are conducted. In one approach the binding agent comprises a moiety for attachment of the cleavage-inducing moiety. Usually, this involves a second moiety, which is present on the cleavage-inducing moiety, where the second moiety and the moiety of the binding agent interact providing for attachment of the cleavage-inducing moiety to the binding agent and formation of the class-specific reagent in situ. Typically, the moieties interact by non-covalent attachment. This situation is exemplified by one of the two moieties comprising a small molecule (about 100 to about 1500 molecular weight) and the other of the moieties comprising a binding partner for the small molecule. For example, the small molecule may be biotin, digoxin, fluorescein, dinitrophenol, and so forth, and the binding partner for the small molecule is, respectively, avidin, antibody for digoxin, antibody for fluorescein, antibody for dinitrophenol, and so forth.

It may be desirable to have multiple cleavage-inducing moieties attached to a binding agent to increase, for example, the number of active species generated. In one approach the binding agent has a plurality of sites for attachment such as, for example, an antibody, a lectin, and so forth. To further enhance the number of cleavage-inducing moieties, a hub molecule or nucleus is employed. The hub nucleus is a polyfunctional material, normally polymeric, having a plurality of functional groups, e.g., hydroxy, amino, mercapto, carboxy, ethylenic, aldehyde, etc., as sites for linking. The functionalities on the hub should be those that are reactive with a functionality on the cleavage-inducing moiety or the binding agent to be attached. A discussion of hub nuclei is set forth below with respect to other reagents and the principles discussed below may be applied in this instance as well.

In certain embodiments the class-specific reagent comprises a support with which one of the components of the class-specific reagent is associated. The support may be comprised of an organic or inorganic, solid or fluid, water insoluble material, which may be transparent or partially transparent. The support can have any of a number of shapes, such as particle including bead, film, membrane, tube, well, strip, rod, and the like. For supports in which photosensitizer is incorporated, the surface of the support is, preferably, hydrophilic or capable of being rendered hydrophilic and the body of the support is, preferably, hydrophobic. The support may be suspendable in the medium in which it is employed. Examples of suspendable supports, by way of illustration and not limitation, are polymeric materials such as latex, lipid bilayers, oil droplets, cells and hydrogels. Other support compositions include glass, metals, polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly (vinyl butyrate), etc.; either used by themselves or in conjunction with other materials. Attachment of binding agents to the support may be direct or indirect, covalent or non-covalent and can be accomplished by well-known techniques, commonly available in the literature as discussed above. See, for example, "Immobilized Enzymes," Ichiro Chibata, supra. The surface of the support will usually be polyfunctional or be capable of being polyfunctionalized or be capable of binding to a target-binding moiety, or the like, through covalent or specific or non-specific non-covalent interactions.

The cleavage-inducing moiety may be associated with the support by being covalently or non-covalently attached to the surface of the support or incorporated into the body of the support. Linking to the surface may be accomplished as discussed above. The cleavage-inducing moiety may be incorporated into the body of the support either during or after the preparation of the support. In general, the cleavage-inducing moiety is associated with the support in an amount necessary to achieve the necessary amount of active species. Generally, the amount of cleavage-inducing moiety is determined empirically.

Photosensitizers as Cleavage-Inducing Moieties

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructing of such compositions, particularly for antibodies as binding agents, available in the literature, e.g. in the fields of photodynamic therapy, immunodiagnostics, and the like. The following are exemplary references: Ullman, et al., Proc. Natl. Acad. Sci. USA 91, 5426–5430 (1994); Strong et al, Ann. New York Acad. Sci., 745: 297–320 (1994); Yarmush et al, Crit. Rev. Therapeutic Drug Carrier Syst., 10: 197–252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; and the like.

Likewise, there is guidance in the literature regarding the properties and selection of photosensitizers suitable for use in the present invention. The following are exemplary references: Wasserman and R. W. Murray. Singlet Oxygen. (Academic Press, New York, 1979); Baumstark, Singlet Oxygen, Vol. 2 (CRC Press Inc., Boca Raton, Fla. 1983); and Turro, Modem Molecular Photochemistry (University Science Books, 1991).

The photosensitizers are sensitizers for generation of singlet oxygen by excitation with light. The photosensitizers include dyes and aromatic compounds, and are usually compounds comprised of covalently bonded atoms, usually with multiple conjugated double or triple bonds. The compounds typically absorb light in the wavelength range of about 200 to about 1,100 nm, usually, about 300 to about 1,000 nm, preferably, about 450 to about 950 nm, with an extinction coefficient at its absorbance maximum greater than about 500 $M^{-1}$ $cm^{-1}$, preferably, about 5,000 $M^{-1}$ $cm^{-1}$, more preferably, about 50,000 $M^{-1}$ $cm^{-1}$, at the excitation wavelength. The lifetime of an excited state produced following absorption of light in the absence of oxygen will usually be at least about 100 nanoseconds, preferably, at least about 1 millisecond. In general, the lifetime must be sufficiently long to permit cleavage of a linkage in a reagent in accordance with the present invention. Such a reagent is normally present at concentrations as discussed below. The photosensitizer excited state usually has a different spin quantum number (S) than its ground state and is usually a triplet (S=1) when the ground state, as is usually the case, is a singlet (S=0). Preferably, the photosensitizer has a high intersystem crossing yield. That is, photoexcitation of a photosensitizer usually produces a triplet state with an efficiency of at least about 10%, desirably at least about 40%, preferably greater than about 80%.

Photosensitizers chosen are relatively photostable and, preferably, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures.

A large variety of light sources are available to photoactivate photosensitizers to generate singlet oxygen. Both polychromatic and monchromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like.

Examples of photosensitizers that may be utilized in the present invention are those that have the above properties and are enumerated in the following references: Turro, Modern Molecular Photochemistry (cited above); Singh and Ullman, U.S. Pat. No. 5,536,834; Li et al, U.S. patent 5,763,602; Ullman, et al., Proc. Natl. Acad. Sci. USA 91, 5426–5430 (1994); Strong et al, Ann. New York Acad. Sci., 745: 297–320 (1994); Martin et al, Methods Enzymol., 186: 635–645 (1990); Yarmush et al, Crit. Rev. Therapeutic Drug Carrier Syst., 10: 197–252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; Wohrle, Chimia, 45: 307–310 (1991); Thetford, European patent publ. 0484027; Sessler et al, SPIE, 1426: 318–329 (1991); Madison et al, Brain Research, 522: 90–98 (1990); Polo et al, Inorganica Chimica Acta, 192: 1–3 (1992); Demas et al, J. Macromol. Sci., A25: 1189–1214 (1988); and the like. Exemplary photosensitizers are listed in Table 1b.

TABLE 1b

Exemplary Photosensitizers

| | |
|---|---|
| Hypocrellin A | Tetraphenylporphyrin |
| Hypocrellin B | Halogenated derivatives of rhodamine dyes |
| Hypericin | metallo-Porphyrins |
| Halogenated derivatives of fluorescein dyes | Phthalocyanines |
| Rose bengal | Naphthalocyanines |
| Merocyanine 540 | Texaphyrin-type macrocycles |
| Methylene blue | Hematophorphyrin |
| 9-Thioxanthone | 9,10-Dibromoanthracene |
| Chlorophylls | Benzophenone |
| Phenaleone | Chlorin e6 |
| Protoporphyrin | Perylene |
| Benzoporphryin A monacid | Benzoporphryin B monacid |

In certain embodiments the photosensitizer moiety comprises a support, as discussed above with respect to the cleavage-inducing moiety. The photosensitizer may be associated with the support by being covalently or non-covalently attached to the surface of the support or incorporated into the body of the support as discussed above. In general, the photosensitizer is associated with the support in an amount necessary to achieve the necessary amount of singlet oxygen. Generally, the amount of photo sensitizer is determined empirically. Photosensitizers used as the photosensitizer are preferably relatively non-polar to assure dissolution into a lipophilic member when the photosensitizer is incorporated in, for example, a latex particle to form photosensitizer beads, e.g. as disclosed by Pease et al, U.S. Pat. No. 5,709,994. For example, the photosensitizer rose bengal is covalently attached to 0.5 micron latex beads by means of chloromethyl groups on the latex to provide an ester linking group, as described in J. Amer. Chem. Soc, 97: 3741(1975).

In one aspect of the invention, a class-specific reagent comprises a first binding agent that is an antibody and a cleavage-inducing moiety that is a photosensitizer, such that the photosensitizer is covalently linked to the antibody, e.g. using well know techniques as disclosed in Strong et al (cited above); Yarmush et al (cited above); or the like. Alternatively, a class-specific reagent comprises a solid phase support, e.g. a bead, to which a photosensitizer is covalently or non-covalently attached and an antibody is attached, preferably convalently, either directly or by way of a functionalized polymer, such as amino-dextran, or the like.

Electrophoretic Probe Compositions

According to an important feature of the invention, there is provided a set of electrophoretic probes, each of which has a unique polypeptide-binding moiety and an associated "e-tag moiety" that imparts to the associated e-tag reporter, a unique electrophoretic mobility by virtue of a unique charge to mass ratio and/or optical characteristic. For convenience, the unique charge to mass ratio of an e-tag moiety is due to the chemical structure of the mobility modifier, since the detection group and linking-group residue (if any) will be common to any set of electrophoretic probes. However, it is recognized that unique charge and/or mass contributions to the e-tag reporters can be made by the detection group as well. For example, a set of electrophoretic probes may be made up of a first subset having a group of mobility modifiers which impart unique electrophoretic mobilities to the subset in combination with a detection group having one defined charge and/or mass, and a second subset having the same group of mobility modifiers in combination with a second detection group with a different charge and/or mass, thus to impart electrophoretic mobilities which are unique among both subsets.

In one aspect, the invention includes compositions comprising pluralities of electrophoretic probes. An electrophoretic probe comprises a binding moiety specific for a target polypeptide and one or more electrophoretic tags. The electrophoretic tags may be attached to the binding moiety directly or indirectly by a secondary binding molecule that binds specifically to the binding moiety, such as a secondary antibody specific for the constant region of a primary antibody. Preferably, the binding moiety of an electrophoretic probe is an antibody. Generally, an electrophoretic probe is defined by the following formula:

T-(L-E)$_k$ wherein T is the binding moiety, or more specifically, a polypeptide-binding moiety; L is a cleavable linkage; and E is an electrophoretic tag, or "e-tag." Preferably, cleavable linkage, L, is an oxidation-labile linkage, and more preferably, it is a linkage that may be cleaved by singlet oxygen.

The moiety "-(L-E)$_k$" indicates that a single binding moiety may have one or more electrophoretic tags attached via cleavable linkages. k is an integer greater than or equal to 1; and preferably, k is an integer in the range of from 1 to 500; and more preferably, k is an integer in the range of from 1 to 100 or from 1 to 50; and still more preferably, k is an integer in the range of from 1 to 10. Preferably, the plurality of electrophoretic probes is at least 5, and more preferably, at least 10. Still more preferably, the plurality is in the range of from 5 to 200, and more preferably, from 5 to 100, or from 5 to 50, or from 10 to 30. Preferably, within a plurality, each different binding moiety, T, has a different electrophoretic tag, E. Oxidation-labile linkages and tags, E, are attached to T by way of conventional linking chemistries. Preferably, whenever T is a polypeptide attachment may be through the common reactive functionalities, such as amino, sulfide, carboxyl, and the like.

Preferably, binding moiety, T, is an antibody, or comprises an antibody, specific for a target protein, or polypeptide. In the latter case, T may comprise a plurality of binding components that operate together to hold an electrophoretic tag in the proximity of a target protein. For example, T may be an antibody together with a secondary antibody having e-tags attached, a haptenized antibody together with a secondary anti-hapten antibody having e-tags attached, a biotinylated antibody together with streptavidin having e-tags attached, an antibody derivatized with a functionalized polymer that, in turn, has e-tags attached, or the like. A plurality of electrophoretic probes are preferably used in the method of the invention, wherein each probe has a different binding moiety, T.

Preferably, L is a thioether or its selenium analog; or an olefin, which contains carbon-carbon double bonds, wherein cleavage of a double bond to an oxo group, releases the e-tag, E. Illustrative olefins include vinyl sulfides, vinyl ethers, enamines, imines substituted at the carbon atoms with an α-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C, by reaction with acid or base, or by photo-activation in the absence or presence of a photosensitizer. Such reactions are described in the following exemplary references: Adam and Liu, J. Amer. Chem. Soc. 94, 1206–1209, 1972, Ando, et al., J. C. S. Chem. Comm. 1972, 477–8, Ando, et al., Tetrahedron 29, 1507–13, 1973, Ando, et al., J. Amer. Chem. Soc. 96, 6766–8, 1974, Ando and Migita, ibid. 97, 5028–9, 1975, Wasserman and Terao, Tetra. Lett. 21, 1735–38, 1975, Ando and Watanabe, ibid. 47, 4127–30, 1975, Zaklika, et al., Photochemistry and Photobiology 30, 35–44, 1979, and Adam, et al., Tetra. Lett. 36, 7853–4, 1995. See also, U.S. Pat. No. 5,756,726.

The formation of dioxetanes is obtained by the reaction of singlet oxygen with an activated olefin substituted with an e-tag moiety at one carbon atom and the binding moiety at the other carbon atom of the olefin. See, for example, U.S. Pat. No. 5,807,675. These cleavable linkages may be depicted by the following formula:

—W—(X)$_n$C$_\alpha$=C$_\beta$(Y)(Z)— wherein:
  W may be a bond, a heteroatom, e.g., O, S, N, P, M (intending a metal that forms a stable covalent bond), or a functionality, such as carbonyl, imino, etc., and may be bonded to X or $C_\alpha$;

at least one X will be aliphatic, aromatic, alicyclic or heterocyclic and bonded to $C_\alpha$ through a hetero atom, e.g., N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to $C_\beta$ through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to $C_\beta$ or through a heteroatom, as described above;

n is 1 or 2, depending upon whether the e-tag moiety is bonded to $C_\alpha$ or X;

wherein one of Y and Z will have a functionality for binding to the binding moiety, or be bound to the binding moiety, e.g. by serving as, or including a linkage group, to a binding moiety, T.

Preferably, W, X, Y, and Z are selected so that a minimally sized group is imparted to electrophoretic tag, E, upon cleavage.

While not depicted in the formula, one may have a plurality of e-tag moieties in a single molecule, by having one or more e-tag moieties joined to one or both Xs.

Illustrative cleavable linkages include S-3-thiolacrylic acid, -N, N-methyl 4-amino-4-butenoic acid, —O, 3-hydroxyacrolein, N-(4-carboxyphenyl) 2-imidazole, oxazole, and thiazole.

Also of interest are N-alkyl acridinyl derivatives, substituted at the 9 position with a divalent group of the formula:

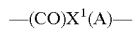
—(CO)$X^1$(A)— wherein:

$X^1$ is a heteroatom selected from the group consisting of O, S, N, and Se, usually one of the first three; and A is a chain of at least 2 carbon atoms and usually not more than 6 carbon atoms substituted with an e-tag reporter, where preferably the other valences of A are satisfied by hydrogen, although the chain may be substituted with other groups, such as alkyl, aryl, heterocyclic groups, etc., A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the e-tag reporter.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the e-tag reporter. The rings may be coumarin, benzoxazine, tetralin, etc.

Electrophoretic tag, E, is a water soluble organic compound that is stable with respect to the active species, especially singlet oxygen, and that includes a detection or reporter group. Otherwise, E may vary widely in size and structure. Preferably, E carries a charge at neutral pH and has a molecular weight in the range of from about 150 to about 10,000, and more preferably, from about 150 to about 2500. There are several preferred structures of E that are described more fully below. Preferably, the detection group generates an electrochemical, fluorescent, or chromogenic signal. Most preferably, the detection group generates a fluorescent signal. Compositions of the invention include pluralities of electrophoretic tags that may be used together to carry out the multiplexed assays of the invention. Preferably, the plurality of electrophoretic tags in a composition is at least 5, and more preferably, at least 10. Still more preferably, the plurality is in the range of from 5 to 200, and more preferably, from 5 to 100, or 5 to 75, or from 5 to 50, or from 10 to 30. Preferably, electrophoretic tags within a plurality of a composition each have either a unique charge-to-mass ratio and/or a unique optical property with respect to the other members of the same plurality. Preferably, the optical property is a fluorescence property, such as emission spectrum, fluorescence lifetime, or the like. More preferably, the fluorescence property is emission spectrum. For example, each electrophoretic tag of a plurality may have the same fluorescent emission properties, but each will differ from one another by virtue of unique charge-to-mass ratios, On the other hand, or two or more of the electrophoretic tags of a plurality may have identical charge-to-mass ratios, but they will have unique fluorescent properties, e.g. spectrally resolvable emission spectra, so that all the members of the plurality are distinguishable by the combination of electrophoretic separation and fluorescence measurement.

Preferably, electrophoretic tags in a plurality are detected by electrophoretic separation and fluorescence. Preferably, electrophoretic tags having substantially identical fluorescence properties have different electrophoretic mobilities so that distinct peaks in an electropherogram are formed under separation conditions. A measure of the distinctness, or lack of overlap, of adjacent peaks is electrophoretic resolution, which is the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of electrophoretic tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like. Preferably, pluralities of electrophoretic tags of the invention are separated by conventional capillary electrophoresis apparatus, either in the presence or absence of a conventional sieving matix. Exemplary capillary electroresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Preferably, in such conventional apparatus, the electrophoretic mobilities of electrophoretic tags of a plurality differ by at least one percent, and more preferably, by at least a percentage in the range of from 1 to 10 percent.

Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more.

A preferred structure of electrophoretic tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "T-L-(M, D)" designates electrophoretic probe of either of two forms: "T-L-M-D" or "T-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-solubler-hodamine dyes, fluoresceins, 4,7-dichlorofluoresceins, benzoxanthene dyes, and energy transfer dyes, disclosed in the following references: Handbook of Molecular Probes and Research Reagents, 8th ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816–2822 (1997); Hobb, Jr., U.S. Pat. No. 4,997,928; Khanna et al., U.S. Pat. No. 4,318,846; Reynolds, U.S. Pat. No. 3,932,415; Eckert et al, U.S. Pat. No. 2,153,059; Eckert et al, U.S. Pat. No. 2,242,572; Taing et al, International patent publication WO 02/30944; and the like. Further specific exemplary fluorescent dyes include 5- and 6-carboxyrhodamine 6G; 5- and 6-carboxy-X-rhodamine, 5- and 6-carboxytetramethylrhodamine, 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein.

M is generally a chemical group or moiety that has or is designed to have a particular charge-to-mass ratio, and thus a particular electrophoretic mobility in a defined electrophoretic system. Exemplary types of mobility-modifying moieties are discussed below. In a set of n electrophoretic probes, each unique mobility modifier is designated $M_j$, where j=1 to n, and n has a value as described above. The mobility-modifying moiety may be considered to include a mass-modifying region and/or a charge-modifying region or a single region that acts as both a mass- and charge-modifying region. In the probe sets utilized in the invention, the mobility-modifying moiety may have one or more of the following characteristics: (i) a unique charge-to-mass ratio due to variations in mass, but not charge; (ii) a unique charge-to-mass ratio due to changes in both mass and charge; and (ii) a unique charge-to-mass ratios of between about −0.0001 and about 0.5, usually, about −0.001 and about 0.1. As noted above, D is typically common among a set or plurality of different electrophoretic probes, but may also differ among probe sets, contributing to the unique electrophoretic mobilities of the released e-tag.

The size and composition of mobility-modifying moiety, M, can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mobility-modifying moiety has from about 0 to about 40, more usually from about 0 to about 30 heteroatoms, which in addition to the heteroatoms indicated above may include halogen or other heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphate, phosphonate, phosphinate, sulfonate, sulfinate, boronic, nitric, nitrous, etc. For positive charges, substituents include amino (includes ammonium), phosphonium, sulfonium, oxonium, etc., where substituents are generally aliphatic of from about 1–6 carbon atoms, the total number of carbon atoms per heteroatom, usually be less than about 12, usually less than about 9. The side chains include amines, ammonium salts, hydroxyl groups, including phenolic groups, carboxyl groups, esters, amides, phosphates, heterocycles. M may be a homo-oligomer or a hetero-oligomer, having different monomers of the same or different chemical characteristics, e.g., nucleotides and amino acids.

The charged mobility-modifying moieties generally have only negative or positive charges, although one may have a combination of charges, particularly where a region to which the mobility-modifying moiety is attached is charged and the mobility-modifying moiety has the opposite charge. The mobility-modifying moieties may have a single monomer that provides the different functionalities for oligomerization and carry a charge or two monomers may be employed, generally two monomers. One may use substituted diols, where the substituents are charged and dibasic acids. Illustrative of such oligomers is the combination of diols or diamino, such as 2,3-dihydroxypropionic acid, 2,3-dihydroxysuccinic acid, 2,3-diaminosuccinic acid, 2,4-dihydroxyglutaric acid, etc. The diols or diamino compounds can be linked by dibasic acids, which dibasic acids include the inorganic dibasic acids indicated above, as well as dibasic acids, such as oxalic acid, malonic acid, succinic acid, maleic acid, fumaric acid, carbonic acid, etc. Instead of using esters, one may use amides, where amino acids or diamines and diacids may be employed. Alternatively, one may link the hydroxyls or amines with alkylene or arylene groups.

By employing monomers that have substituents that provide for charges, or which may be modified to provide charges, one can provide for mobility-modifying moieties having the desired charge-to-mass ratio. For example, by using serine or threonine, one may modify the hydroxyl groups with phosphate to provide negatively charged mobility-modifying moieties. With arginine, lysine and histidine, one provides for positively charged mobility-modifying moieties. Oligomerization may be performed in conventional ways to provide the appropriately sized mobility-modifying moiety. The different mobility-modifying moieties having different orders of oligomers, generally having from 1 to 20 monomeric units, more usually about 1 to 12, where a unit intends a repetitive unit that may have from 1 to 2 different monomers. For the most part, oligomers may be used with other than nucleic acid target-binding regions. The polyfunctionality of the monomeric units provides for functionalities at the termini that may be used for conjugation to other moieties, so that one may use the available functionality for reaction to provide a different functionality. For example, one may react a carboxyl group with an aminoethylthiol, to replace the carboxyl group with a thiol functionality for reaction with an activated olefin.

By using monomers that have about 1 to about 3 charges, one may employ a low number of monomers and provide for mobility variation with changes in molecular weight. Of particular interest are polyolpolycarboxylic acids having from about two to four of each functionality, such as tartaric acid, 2,3-dihydroxyterephthalic acid, 3,4-dihydroxyphthalic acid, $\Delta^5$-tetrahydro-3,4-dihydroxyphthalic acid, etc. To provide for an additional negative charge, these monomers may be oligomerized with a dibasic acid, such as a phosphoric acid derivative to form the phosphate diester. Alternatively, the carboxylic acids could be used with a diamine to form a polyamide, while the hydroxyl groups could be used to form esters, such as phosphate esters, or ethers such as the ether of glycolic acid, etc. To vary the mobility, various aliphatic groups of differing molecular weight may be employed, such as polymethylenes, polyoxyalkylenes, polyhaloaliphatic or aromatic groups, polyols, e.g., sugars, where the mobility will differ by at least about 0.01, more usually at least about 0.02 and more usually at least about 0.5.

In another aspect, (M,D) moieties are constructed from chemical scaffold used in the generation of combinatorial libraries. For example, the following references describe scaffold compound useful in generating diverse mobility modifying moieties: peptoids (PCT Publication No WO 91/19735, Dec. 26, 1991), encoded peptides (PCT Publication WO 93/20242, Oct. 14 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. U.S.A. 90: 6909–6913 (1993), vinylogous polypeptides (Hagihara et al. J. Amer. Chem. Soc. 114: 6568 (1992)), nonpeptidal peptidomimetics with a Beta-D-Glucose scaffolding (Hirschmann, R. et al., J.Amer. Chem. Soc. 114: 9217–9218 (1992)), analogous organic syntheses of small compound libraries (Chen, C. et al. J.Amer. Chem. Soc. 116: 2661(1994)), oligocarbamates (Cho, C. Y. et al. Science 261: 1303(1993)), peptidyl phosphonates (Campbell, D. A. et al., J. Org. Chem. 59:658 (1994)); Cheng et al, U.S. Pat. No. 6,245,937; Heizmann et al, "Xanthines as a scaffold for molecular diversity," Mol. Divers. 2: 171–174 (1997); Pavia et al, Bioorg. Med. Chem., 4: 659–666 (1996); Ostresh et al, U.S. Pat. No. 5,856,107; Gordon, E. M. et al., J. Med. Chem. 37: 1385 (1994); and the like.

In yet another aspect, (M, D) moieties are constructed from common or commercially available linking, cross-linking, and labeling reagents that permit facile assembly, especially using a commercial DNA or peptide synthesizer for all or part of the synthesis. In this aspect, (M, D) moieties are made up of subunits usually connected by phosphodiester and amide bonds. Exemplary, precursors include, but are not limited to, dimethoxytrityl (DMT)-protected hexaethylene glycol phosphoramidite, 6-(4-Monomethoxytritylamino)hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl)aminoethoxy] ethyl-(2-cyanoethyl), N,N-diisopropyl)-phosphoramidite, (S-Trityl-6-mercapto-hexyl)-(2-cyanoethyl)-(N,N-diisopropyl)-phosphoramidite, 5'-Fluorescein phosphoramidite, 5'-Hexachloro-Fluorescein Phosphoramidite, 5'-Tetrachloro-Fluorescein Phosphoramidite, 9-O-Dimethoxytrityl-triethylene glycol,1-[(2-cyanoethyl)-(N,N-diisopropyl)]-phosphoramidite, 3 (4,4'Dimethoxytrityloxy)propyl-1-[(2-cyanoethyl)-(N,N-diisopropyl)]-phosphoramidite, 5'-O-Dimethoxytrityl-1',2'-Dideoxyribose-3 '-[(2-cyanoethyl)-(N,N-diisopropyl)]-phosphoramidite, 18-O Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'-dimethoxytrityloxy)pentylamido]propyl-2-[(2-cyanoethyl)-(N,N-disopropyl)]-phosphoramidite, 1-[5-(4,4'-dimethoxytrityloxy)pentylamido]-3-[5-fluorenomethoxycarbonyloxy pentylamido]-propyl-2-[(2-cyanoethyl)-(N,N-diisopropyl)]-phosphoramidite, Tris-2,2, 2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, Texas Red-X-succinimidyl ester, 5- and 6-carboxytetramethylrhodamine succinimidyl ester, bis-(4-carboxypiperidinyl)sulfonerhodamine di(succinimidyl ester), 5- and 6-((N-(5-aminopentyl)aminocarbonyl)tetramethylrhodamine, succinimidyl 4-(p-maleimidophenyl)butyrate (SMPB); N-γ-maleimidobutyryl-oxysuccinimide ester (GMBS); p-nitrophenyl iodoacetate (NPIA); 4-(4-N-maleimidophenyl)butyric acid hydrazide (MPBH); and like reagents. The above reagents are commercially available, e.g. from Glen Research (Sterling, Va.), Molecular Probes (Eugene, Oreg.), Pierce Chemical, and like reagent providers. Use of the above reagents in conventional synthetic schemes is well known in the art, e.g. Hermanson, Bioconjugate Techniques (Academic Press, New York, 1996).

In another aspect, the detection moiety of (M,D) generates a fluorescent signal by an energy transfer mechanism. Preferably, in this aspect, D has the form "$D_1$-g-$D_2$" where $D_1$ and $D_2$ are acceptor-donner pairs of molecules, e.g. Wu et al, Anal. Biochem., 218: 1–13 (1994), and g is a rigid linker that maintains $D_1$ and $D_2$ at a substantially constant distance. Either $D_1$ or $D_2$ may be the acceptor and the other the donner molecule in the pair. Exemplary, energy transfer detection moieties for use with the invention are disclosed in Lee et al, U.S. Pat. No. 5,945,526; Lee et al, Nucleic Acids Research, 25: 2816–2822 (1997); Taing et al, International patent publication WO 02/30944; and like references. Preferably, rigid linker, g, is selected so that the distance between $D_1$ and $D_2$ is maintained at a substantially constant distance within the range of from 10–100 Angstroms. Preferably, $D_1$ and $D_2$ are selected from the set of fluorescein, rhodamine, rhodamine 6G, rhodamine 110, rhodamine X, tetramethylrhodamine, and halogenated derivatives thereof.

In some embodiments the e-tag moieties need not be charged but merely differ in mass. Thus, one could use the same or similar monomers, where the functionalities would be neutral or made neutral, such as esters and amides of carboxylic acids. Also, one may vary the e-tag moieties by isotopic substitution, such as $^2H$, $^{18}O$, $^{14}C$, etc.

Pluralities of electrophoretic tags may include oligopeptides for providing the charge, particularly oligopeptides of from 2–6, usually 2–4 monomers, either positive charges resulting from lysine, arginine and histidine or negative charges, resulting from aspartic and glutamic acid. Of course, one need not use naturally occurring amino acids, but unnatural or synthetic amino acids, such as taurine, phosphate substituted serine or threonine, S-α-succinylcysteine, co-oligomers of diamines and amino acids, etc.

In one embodiment of the present invention, the charge-imparting moiety is conveniently composed primarily of amino acids but also may include thioacids and other carboxylic acids having from one to five carbon atoms. The charge imparting moiety may have from about 1 to about 30, preferably about 1 to about 20, more preferably, about 1 to about 10 amino acids per moiety and may also comprise about 1 to about 3 thioacids or other carboxylic acids. However, when used with an uncharged sub-region, the charged sub-region will generally have from about 1 to about 4, frequently about 1 to about 3 amino acids. As mentioned above, any amino acid, both naturally occurring and synthetic, may be employed.

In a particular embodiment, T-L-M-D may be represented by the formula:

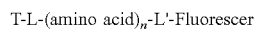

T-L-(amino acid)$_n$-L'-Fluorescer wherein L' is a bond or a linking group of from 1 to 20 atoms other than hydrogen, n is 1 to 20, and L is a cleavable linkage to the polypeptide-binding moiety. In this embodiment T is linked to the terminal amino acid by a cleavable linkage. An example of this embodiment, by way of illustration and not limitation, is one in which the fluorescer is fluorescein, L' is a bond in the form of an amide linkage involving the meta-carboxyl of the fluorescein and the terminal amine group of lysine, and T is a polypeptide-binding moiety.

In another embodiment, mobility-modifying moiety, M, is dependent on using an alkylene or aralkylene (comprising a divalent aliphatic group having about 1 to about 2 aliphatic regions and about 1 to about 2 aromatic regions, generally benzene), where the groups may be substituted or unsubstituted, usually unsubstituted, of from about 2 to about 16, more usually about 2 to about 12, carbon atoms, where the mobility-modifying moiety may link the same or different fluorescers to a monomeric unit, e.g., a nucleotide. The mobility-modifying moiety may terminate in a carboxy, hydroxy or amino group, being present as an ester or amide. By varying the substituents on the fluorophore, one can vary the mass in units of at least about 5 or more, usually at least about 9, so as to be able to obtain satisfactory separation in capillary electrophoresis. To provide further variation, a thiosuccinimide group may be employed to join alkylene or aralkylene groups at the nitrogen and sulfur, so that the total number of carbon atoms may be in the range of about 2 to about 30, more usually about 2 to about 20. Instead of or in combination with the above groups and to add hydrophilicity, one may use alkyleneoxy groups.

Besides the nature of the mobility-modifying moiety, as already indicated, diversity can be achieved by the chemical and optical characteristics of the label, the use of energy transfer complexes, variation in the chemical nature of the mobility-modifying moiety, which affects mobility, such as folding, interaction with the solvent and ions in the solvent, and the like. In one embodiment of the invention, the mobility-modifying moiety may be an oligomer, where the mobility-modifying moiety may be synthesized on a support or produced by cloning or expression in an appropriate host. Conveniently, polypeptides can be produced where there is only one cysteine or serine/threonine/tyrosine, aspartic/ glutamic acid, or lysine/arginine/histidine, other than an end group, so that there is a unique functionality, which may be differentially functionalized. By using protective groups, one can distinguish a side-chain functionality from a terminal amino acid functionality. Also, by appropriate design, one may provide for preferential reaction between the same functionalities present at different sites on the mobility-modifying moiety. Whether one uses synthesis or cloning for preparation of oligopeptides, is to a substantial degree depend on the length of the mobility-modifying moiety.

Substituted aryl groups can serve as both mass- and charge-modifying regions. Various functionalities may be substituted onto the aromatic group, e.g., phenyl, to provide mass as well as charges to the e-tag reporter. The aryl group may be a terminal group, where only one linking functionality is required, so that a free hydroxyl group may be acylated, may be attached as a side chain to an hydroxyl present on the e-tag reporter chain, or may have two functionalities, e.g., phenolic hydroxyls, that may serve for phosphite ester formation and other substituents, such as halo, haloalkyl, nitro, cyano, alkoxycarbonyl, alkylthio, etc. where the groups may be charged or uncharged.

The label conjugates may be prepared utilizing conjugating techniques that are well known in the art. M may be synthesized from smaller molecules that have functional groups that provide for linking of the molecules to one another, usually in a linear chain. Such functional groups include carboxylic acids, amines, and hydroxy- or thiol-groups. In accordance with the present invention the charge-imparting moiety may have one or more side groups pending from the core chain. The side groups have a functionality to provide for linking to a label or to another molecule of the charge-imparting moiety. Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g., sulfonate, phosphate esters, sulfonamides, thioesters, etc., and the like.

The linkages of the components of the e-tag moiety are discussed above. The linkage between the detectable moiety and the mobility-modifying moiety is generally stable to the action of the cleavage-inducing moiety, so that the mobility-modifying moiety and detectable moiety may be released as an intact unit from the e-tag probe during the cleavage of the e-tag reporter from the e-tag probe.

For the most part, the mobility-modifying moiety may be a bond, where the detectable moiety or label is directly bonded to the target-binding moiety, or a link of from about 1 to about 500 or more, usually about 1 to about 300 atoms, more usually about 2 to about 100 atoms in the chain. In this embodiment, the total number of atoms in the chain will depend to a substantial degree on the diversity required to recognize all the targets to be determined. The chain of the mobility-modifying moiety for the most part is comprised of carbon, nitrogen, oxygen, phosphorous, boron, and sulfur. Various substituents may be present on the mobility-modifying moiety, which may be naturally present as part of the naturally occurring monomer or introduced by synthesis. Functionalities which may be present in the chain include amides, phosphate esters, ethers, esters, thioethers, disulfides, borate esters, sulfate esters, etc. The side chains include amines, ammonium salts, hydroxyl groups, including phenolic groups, carboxyl groups, esters, amides, phosphates, heterocycles, particularly nitrogen heterocycles, such as the nucleoside bases and the amino acid side chains, such as imidazole and quinoline, thioethers, thiols, or other groups of interest to change the mobility of the electrophoretic tag.

The mobility-modifying moiety may be a homooligomer or a heterooligomer, having different monomers of the same or different chemical characteristics, e.g., nucleotides and amino acids. In one embodiment, the e-tag moieties will have a linker, which provides the linkage between the mobility-modifying moiety and the detectable label molecule, usually a fluorescer, or a functionality that may be used for linking to a detectable label molecule. By having different functionalities, which may be individually bonded to a detectable label molecule, one enhances the opportunity for diversity of the electrophoretic tags. Using different fluorescers for joining to the different functionalities, the different fluorescers can provide differences in light emission and charge-to-mass ratios for the electrophoretic tags.

Attaching Multiple Electrophoretic Tags to Binding Moieties

In assays involving polypeptides, it is advantageous to have the release of multiple e-tag reporters for a binding event involving an individual target molecule. In a sense, this results in an amplification of signal. Desirably, the number of e-tag reporters released for each such binding event is about $6 \times 10^3$ to about $6 \times 10^{10}$, preferably, about $6 \times 10^4$ to about $6 \times 10^8$. Where the polypeptide-binding moiety has a plurality of sites for attachment such as, for example, an antibody, there is a plurality of binding sites on the antibody for attachment of e-tag moieties. When the polypeptide-binding moiety of the e-tag probe binds to the polypeptide and the first binding moiety of the first binding agent binds to the induced binding site on the polypeptide thus bringing a cleavage-inducing moiety into close proximity to the cleavable linkage, a plurality of e-tag reporters is released for a binding event involving a single polypeptide. For example, attachment of e-tag moieties to an antibody may result in about 2 to about 10 molecules of e-tag moieties per antibody molecule.

To further enhance the number of e-tag reporters released, the e-tag moieties are cleavably attached to a hub, to which a polypeptide-binding moiety of the e-tag probe is also attached in a relatively permanent manner. For a polypeptide-binding moiety that has a plurality of attachment sites, a plurality of hubs may be attached to the polypeptide-binding moiety where each hub has a plurality of e-tag moieties for release. The hub nucleus is, therefore, a polyfunctional material, normally polymeric, having a plurality of functional groups, e.g., hydroxy, amino, mercapto, carboxy, ethylenic, aldehyde, etc., as sites for linking. The functionalities on the hub should be those that are reactive with a functionality on the e-tag moiety or the polypeptide-binding moiety to be attached. Some functionalities are preferred over others because of their ability to resist participation in unwanted side reactions. The hub nucleus may be water soluble or water insoluble. The hub nucleus is usually at least about 35,000 molecular weight and may be about 10 million or more molecular weight, but usually under about 600,000, more usually under about 300,000. Illustrative hub nuclei include polysaccharides, polypeptides, polynucleotides, ion exchange resins, and the like. The hub is in one aspect a branched linker, which has multiple sites for attachment of e-tag moieties. The multiple site linkers have an attachment site for attaching the polypeptide-binding moiety and a plurality of sites for attachment of a plurality of e-tag moieties. Of course, the e-tag moieties must be attached by means of linkages that comprise a functionality that is cleavable by the cleavage-inducing moiety in accordance with the present invention.

In one embodiment the hub nucleus is a hydrophilic polymer, generally, an addition or condensation polymer with multiple functionality to permit the attachment of multiple moieties. One class of polymers that is useful for the reagents of the present invention comprises the polysaccharide polymers. Polysaccharides such as dextrans, sepharose, polyribose, polyxylose, and the like may be used. Another class of polymers are those that result from the addition polymerization of substituted ethylene and butadiene type monomers, including short chain unsaturated monomers such as propylene, wherein these monomers have substituents that are hydrophilic groups or can be derivatized to hydrophilic groups. Suitable hydrophilic groups that may be attached to the ethylene include hydroxy, carboxy and the ester and amides thereof, amines, and the like. If acrylic acid monomers are used, the acid can be derivatized to suitable reactive groups prior to or subsequent to polymerization. Thus, for example, the ester formed from ethylene glycol and acrylic acid provides a hydroxyl group for derivatization to the components of the e-tag probe. Other suitable polymers include polyallyl amines and alcohols such as, for example, polyvinyl alcohol. In addition to utilizing polymers derived from a single monomer, mixed polymers may also be employed. In this case, the hydrophilicity may be provided by a non-reactive component such as polyethylene glycol, which is then further polymerized to monomers that bear the appropriate functional groups for reaction with the components of the e-tag probe. One such polymer is a copolymer of polyethylene glycol with polyvinyl alcohol. One specific example of a hub is dextran to which about 10 to about 300 molecules of e-tag moieties may be attached per one molecule of dextran.

A particle may be employed to enhance the number of e-tag moieties present in the e-tag probe. The particles may be solid (e.g., comprised of organic and inorganic polymers or latex), oil droplets (e.g., hydrocarbon, fluorocarbon, silicon fluid), or vesicles (e.g., synthetic such as phospholipid or natural such as cells and organelles). The solid particles are normally polymers, either addition or condensation polymers, which are readily dispersible in an assay medium. The e-tag moieties are linked to the particle by cleavable linkages consistent with the present invention. In this way about 100 to about $10^5$ e-tag moieties may be linked to a single particle. The particle usually has at least one polypeptide-binding moiety attached to it. It is also within the purview of the present invention to attach multiple dextran molecules to the particle and to link multiple e-tag moieties to the dextran by means of cleavable linkages as discussed above.

In a particular embodiment of an e-tag probe of the invention, the polypeptide-binding moiety is an antibody. A number of different reactions may be used to covalently attach compounds to antibodies. This has been accomplished by reaction of the amino acid residues of the antibody molecule, including the amine groups of lysine, the free carboxylic acid groups of glutamic and aspartic acid, the sulfhydryl groups of cysteine and the various moieties of the aromatic amino acids. The conjugation to an antibody may be random or site-directed. For site-directed conjugation the linker or mobility-modifying moiety may be joined in any convenient manner to a unit of the target-binding moiety, such as the Fc portion of an antibody or disulfides in the hinge region. For random conjugation amine groups (e.g., N-terminal or lysine) of the antibody may be employed. Alternatively, carboxylate groups (e.g., C-terminal, aspartic acid, glutamic acid) may be used. Other examples include thiol groups. A primary consideration in binding to an antibody is retention of antibody recognition properties or specificity and activity.

Specific approaches are known for attachment to an antibody. One such approach is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of the antibody molecule. In another approach a Schiff base reaction is employed to link compounds to antibody molecules. This method involves the periodate oxidation of the compound to be linked that contains glycol or hydroxy groups, thus forming an aldehyde that is then reacted with the antibody molecule. Attachment occurs via formation of a Schiff base with amino groups of the antibody molecule. Furthermore, isocyanates have been used as coupling agents for covalently attaching compound to antibodies. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiocarbazide groups. Such reactive functional groups may exist as part of the structure of the linker, or may be introduced by suitable chemical modification of linkers not containing such groups.

In a particular approach an antibody containing polysaccharide chains is oxidized to produce reactive aldehyde groups. Such oxidation may be achieved by, for example, periodate as known in the art. Hub molecules such as, for example, amino-dextran molecules, having e-tag moieties attached thereto by cleavable linkages are attached to the aldehyde groups on the antibody by reductive amination forming secondary amine linkages.

Accordingly, in the present invention one or more hub molecules may be attached to an antibody by one of the aforementioned approaches to achieve relatively permanent linkage under the conditions employed in the present methods. Of course, consistent with the present invention the e-tag moieties are attached to the hub by means of a cleavable linkage or attached directly to the antibody by means of such cleavable linkage. Upon the binding of a polypeptide by the first binding agent and by the e-tag probe comprising the antibody, which brings the e-tag probe in close proximity to the cleavage-inducing reagent, multiple e-tag reporters are released for subsequent detection and for relating to the presence and/or amount of a polypeptide present.

As used herein, the term "capture ligand," refers to a group that is typically included within the target-binding moiety portion of an e-tag probe and is capable of binding specifically to a "capture agent" or receptor. The interaction between such a capture ligand and the corresponding capture agent may be used to separate uncleaved e-tag probes from released e-tag reporters. If desired, the receptor may be used to physically sequester the molecules to which it binds, entirely removing intact e-tag probes containing the polypeptide-binding region or modified polypeptide-binding regions retaining the ligand. These modified polypeptide-binding regions may be as a result of degradation of the starting material, contaminants during the preparation, aberrant cleavage, etc., or other nonspecific degradation products of the polypeptide binding moiety. As above, a ligand, exemplified by biotin, is attached to the polypeptide-binding region so as to be separated from the e-tag reporter upon cleavage.

A receptor for the ligand may be used. Such receptors include natural or synthetic receptors, such as immunoglobulins, lectins, enzymes, etc., avidin, and so forth. Desirably, the receptor is positively charged, naturally as in the case of avidin, or is made so, by the addition of a positively charged moiety or moieties, such as ammonium groups, basic amino acids, etc. Avidin binds to the biotin attached to the detection probe and its degradation products. Avidin is positively charged, while the cleaved electrophoretic tag is negatively charged. Thus the separation of the cleaved electrophoretic tag from, not only uncleaved probe, but also its degradation products, is easily achieved by using conventional separation methods. Alternatively, the receptor may be bound to a solid support or high molecular weight macromolecule, such as a vessel wall, particles, e.g., magnetic particles, cellulose, agarose, etc., and separated by physical separation or centrifugation, dialysis, etc. This method further enhances the specificity of the assay and allows for a higher degree of multiplexing.

As a general matter, one may have two ligands, if the nature of the polypeptide-binding moiety permits. As described above, one ligand can be used for sequestering e-tag moieties bound to the polypeptide-binding region, retaining the first ligand from products lacking the first ligand. Isolation and concentration of the e-tag moieties bound to a modified polypeptide-binding region lacking the first ligand would then be performed. In using the two ligands, one would first combine the reaction mixture with a first receptor for the first ligand for removing polypeptide-binding region retaining the first ligand. One could either separate the first receptor from the composition or the first receptor would be retained in the composition, as described. This would be followed by combining the resulting composition, where the polypeptide-binding region containing the first ligand is bound to the first receptor, with the second receptor, which would serve to isolate or enrich for modified polypeptide-binding region lacking the first ligand, but retaining the second ligand. The second ligand could be the detectable label; a small molecule for which a receptor is available, e.g., a hapten, or a portion of the e-tag probe could serve as the second ligand. After the product is isolated or enriched, the e-tag reporter could be released by denaturation of the receptor, displacement of the product, high salt concentrations and/or organic solvents, etc.

Depending upon the reagent to which the e-tag moiety is attached as discussed above, there may be a single e-tag moiety or a plurality of e-tag moieties, generally ranging from about 1 to about $10^5$, more usually ranging from about 1 to about 300, more particularly ranging from about 1 to about 20 depending on whether or not a hub or particle is employed. The number of e-tag moieties bonded to a single target-binding region depends upon the sensitivity required, the solubility of the e-tag moiety, the effect on the assay of a plurality of e-tag moieties, and the like.

Synthesis of e-tag Probes

The chemistry for performing the types of syntheses to form the charge-imparting moiety or mobility modifier as a peptide chain is well known in the art. See, for example, Marglin, et al., Ann. Rev. Biochem. (1970) 39:841–866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, J. Am. Chem. Soc. (1980) 85:2149–2154 and Houghten et al., Int. J. Pep. Prot. Res. (1980) 16:311–320. The peptide is then removed from the resin according to known techniques.

A summary of the many techniques available for the synthesis of peptides may be found in J. M. Stewart, et al., "Solid Phase Peptide Synthesis", W. H. Freeman Co, San Francisco (1969); and J. Meienhofer, "Hormonal Proteins and Peptides", (1973), vol. 2, p. 46, Academic Press (New York), for solid phase peptide synthesis; and E. Schroder, et al., "The Peptides", vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

For synthesis of e-tag probes employing phosphoramidite, or related, chemistry many guides are available in the literature: Handbook of Molecular Probes and Research Products, 8$^{th}$ edition (Molecular Probes, Inc., Eugene, Oreg., 2002); Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. No. 4,415,732; 4,458,066; and 4,973,679; and the like. Many of these chemistries allow components of the electrophoretic probe to be conveniently synthesized on an automated DNA synthesizer, e.g. an Applied Biosystems, Inc. (Foster City, Calif.) model 392 or 394 DNA/RNA Synthesizer, or the like.

Synthesis of e-tag reagents comprising nucleotides as part of the mobility-modifying moiety can be easily and effectively achieved via assembly on a solid phase support using standard phosphoramidite chemistries. The resulting mobility modifying moiety may be linked to the label and/or polypeptide-binding moiety as discussed above.

The aforementioned label conjugates with different electrophoretic mobility permit a multiplexed detection of multiple polypeptides having induced binding sites. It is, of course, within the purview of the present invention to prepare any number of label conjugates for performing multiplexed determinations.

Exemplary Synthetic Approaches for
Electrophoretic Tags

Figure 2:
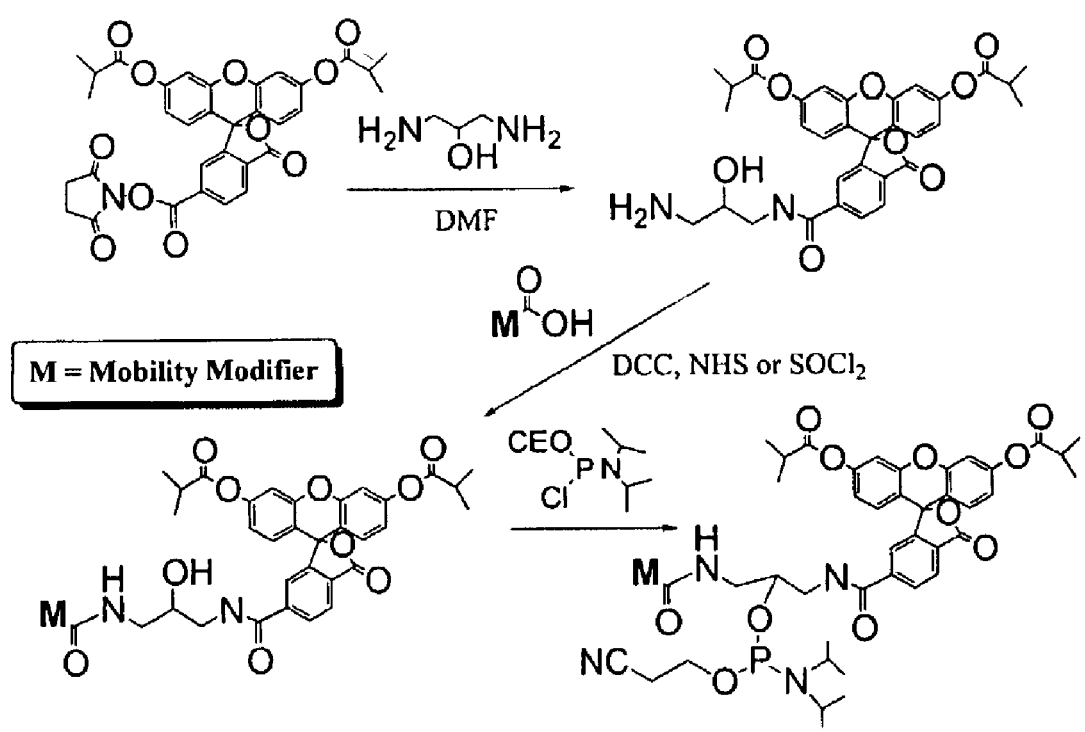
FIG. 2 illustrates the use of a symmetrical bis-amino alcohol linker as the amino alcohol with the second amine then coupled with a multitude of carboxylic acid derivatives.
Figure 3:
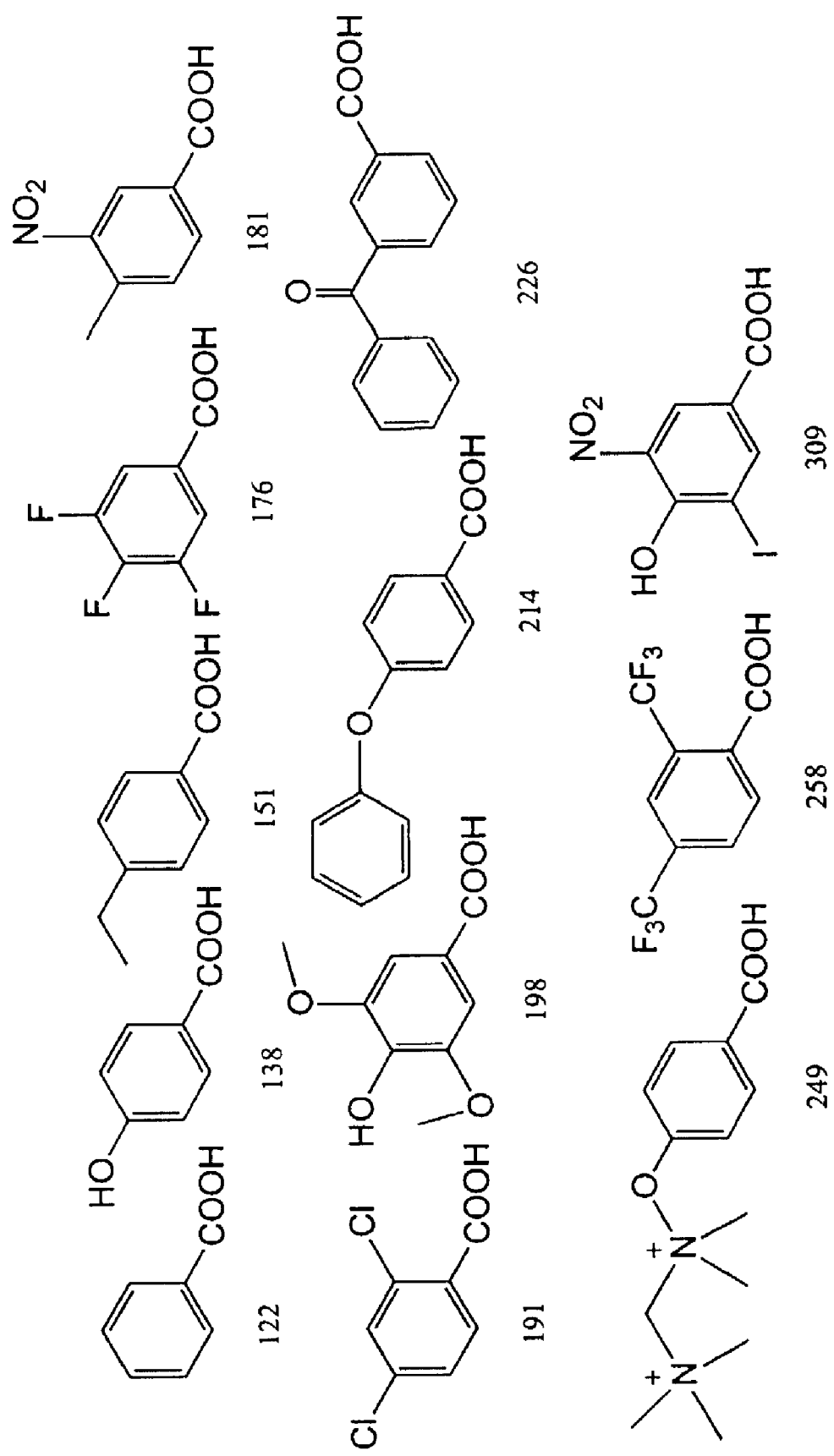
FIG. 3 shows the structure of several benzoic acid derivatives that can serve as mobility modifiers.

One exemplary synthetic approach is outlined in FIG. 1. Starting with commercially available 6-carboxy fluorescein, the phenolic hydroxyl groups are protected using an anhydride. Isobutyric anhydride in pyridine was employed but other variants are equally suitable. It is important to note the significance of choosing an ester functionality as the protecting group. This species remains intact throughout the phosphoramidite monomer synthesis as well as during oligonucleotide construction. These groups are not removed until the synthesized oligo is deprotected using ammonia. After protection the crude material is then activated in situ via formation of an N-hydroxy succinimide ester (NHS-ester) using DCC as a coupling agent. The DCU byproduct is filtered away and an amino alcohol is added. Many amino alcohols are commercially available some of which are derived from reduction of amino acids. Only the amine is reactive enough to displace N-hydroxy succinimide. Upon standard extractive workup, a 95% yield of product is obtained. This material is phosphitylated to generate the phosphoramidite monomer. For the synthesis of additional e-tag moieties, a symmetrical bis-amino alcohol linker is used as the amino alcohol (FIG. 2). As such, the second amine is then coupled with a multitude of carboxylic acid derivatives (exemplified by several possible benzoic acid derivatives shown in FIG. 3) prior to the phosphitylation reaction. Using this methodology hundreds, even thousands of e-tag moieties with varying charge-to-mass ratios can easily be assembled during probe synthesis on a DNA synthesizer using standard chemistries.

Figure 4:
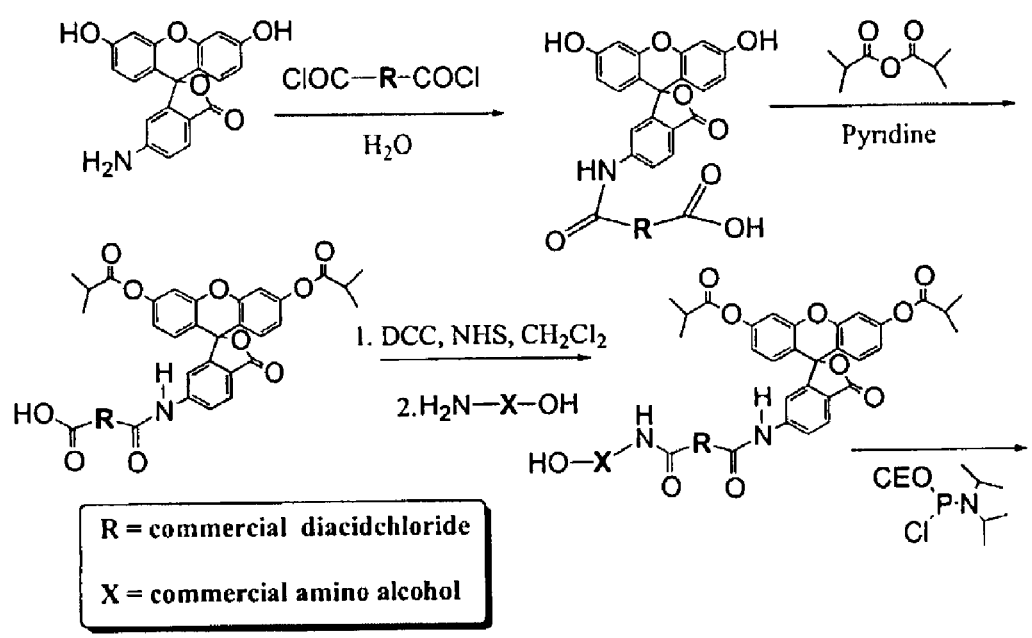
FIG. 4 illustrates the use of an alternative strategy that uses 5-aminofluorescein as starting material and the same series of steps to convert it to its protected phosphoramidite monomer.
Figure 5:
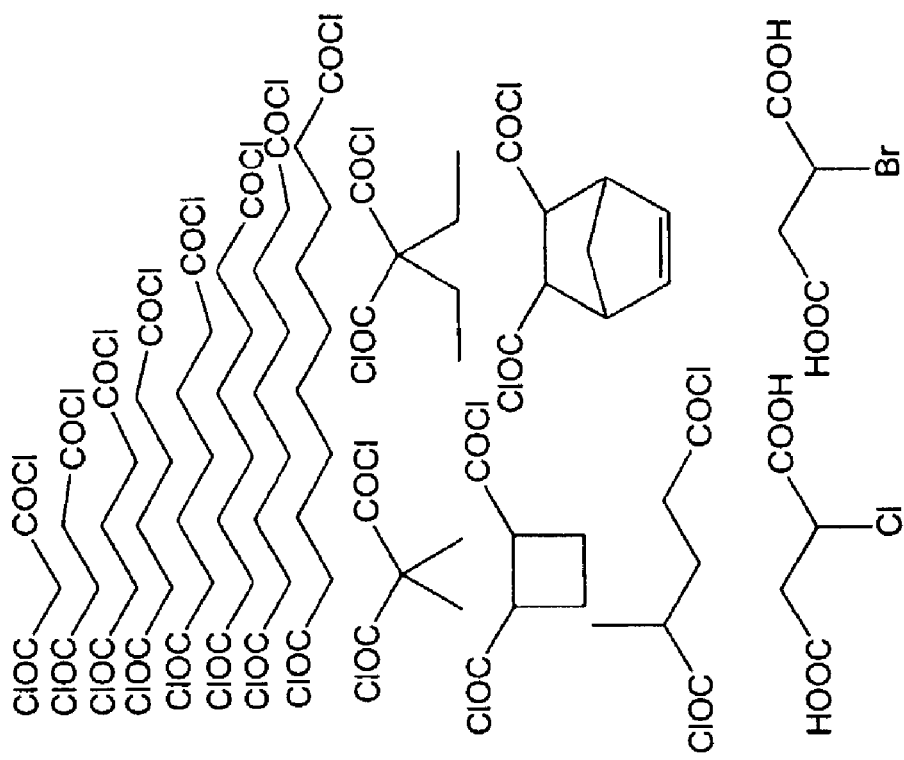
FIG. 5 illustrates several mobility modifiers that can be used for conversion of amino dyes into e-tag phosphoramidite monomers.
Figure 5:
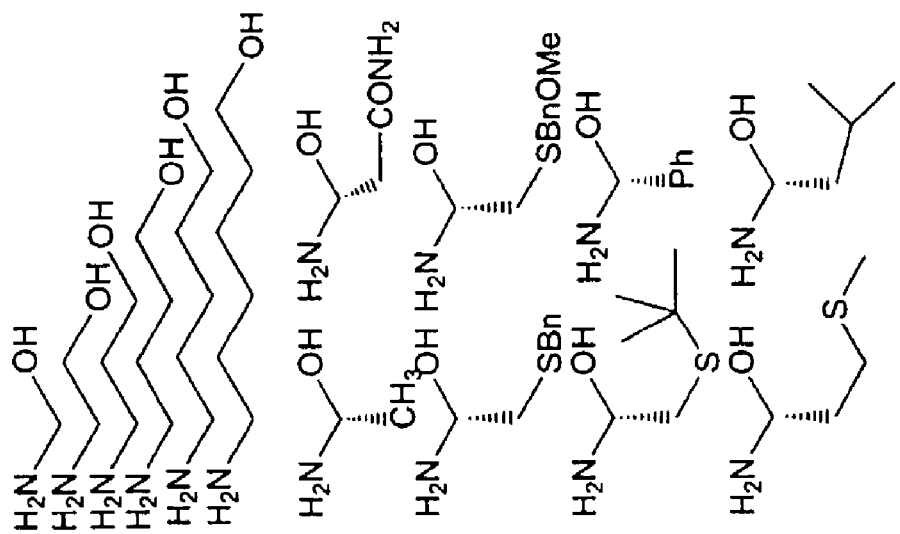
Figure 6:
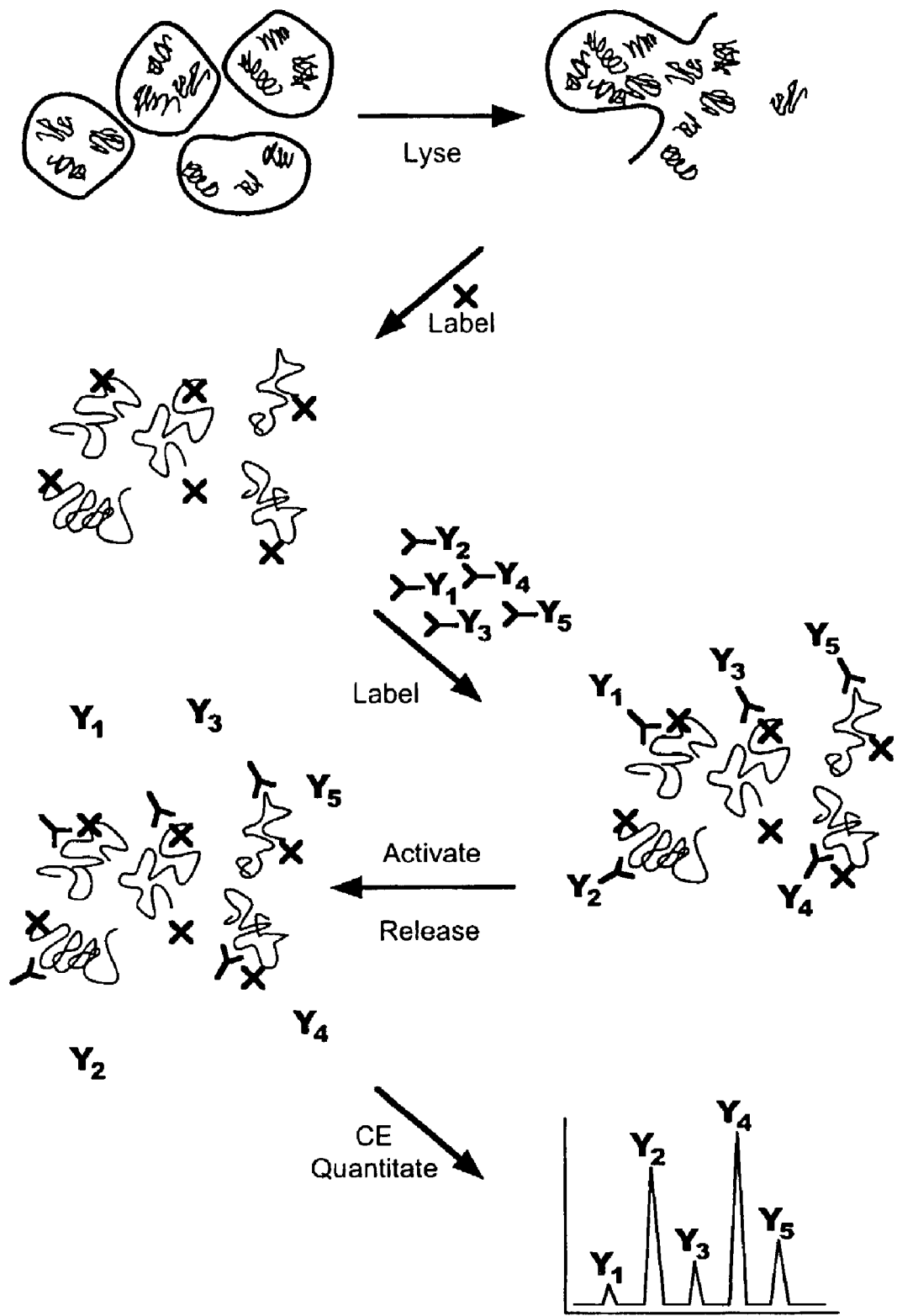
FIG. 6 illustrates use of the present invention for proteomic studies.

Alternatively, e-tag moieties are accessed via an alternative strategy that uses 5-aminofluorescein as starting material (FIG. 4). Addition of 5-aminofluorescein to a great excess of a diacid dichloride in a large volume of solvent allows for the predominant formation of the monoacylated product over dimer formation. The phenolic groups are not reactive under these conditions. Aqueous workup converts the terminal acid chloride to a carboxylic acid. This product is analogous to 6-carboxyfluorescein, and using the same series of steps is converted to its protected phosphoramidite monomer. There are many commercially available diacid dichlorides and diacids, which can be converted to diacid dichlorides using $SOCl_2$ or acetyl chloride. This methodology is highly attractive in that a second mobility modifier is used. As such, if one has access to 10 commercial modified phosphoramidites and 10 diacid dichlorides and 10 amino alcohols there is a potential for 1000 different e-tag moieties. There are many commercial diacid dichlorides and amino alcohols (FIG. 5). These synthetic approaches are ideally suited for combinatorial chemistry.

The e-tag moiety may be assembled having an appropriate functionality at one end for linking to the polypeptide-binding moieties. A variety of functionalities can be employed. Thus, the functionalities normally present in a peptide, such as carboxy, amino, hydroxy and thiol may be the targets of a reactive functionality for forming a covalent bond. The e-tag moieties will be linked in accordance with the chemistry of the linking group and the availability of functionalities on the polypeptide-binding moiety. For example, as discussed above for antibodies, and fragments thereof such as Fab' fragments, specific for a polypeptide, a thiol group will be available for using an active olefin, e.g., maleimide, for thioether formation. Where lysines are available, one may use activated esters capable of reacting in water, such as nitrophenyl esters or pentafluorophenyl esters, or mixed anhydrides as with carbodiimide and half-ester carbonic acid. There is ample chemistry for conjugation in the literature, so that for each specific situation, there is ample precedent in the literature for the conjugation.

In an illustrative synthesis a diol is employed. Examples of such diols include an alkylene diol, polyalkylene diol, with alkylene of from 2 to 3 carbon atoms, alkylene amine or poly(alkylene amine) diol, where the alkylenes are of from 2 to 3 carbon atoms and the nitrogens are substituted, for example, with blocking groups or alkyl groups of from 1–6 carbon atoms, where one diol is blocked with a conventional protecting group, such as a dimethyltrityl group. This group can serve as the mass-modifying region and with the amino groups as the charge-modifying region as well. If desired, the mass modifier can be assembled by using building blocks that are joined through phosphoramidite chemistry. In this way the charge modifier can be interspersed between the mass modifier. For example, a series of polyethylene oxide molecules having 1, 2, 3, n units may be prepared. To introduce a number of negative charges, a small polyethylene oxide unit may be employed. The mass and charge-modifying region may be built up by having a plurality of the polyethylene oxide units joined by phosphate units. Alternatively, by employing a large spacer, fewer phosphate groups would be present, so that without large mass differences, large differences in mass-to-charge ratios may be realized.

The chemistry that is employed is the conventional chemistry used in oligonucleotide synthesis, where building blocks other than nucleotides are used, but the reaction is the conventional phosphoramidite chemistry and the blocking group is the conventional dimethoxytrityl group. Of course, other chemistries compatible with automated synthesizers can also be used. However, it is desirable to minimize the complexity of the process.

As mentioned above, in one embodiment the hub nucleus is a hydrophilic polymer, generally, an addition or condensation polymer with multiple functionality to permit the attachment of multiple moieties. One class of polymers that is useful for the reagents of the present invention comprises the polysaccharide polymers such as dextrans, sepharose, polyribose, polyxylose, and the like. For example, the hub may be dextran to which multiple e-tag reporters may be attached in a cleavable manner consistent with the present invention. A few of the aldehyde moieties of the dextran remain and may be used to attach the dextran molecules to amine groups on an oligonucleotide by reductive amination. In another example using dextran as the hub nucleus, the dextran may be capped with succinic anhydride and the resulting material may be linked to amine-containing oligonucleotides by means of amide formation.

Besides the nature of the linker and mobility-modifying moiety, as already indicated, diversity can be achieved by the chemical and optical characteristics of the fluorescer, the use of energy transfer complexes, variation in the chemical nature of the linker, which affects mobility, such as folding, interaction with the solvent and ions in the solvent, and the like. As already suggested, in one embodiment the linker is an oligomer, where the linker may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality, which may be differentially functionalized. By using protective groups, one can distinguish a side-chain functionality from a terminal amino acid functionality. Also, by appropriate design, one may provide for preferential reaction between the same functionalities present at different sites on the linking group. Whether one uses synthesis or cloning for preparation of oligopeptides, will to a substantial degree depend on the length of the linker.

For 20 different e-tag reporters, only 5 different mass-modifying regions, one cleavable link and four different detectable regions are necessary. For 120 e-tag reporters, one need only have 10 different mass-modifying regions, 3 different charge-modifying regions and 4 different detectable regions. For 500 different e-tag reporters, one need only have 25 different mass-modifying regions, 5 different charge-modifying regions and 4 different detectable regions.

Methods for Use of e-tag Reagents

The following general discussion of methods and examples of specific assays are by way of illustration and not limitation. One skilled in the art will be able to apply the technology herein in assaying for any analytes in most assay formats that will be apparent to the skilled artisan particularly protein assays and the area of chemical genetics.

In carrying out the assays, the components, i.e., the sample, the first reagent and the second reagents, are combined in an assay medium in any order, usually simultaneously. Alternatively, one or more of the reagents may be combined with one or more of the remaining agents to form a subcombination. The subcombination can then be subjected to incubation. Then, the remaining reagents or subcombination thereof may be combined and the mixture incubated. The amounts of the reagents are usually determined empirically. As a general rule, at least an equal amount of the first reagent and the second reagent is employed to the highest expected amount of the polypeptides of interest, usually at least about 1.5 fold excess, more usually at least about 2 fold excess and may have about 10 fold excess or more. The components are combined under binding conditions, usually in an aqueous medium, generally at a pH in the range of about 5 to about 10, with buffer at a concentration in the range of about 10 to about 200 mM. These conditions are conventional, where conventional buffers may be used, such as phosphate, carbonate, HEPES, MOPS, Tris, borate, etc., as well as other conventional additives, such as salts, stabilizers, organic solvents, etc. The aqueous medium may be solely water or may include from 0.01 to 80 or more volume percent of a co-solvent.

The combined reagents are incubated for a time and at a temperature that permit a substantial number of binding events to occur. Generally, the time for incubation after combination of all or a portion of the reagents is at least about 5 min, more usually at least about 15 min, before irradiating the mixture or adding the remaining reagents. Moderate temperatures are normally employed for the incubation and usually constant temperature. Incubation temperatures will normally range from about 5° to 99° C, usually from about 15° to 70° C, more usually 20 to 45° C. Temperatures during measurements will generally range from about 10° to 70° C, more usually from about 20° to 45° C, more usually 200 to 25° C.

After the appropriate incubation periods and after all of the reagents have been combined to form a combination comprising the first reagent or cleavage-inducing reagent, the sample and the second reagent or e-tag probe, the mixture is treated to activate the cleavage-inducing moiety. The nature of the activation is, of course, dependent on the nature of the cleavage-inducing moiety.

The subject invention employs a variety of reagent systems, where a binding event results in release of an e-tag moiety. The effect of the cleavage-inducing moiety is to make or break a bond by physical, chemical or enzymatic means. Each of the products of the different second reagents or e-tag probes containing polypeptide-binding regions can be accurately detected, so as to determine the occurrence of the binding event involving the induced binding site. Following the binding event, one or more reaction products are produced that exhibit mobilities different from the e-tag probe or probes from which the reaction products derive. The released form of the e-tag, termed the e-tag reporter, exhibits a different mobility and/or mass than the e-tag probe from which it derives. The invention offers a high degree of versatility for screening known and unknown materials. An electrophoretic device may be employed for separation and detection of the e-tag reporter. The electrophoretic device may be connected to a data processor for receiving and processing data from the device, as well as operating the electrophoretic device.

The systems are based on having libraries available comprising a plurality of e-tag reagents that comprise at least a plurality of different mobility-modifying moieties, so as to be separable by electrophoresis with the entities to which the mobility-modifying moieties are attached. The mobility-modifying moieties are retained in the product of the reaction, where the product is modified by the gain and/or loss of a group that changes the mass and may also change the charge of the product, as compared to the starting material. The mobility-modifying moiety is joined to a polypeptide-binding region by a cleavable bond, so that the mobility-modifying moiety is released for analysis subsequent to the binding of the induced binding site to the first binding agent.

In addition, in many heterogeneous assays it is required that the unbound labeled reagent be separable from the bound labeled reagent. This can be achieved in a variety of ways, each requiring a reagent bound to a solid support that distinguishes between the complex of labeled reagent and polypeptide. The solid support may be a vessel wall, e.g., microtiter well plate well, capillary, plate, slide, beads, including magnetic beads, liposomes, or the like. The primary characteristics of the solid support is that it permits segregation of the bound labeled specific binding member from unbound probe and that the support does not interfere with the formation of the binding complex, nor the other operations of the determination.

The solid support may have the complex directly or indirectly bound to the support. For directly bound, one may have the first reagent or e-tag probe covalently or non-covalently bound to the support. The surface may be activated with various functionalities that will form covalent bonds with the first reagent. These groups may include imino halides, activated carboxyl groups, e.g., mixed anhydrides or acyl halides, amino groups, α-halo or pseudohaloketones, etc. A specific binding member bound to the surface of the support may be used to bind a member of the complex.

Usually, in a heterogeneous mode, the unbound labeled reagent or e-tag probe will be removed by washing the bound material. Where particles or beads are employed, these may be separated from the supernatant before washing, by filtration, centrifugation, magnetic separation, etc. After washing, the support may be combined with a liquid into which the e-tag reporters are to be released and/or the functionality of the e-tag moieties is reacted with the detectable label, followed by or preceded by release. Depending on the nature of the cleavable bond and the method of cleavage, the liquid may include any additional reagents for the cleavage. Where reagents for cleavage are not required, the liquid is conveniently an electrophoretic buffer. For example, where the cleavable linkage is photolabile, the medium may be irradiated with light of appropriate wavelength to release the e-tag reporters. Where detectable labels are not present on the e-tag moieties, the e-tag reporters may be reacted with detectable labels. In some instances the detectable label may be part of the reagent cleaving the cleavable bond, e.g., a disulfide with a thiol. Where there is a plurality of different functionalities on different binding members for reaction with the label, the different labels have functionalities that react with one of the functionalities. The different labels may be added together or individually in a sequential manner. For example, where the functionalities involve thiols, carboxyl groups, aldehydes and olefins, the labels could have activated olefins, alcohols, amines and thiol groups, respectively. By having removable protective groups for one or more of the functionalities, the protective groups may be removed stepwise and the labels added stepwise. In this way cross-reactivity may be avoided. Whether one has the detectable label present initially or one adds the detectable label is not critical to this invention and is frequently governed by whether the polypeptide itself is cleaved by the cleavage-inducing moiety or by the nature of the polypeptides and the first and second reagents.

In some embodiments, the e-tag reporters may be required to be separated from the reagent solution, where the reagent interferes with the electrophoretic analysis. Depending on the nature of the e-tag reporters and the reagent, one may sequester the e-tag reporters from the reagent by using ion exchange columns, liquid chromatography, an initial electrophoretic separation, and the like. Alternatively, as discussed previously, one may have a capture ligand bound to the e-tag moiety or retained portion of the target-binding region for isolating the e-tag reporter, so as to remove any interfering components in the mixture. Once the solution of e-tag reporters is prepared and free of any interfering components, the solution may be analyzed electrophoretically. The analysis may employ capillary electrophoresis devices, microfluidic devices or other devices that can separate a plurality of compounds electrophoretically, providing resolved bands of the individual e-tag reporters.

Preferably, the assays in accordance with the present invention are carried out in a homogeneous manner. The protocols for the subject homogeneous assays generally follow the procedures for the analogous heterogeneous assays. These protocols employ a signal producing system that includes the label of the e-tag probe, the cleavable bond associated with the e-tag probe or the polypeptide as the case may be, electromagnetic radiation or other reagents involved in the reaction or for diminishing background signal. In assays involving the production of singlet oxygen, it may be desirable to have a molecule in solution that degrades hydrogen peroxide to reduce its lifetime, in order to prevent reaction between hydrogen peroxide produced by a bound and unbound label-containing reagent.

Generally, the concentrations of the various agents involved with the signal producing system will vary with the concentration range of the individual polypeptides in the samples to be analyzed, generally being in the range of about 10 nM to about 10 mM. Buffers will ordinarily be employed at a concentration in the range of about 10 to about 200 mM. The concentration of each polypeptide will generally be in the range of about 1 pM to about 100 μM, more usually in the range of about 100 pM to about 10 μM. In specific situations the concentrations may be higher or lower, depending on the nature of the analyte, the affinity of the reciprocal binding members, the efficiency of release of the e-tag reporters, the sensitivity with which the e-tag reporters are detected, and the number of polypeptides, as well as other considerations.

In accordance with one aspect of the invention, a group of polypeptides may be monitored in a multiplexed reaction. In this case, a plurality of pairs of e-tag probes corresponding to the various polypeptides are combined with a sample in a single reaction vessel under conditions where the e-tag reporter is released from the reagent when a respective polypeptide binds to a binding agent and the medium is treated to generate singlet oxygen. The e-tag reporters are either labeled for detection or the label is added by means of a reactive functionality present on the e-tag moiety. The labeled e-tag reporters of the reaction are resolved from one another on the electrophoretic device, and again are monitored as they move past the detector. The level of multiplexing possible in this system is limited only by the degree of resolution that can be obtained between a designated set of e-tag reporters on the electrophoretic device.

An additional degree of flexibility can be conferred on the assay by the stage at which the e-tag moieties are labeled. As described above, each e-tag moiety may already contain a detectable label when introduced into the reaction. Alternatively, an e-tag moiety may contain a functionality allowing it to bind to a label after reaction with the sample is complete. In this embodiment, an e-tag probe comprising a functionality for binding to a detectable label is combined with a sample. After a reaction to modify the mobility of the e-tag probe if its target polypeptide is present in the sample, additional reagents are combined in a sample vessel with the products of the first reaction, which reacts with the modified e-tag reporter(s) to add a detectable label.

For quantitation, one may choose to use controls, which provide a signal in relation to the amount of the target that is present or is introduced. A control to allow conversion of relative fluorescent signals into absolute quantities is accomplished by addition of a known quantity of a fluorophore to each sample before separation of the e-tag reporters by electrophoresis. Any fluorophore that does not interfere with detection of the e-tag reporter signals can be used for normalizing the fluorescent signal. The control signal will preferably have an electrophoretic mobility that is different from that of any of the e-tag reporters in the sample, and could have the same or a different emission wavelength. Exemplary fluorescent molecules include ROX, FAM, and fluorescein.

An assay in accordance with the present invention involves the detection of the phosphorylation of a polypeptide. The sample comprises cellular material and the post-translational modification is the phosphorylation of a particular polypeptide, referred to as a target polypeptide. The sample is combined with a first reagent comprising a photosensitizer linked to an IMAC resin to which is bound a metal ion. If the phosphorylated target polypeptide is present, the phosphate group binds to the metal chelaor attached to the IMAC resin. One or more electrophoretic probes are combined with the above reaction mixture. Preferably, each electrophoretic probe comprises an antibody for the target polypeptide, to which is cleavably linked an e-tag reporter. The cleavable link comprises a moiety that is cleavable by singlet oxygen. After addition of the second reagent and an appropriate incubation period, the reaction mixture is irradiated with light to excite the photosensitizer, which generates singlet oxygen. The cleavable moiety is cleaved by the singlet oxygen because the cleavable moiety is in close proximity to the photosensitizer and the active species, namely, singlet oxygen, retains sufficient activity to cleave the cleavable moiety and release e-tag reporter. Second reagent that does not become bound to target polypeptide because the target polypeptide is not present, or excess second reagent, or second reagent that binds to a polypeptide that is not phosphorylated, does not yield cleaved e-tag reporters because the activity of the singlet oxygen is very short-lived and the cleavable moiety in any second reagent that is not bound to the first reagent by virtue of the presence of phosphorylated target polypeptide does not yield cleaved e-tag reporters. The released e-tag reporter is separated on the basis of its different mobility and detected on the basis of the detection moiety that remains attached to the mobility modifying moiety of the e-tag reporter. The presence and/or amount of the released e-tag reporter indicates the presence and/or amount of the target polypeptide.

The present invention finds particular use in multiplexed assays for target polypeptides. An example of an assay in accordance with this aspect of the present invention involves the detection of the phosphorylation of multiple polypeptides. The sample comprises cellular material and the post-translational modification is the phosphorylation of several polypeptides, referred to as target polypeptides. The sample is combined with a first reagent comprising a photosensitizer linked to a metal affinity agent to which is bound a metal ion. The first reagent is a class-specific reagent in that it binds to any phosphate group present in the reaction mixture. If the phosphorylated target polypeptides are present, the phosphate group binds to the metal-metal affinity agent complex. A plurality of second reagents is combined with the above reaction mixture. Each of the second reagents comprises an antibody for a particular target polypeptide, to which is cleavably linked an e-tag reporter that is unique for the particular target polypeptide. The cleavable link comprises a moiety that is cleavable by singlet oxygen. After addition of the second reagents and an appropriate incubation period, the reaction mixture is irradiated with light to excite the photosensitizer, which generates singlet oxygen. The cleavable moiety is cleaved by the singlet oxygen because the cleavable moiety is in close proximity to the photosensitizer and the active species, namely, singlet oxygen, retains sufficient activity to cleave the cleavable moiety and release e-tag reporters from all second reagents that are bound to a target polypeptide bound to the class-specific reagent. Again, second reagents, which do not become bound to target polypeptides bound to the class-specific reagent, do not yield cleaved e-tag reporters for the reasons given above. The released e-tag reporters are separated on the basis of their differences in mobility and detected on the basis of the detection moiety that remains attached to the mobility modifying moiety of the e-tag reporter. The presence and/or amount of each of the released e-tag reporters indicate the presence and/or amount of each of the respective target polypeptides. In this fashion various cellular pathways may be studied on a real time basis. Protein phosphorylation and de-phosphorylation reactions may be studied to develop more information about metabolic regulation and signal transduction pathways. The above method may be repeated at various times during the cell cycle to follow the progression of the cell.

Another application of the present invention is to detect multiple phosphorylations of a target polypeptide. For example, it is desirable to know whether a polypeptide has been mono-phosphorylated, bis-phosphorylated or even higher multiples of phosphorylation. An example of an assay in accordance with this aspect of the present invention involves the detection of the degree of phosphorylation of a target polypeptide. The sample, which comprises cellular material, is combined with a first reagent comprising a multiple photosensitizer molecules linked to a hub molecule to which multiple molecules of a metal affinity agent with bound metal are also linked. By appropriate titration of the class-specific reagent, the level of phosphorylation of the target polypeptide can be determined. If the phosphorylated target polypeptides are present, the phosphate group binds to the metal-metal affinity agent complex. A second reagent is combined with the above reaction mixture. The second reagent comprises an antibody for the particular target polypeptide, to which is cleavably linked an e-tag reporter that is unique for the particular target polypeptide. The cleavable link comprises a moiety that is cleavable by singlet oxygen. After addition of the second reagent and an appropriate incubation period, the reaction mixture is irradiated with light to excite the photosensitizer, which generates singlet oxygen. The cleavable moiety is cleaved by the singlet oxygen because the cleavable moiety is in close proximity to the photosensitizer. The active species, namely, singlet oxygen, retains sufficient activity to cleave the cleavable moiety and release e-tag reporters from the second reagent that is bound to a target polypeptide bound to the class-specific reagent. Again, second reagents, which do not become bound to target polypeptides bound to the class-specific reagent, do not yield cleaved e-tag reporters for the reasons given above. The released e-tag reporter is separated on the basis of differences in mobility and detected on the basis of the detection moiety that remains attached to the mobility modifying moiety of the e-tag reporter. The presence and/or amount of the released e-tag reporter may be correlated with the amount of class-specific reagent added to determine the level of phosphorylation of the target polypeptide.

The present invention may be employed to determine the site or sites of phosphorylation on a target polypeptide. In an example of an assay in accordance with this aspect of the present invention, the sample, which comprises cellular material, is combined with a first reagent comprising a chemical protease linked to a metal affinity agent to which is bound a metal ion. If the phosphorylated target polypeptide is present, the phosphate group binds to the metal-metal affinity agent complex. The chemical protease is activated by irradiation with light and site specific cleavage takes place on the target polypeptide whose phosphate group is bound to the metal affinity-metal complex. The cleavage products represent unique moieties, or e-tag moieties, which may be analyzed directly by electrophoresis, and the like. On the other hand, one or more second reagents may be combined with the above reaction mixture to provide a detection moiety for the unique moieties. Each second reagent comprises an antibody for a cleaved moiety, to which is attached the detection moiety. The unique moiety with attached detection moiety is an e-tag reporter and is separated on the basis of its different mobility and detected on the basis of the detection moiety that is attached to the unique moiety. The presence of the e-tag reporter is indicative of the site of phosphorylation of the target polypeptide.

Mitogen-activated protein kinases (MAPK's) may provide and understanding of cellular events in growth factor and cytokine receptor signaling. The MAP kinases (also referred to as extracellular signal-regulated protein kinases, or ERK's) are the terminal enzymes in a three-kinase cascade. The reiteration of three-kinase cascades for related but distinct signaling pathways gave rise to the concept of a MAPK pathway as a modular, multifunctional signaling element that acts sequentially within one pathway, where each enzyme phosphorylates and thereby activates the next member in the sequence. The recent identification of distinct MAPK cascades that are conserved across all eukaryotes indicates that the MAPK module has been adapted for interpretation of a diverse array of extracellular signals. The MAPK superfamily of enzymes is a critical component of a central switchboard that coordinates incoming signals generated by a variety of extracellular and intracellular mediators. Specific phosphorylation and activation of enzymes in the MAPK module transmits the signal down the cascade, resulting in phosphorylation of many proteins with substantial regulatory functions throughout the cell, including other protein kinases, transcription factors, cytoskeletal proteins and other enzymes. (Cobb, et al., Promega Notes Magazine (1996) 59:37, et seq.)

A particular assay for kinase interactions is illustrative of the many types of assays that can be developed. Specific kinase interactions may be studied using a sandwich assay format. For example, a first anti-kinase antibody is labeled with an e-tag moiety, and a second antibody that binds a phosphorylated molecule, will be labeled with a photosensitizer. After forming the immune complex, the e-tag moiety will be released by illuminating with light at the appropriate wavelength, then separated by capillary electrophoresis. In another format, kinases with varying specificities can be investigated. Anti-kinase antibodies are labeled with the same photosensitizer (e.g., photosensitizer$_1$-anti-kinase$_1$, photosensitizer$_1$-anti-kinase$_2$, photosensitizer$_1$-anti-kinase$_3$, etc.), while specific kinase substrates or inhibitors will be labeled with specific e-tag moieties (e.g., substrate$_1$-e-tag$_1$, substrate$_2$-e-tag$_2$, substrate$_3$-e-tag$_3$, etc.). Binding complexes will be formed, either stably or transiently. After illumination and electrophoretic separation, particular patterns will be generated that are indicative of the various levels of the chosen kinase targets in the sample, determined simultaneously. Once a signal pattern is established, the effects of various drugs, treatments, or genetic alterations can be assessed as alterations to this pattern.

Figure 7:
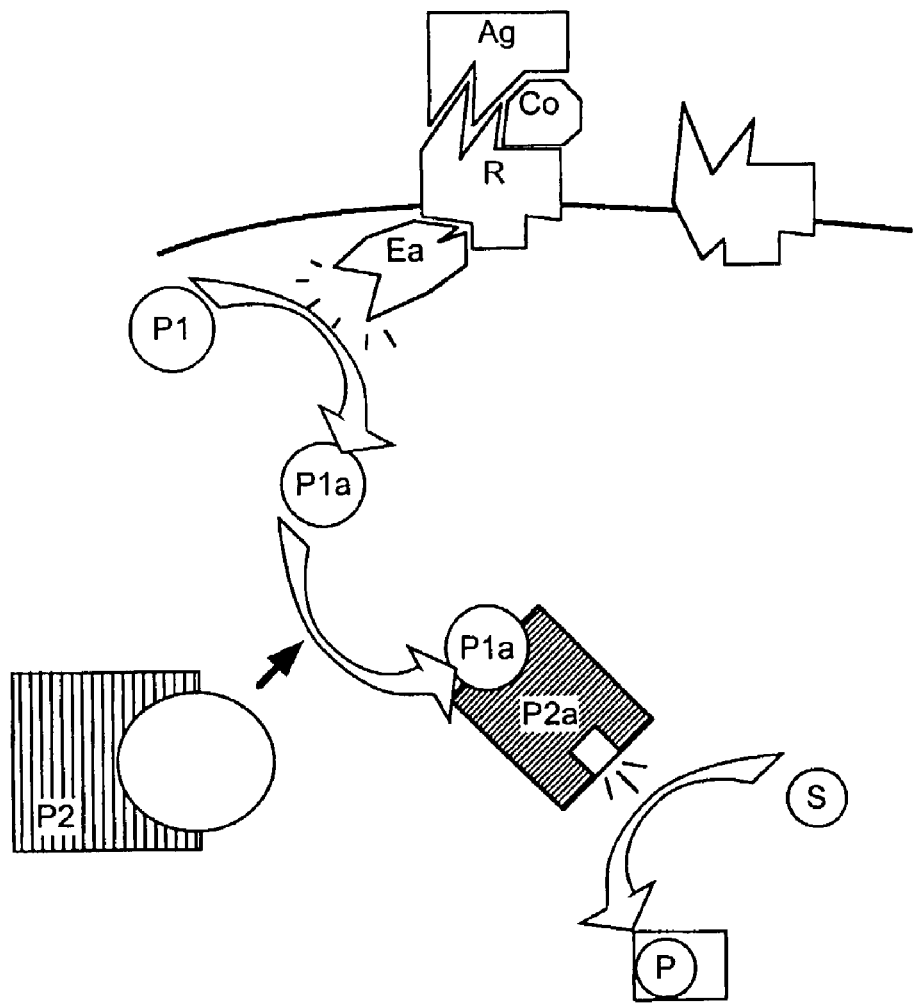
FIG. 7 is a cartoon depicting the use of reagents of the invention to detect the affects of ligand-cell surface receptor interactions.
Figure 7:
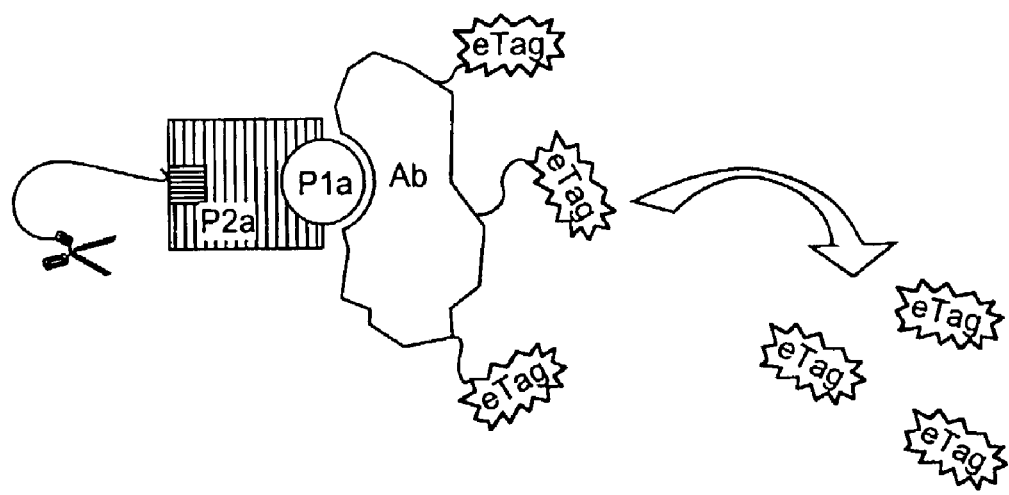

An example of use of the present invention for proteomics is given in FIG. 7. In this embodiment, assays are performed by first lysing a cell sample. All the proteins in the cell lysate are labeled with a cleavage-inducing moiety. The labeling is performed to obtain at least one cleavage-inducing moiety per protein. As shown in FIG. 7, the proteins are interrogated with anti-protein ligand (APL), which can be a receptor or an antibody. The APL's are labeled with specific eTag reporter molecules through a cleavable linkage; each ligand has a unique eTag reporter associated with it. After binding, the cleavage-inducing moieties are activated to release the different reporters (Y). The cleavage-inducing moiety and the cleavable linkage must to be in close proximity for the e-tag reporter to be released. The reporters are then separated via capillary electrophoresis and quantified. The technology enables multiplexed profiling of proteins, small molecules, enzyme-substrates and cell surface receptors in a homogeneous assay format.

Determining the cellular function of a protein generally requires a means to alter the function. One approach is a genetic one that involves the use of inactivating or activating mutations in genes encoding the protein. Inactivation involves deletion or knock-out approaches, and activation or over-expression involves oncogenic approaches. Another approach involves the use of small molecules that alter the function of proteins to which they bind. Ligands exist that are capable of either inactivating or activating protein function. It has been demonstrated that for some natural products, specificity can approach that of a gene knock-out (Schreiber, Bioorganic and Medicinal Chemistry, 6 (1998) 1127–1152; Stockwell, et al., Chemistry and Biology, 6 (1999) 71–83). Small molecule natural products have aided in disentangling the complex web of cell-cycle events in several ways such as, for example, arrests at specific points in the cell cycle allowing synchronization of a population of cells. Once a specific binding interaction is established, a cell-permeable natural product can be used to understand the function of its protein target in living cells. Some natural products inhibit the signal transduction pathway required for the transition from the quiescent state to the G1 transition state. Small molecules can affect post-translational events such as protein glycosylation, methylation, lipidation, isoprenylation, ubiquitination, phosphorylation and acetylation.

Entrance into and exit out of the cell cycle occurs as a cell passes between active proliferation and a quiescent state or G0 state, in which the fundamental metabolism of the cell is depressed, including many of its usually active functions such as transcription and protein synthesis. Deprivation of growth factors can cause a cell to exit into quiescent state, whereas stimulation with growth factors can signal a cell to re-enter the active cycle. A cell may also exit the cell cycle to undergo processes of differentiation or programmed cell death (apoptosis). The element responsible for driving the cell cycle from one phase to the next is a series of protein kinases and phosphatases that activate and deactivate each other. The cyclin-dependent kinases are responsible for phosphorylating various substrates critical to cell-cycle progression. The levels of the cyclin-dependent kinases are invariant throughout the cell cycle, but their activities are modulated by their interaction with another set of proteins called cyclins, whose levels fluctuate. In addition many of the receptors on the plasma membrane of the cell are tyrosine kinases that, upon activation, initiate an intracellular signal transduction pathway whose ultimate end point is cell proliferation.

The methods and reagents of the present invention are well suited for the aforementioned area of analysis. A wide variety of small molecules cause a loss of function of their cognate targets, including kinases, phosphatases, membrane receptors, proteases, isoprenyl transferases and polymerases. As a result of the present invention, protein function may be studied in its intracellular environment. Proteins of interest may be quantitated. The effect on the levels of downstream proteins such as, e.g., cyclins, may be studied using the reagents of the present invention. Active and inactive cyclin-dependent kinases (Cdk's) may be measured along with the expression of cyclins. The Cdk-cyclin complex may also be quantitated. Signal transduction pathways may be studied with the present reagents.

Figure 8:
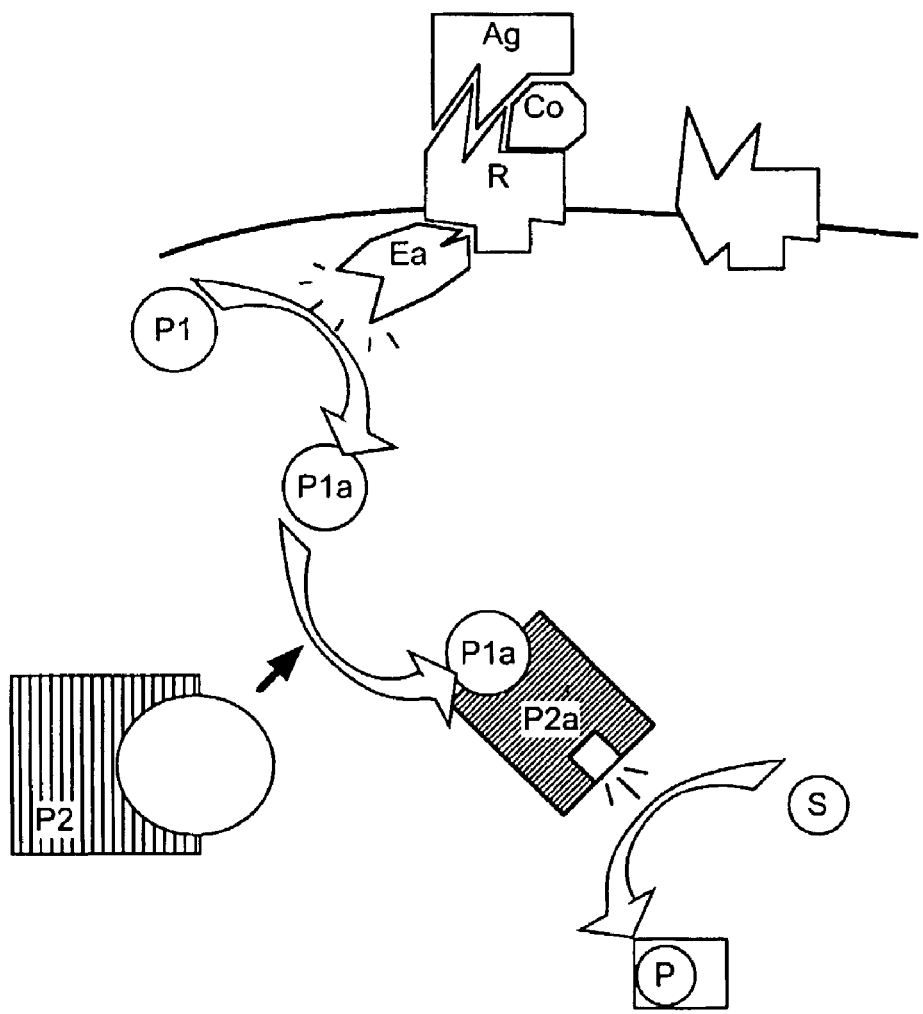
FIG. 8 is a cartoon with a further depiction of the use of reagents of the invention to detect the affects of ligand-cell surface receptor interactions.
Figure 8:
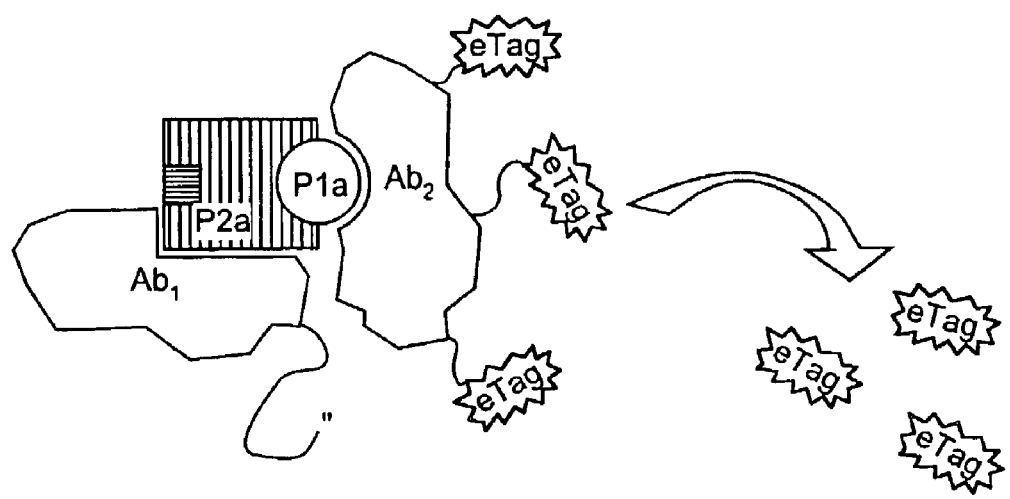
Figure 9A:
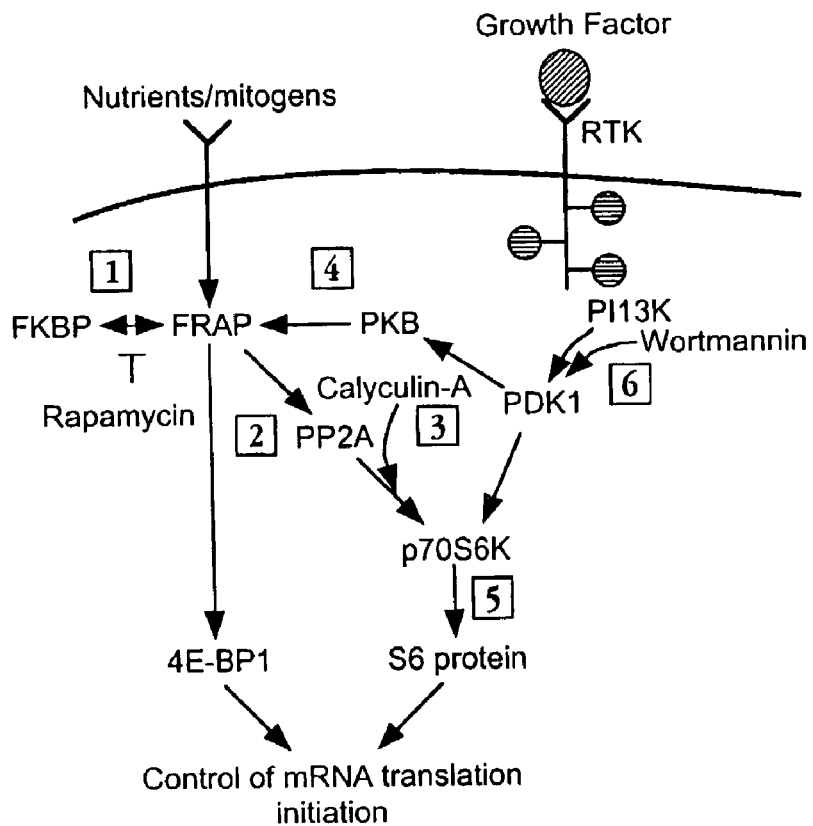
FIG. 9A is a cartoon depicting analysis of protein-protein interactions in a cellular pathway.
Figure 9B:
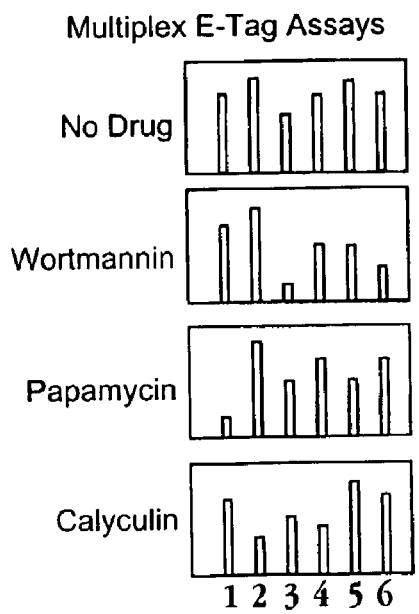
FIG. 9B shows hypothetical results of the effect of drug treatments on six designated protein interactions.
Figure 10:
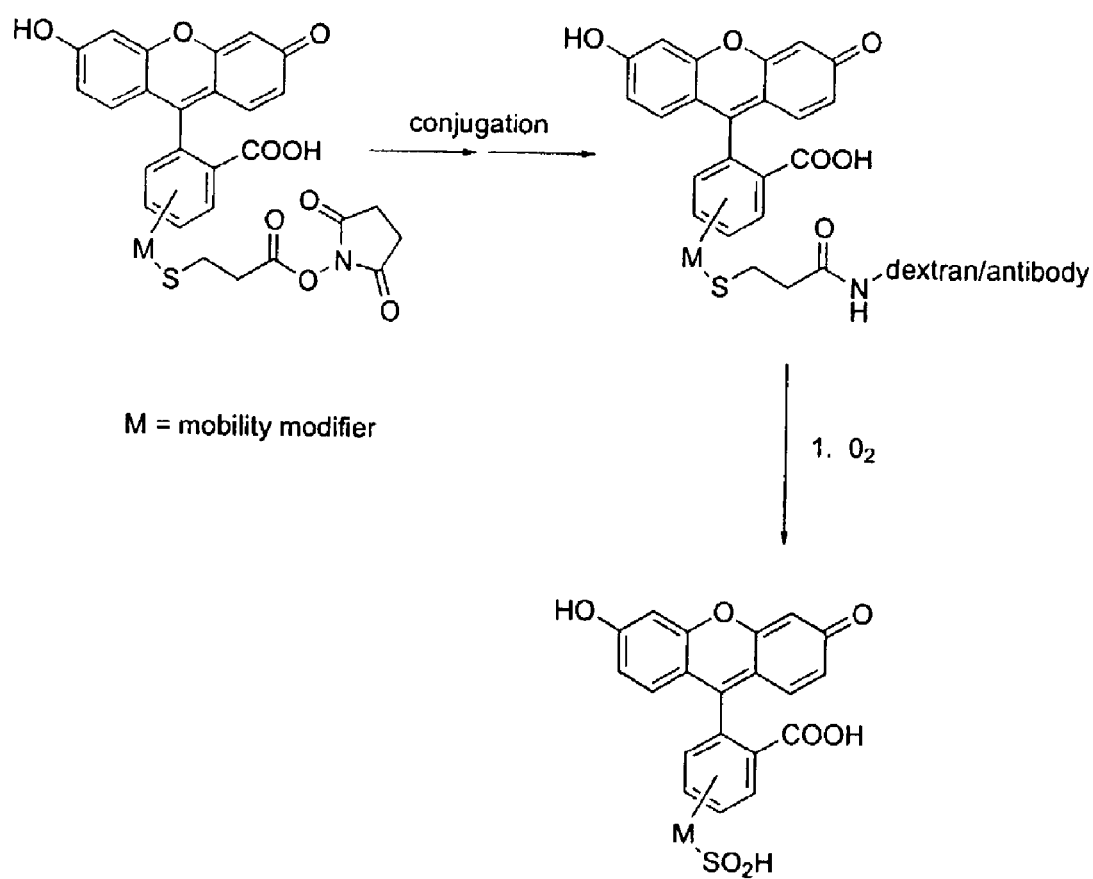
FIG. 10 illustrates the general methodology for conjugation of an e-tag moiety to an antibody to form an e-tag probe, and the reaction of the resulting probe with singlet oxygen to produce a sulfinic acid moiety as the released e-tag reporter.
Figure 11A:
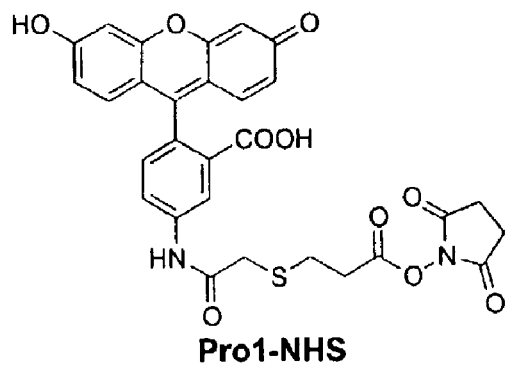
FIG. 11 A–D shows the structures of e-tag moieties that have been designed and synthesized. (Pro1 is commercially available from Molecular Probes, Inc.)
Figure 11A:
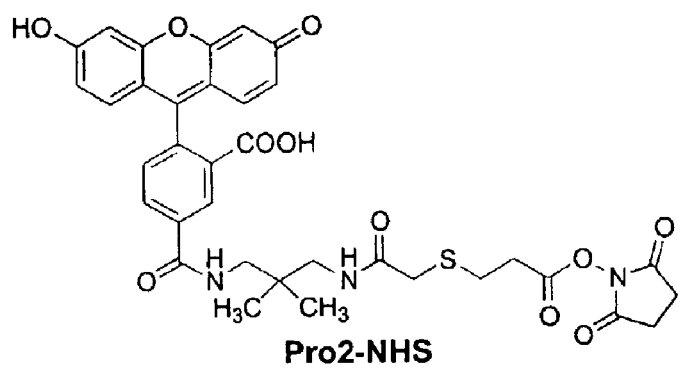
Figure 11A:
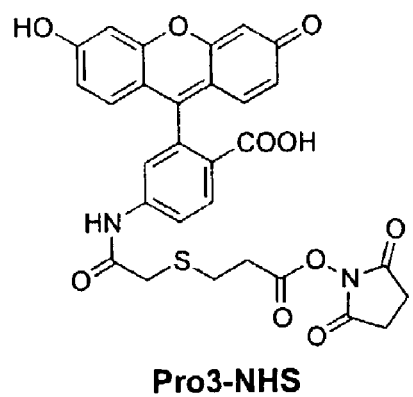
Figure 11A:
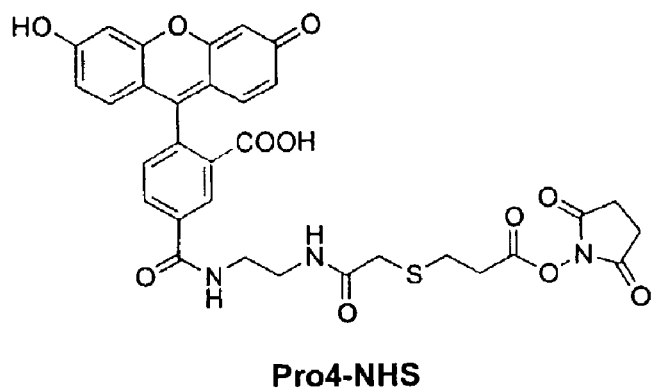
Figure 11B:
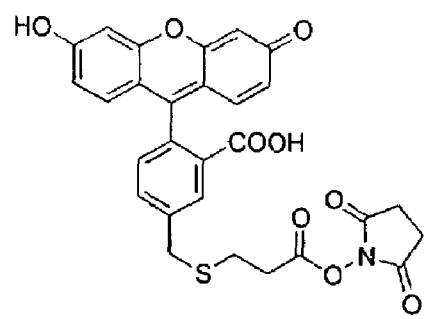
Figure 11B:
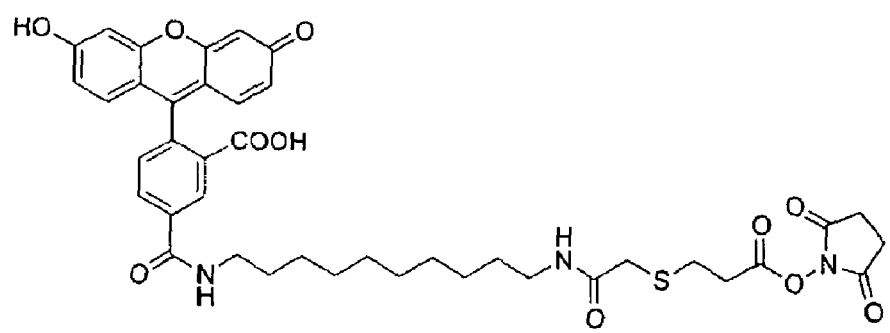
Figure 11B:
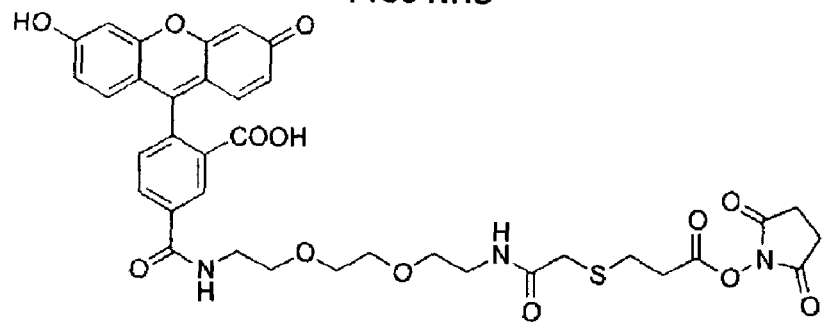
Figure 11B:
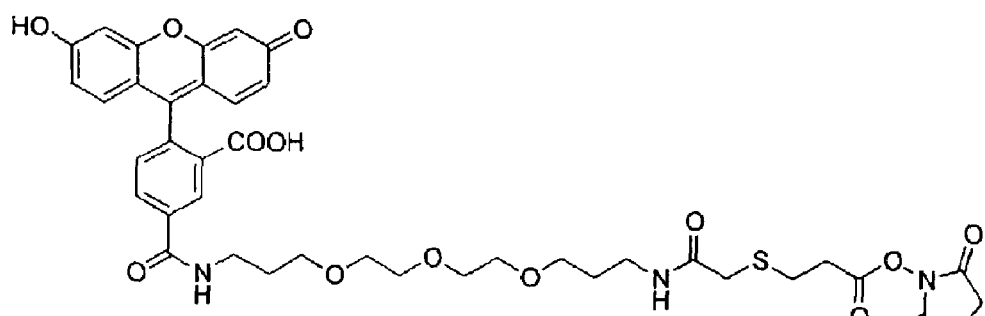
Figure 11C:
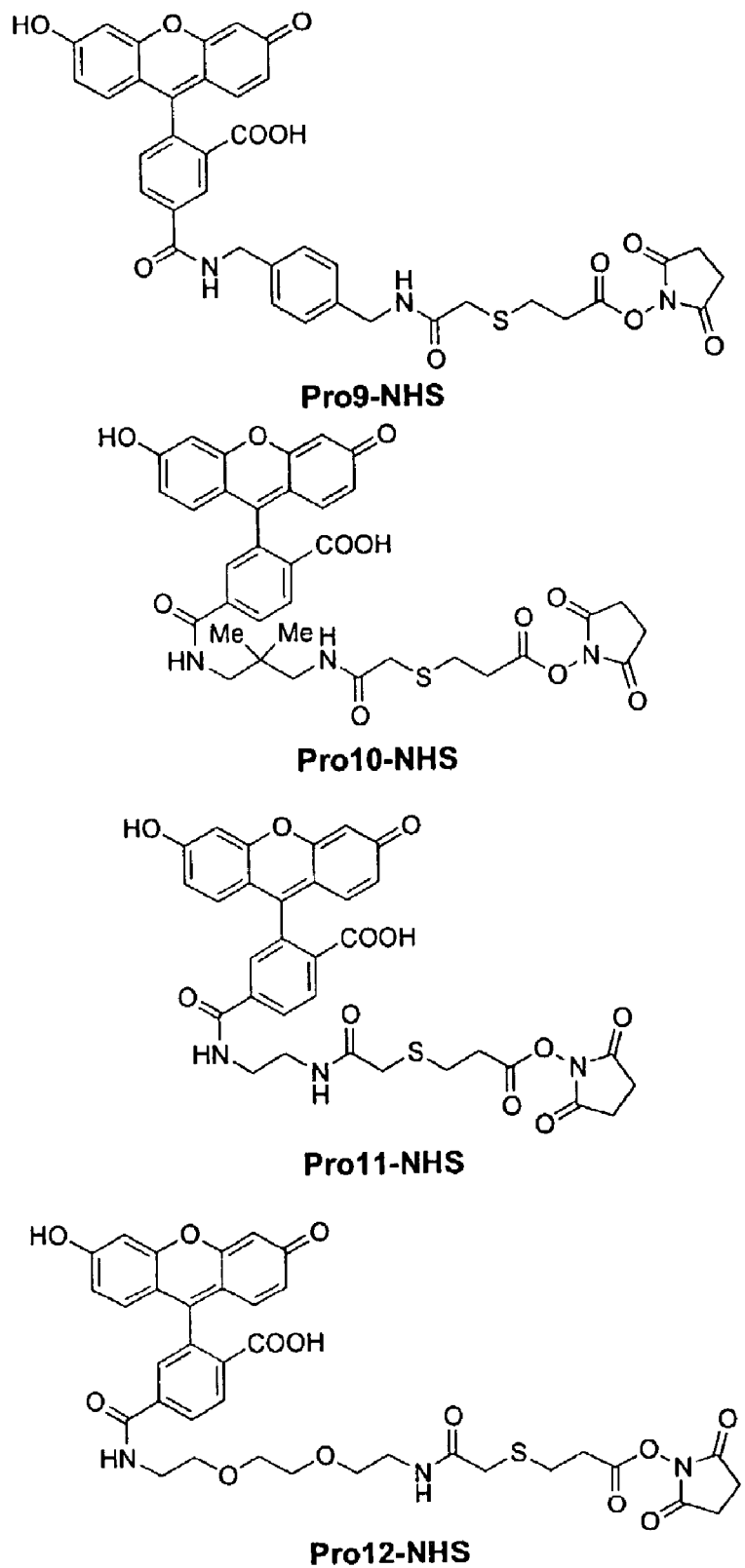
Figure 11D:
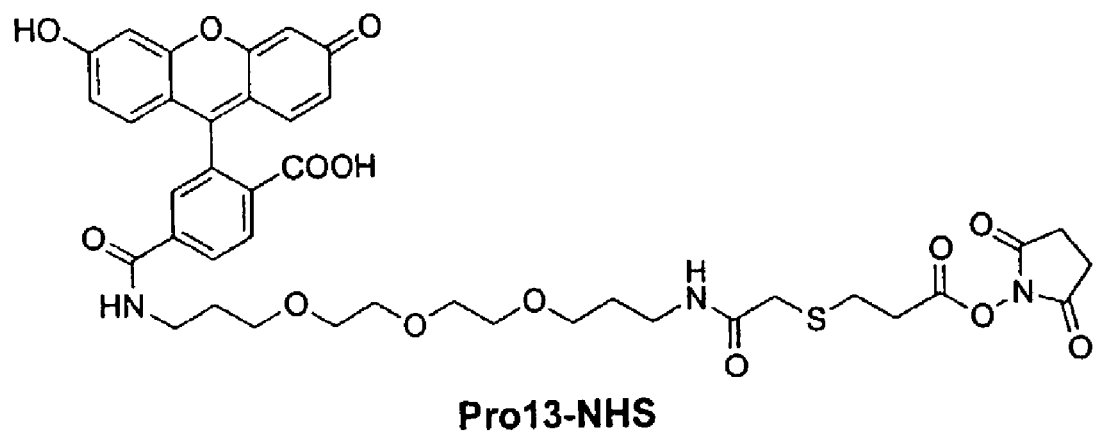
Figure 11D:
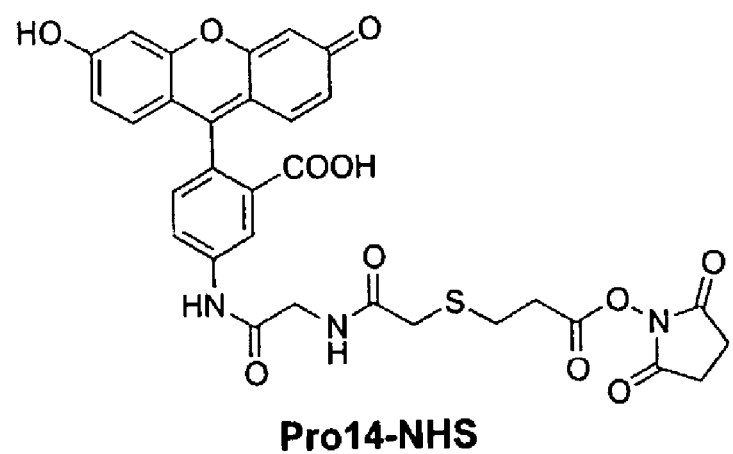
Figure 12A:
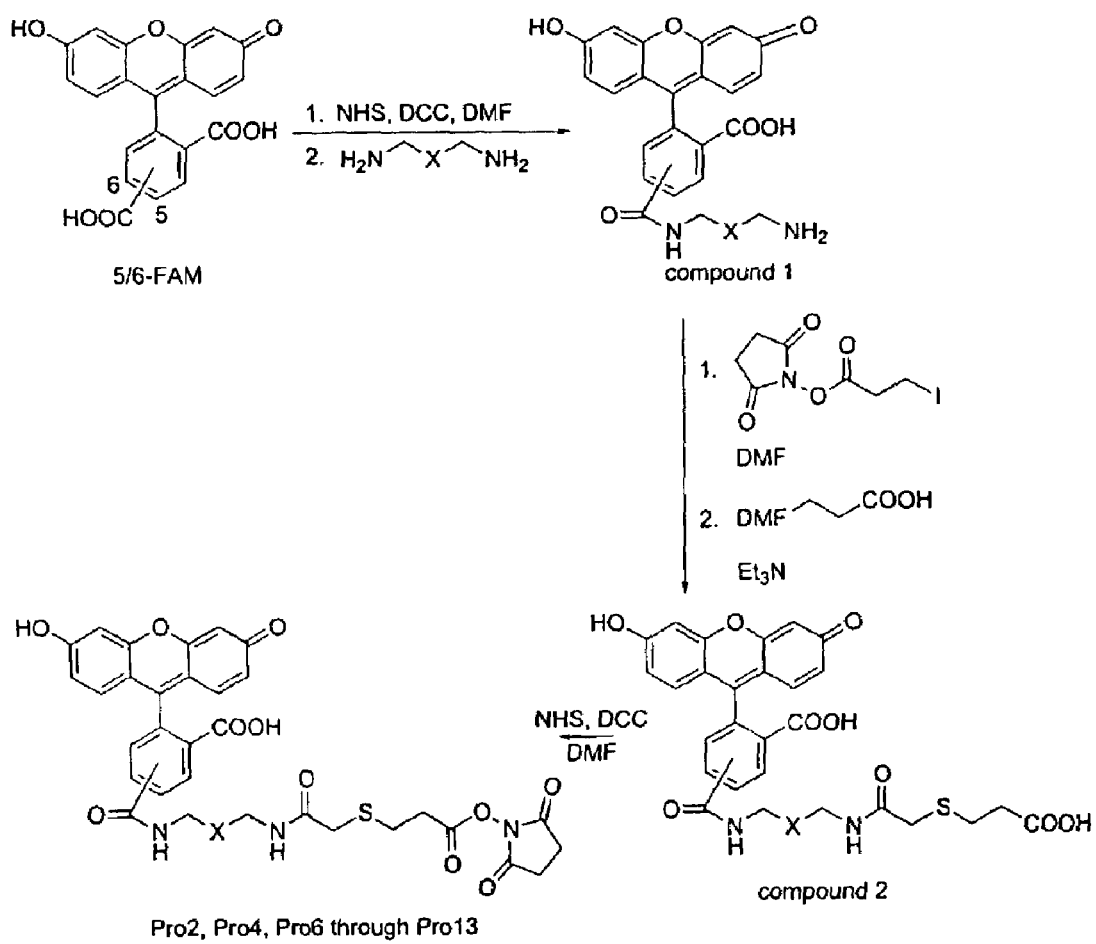
FIGS. 12A–E illustrate the chemistries of synthesis of the e-tag moieties illustrated in FIG. 11.
Figure 12B:
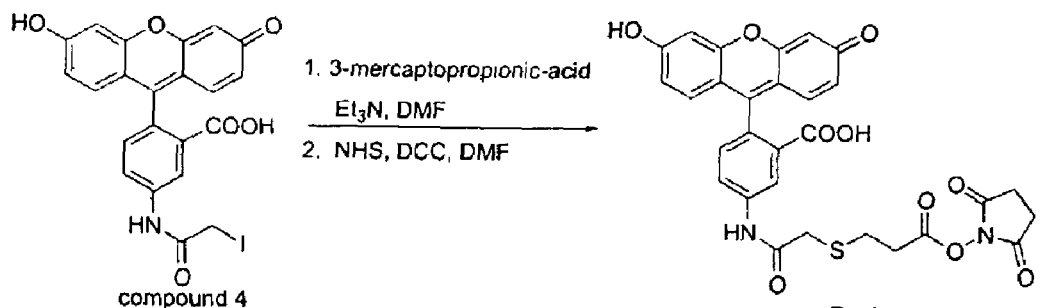
Figure 12C:
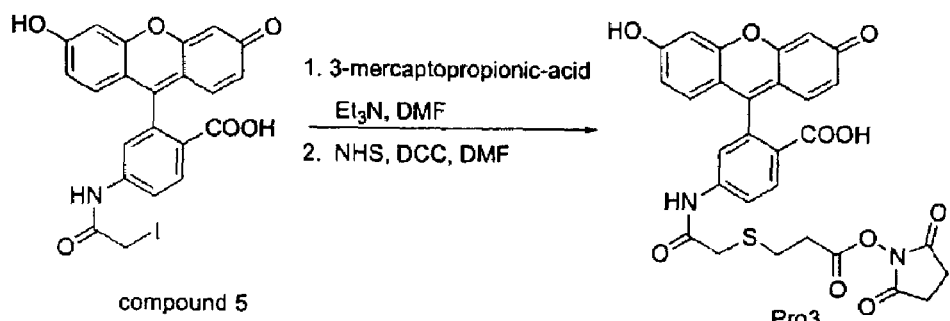
Figure 12D:
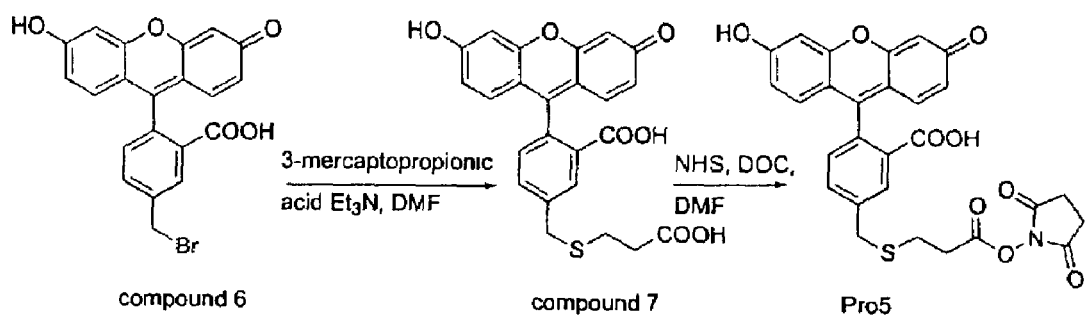
Figure 12E:
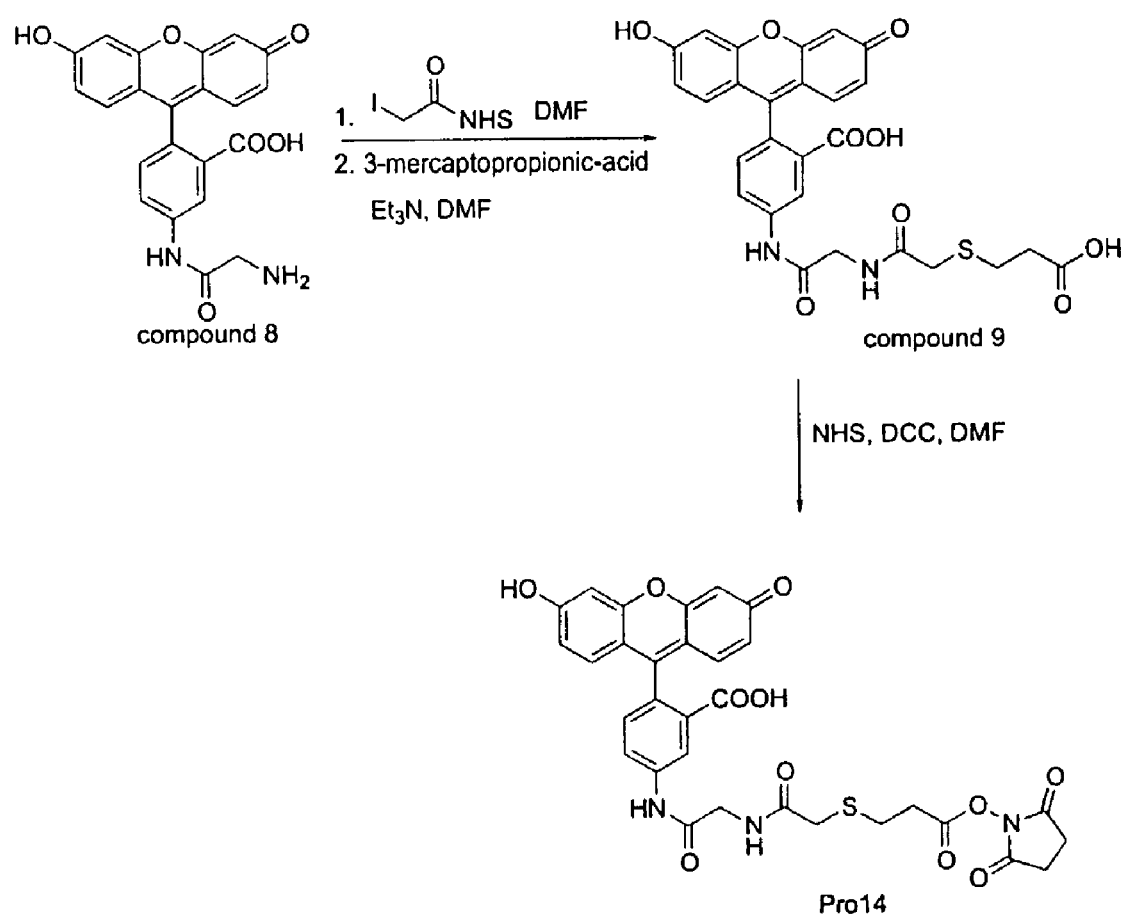

The G1 phase is a critical point at which the cell assesses whether it should enter another full round of division. Proteins in Gl progression are frequently mutated in human cancers and are attractive targets for therapeutic agents. It is desirable to look only at the early G1 phase or the late G1 phase to ascertain compounds that may be therapeutic agents. Currently, the approach is to look only at cell proliferation or cell death in assessing compounds. The various phases involved are depicted in FIG. 8.

Another assay involves the study of post-translational regulation of proteins using a library of small molecules for regulators of reversible covalent modification of proteins. A set of e-tag probes is prepared wherein each e-tag probe comprises an antibody for the protein in its modified or unmodified state, which cleavably linked to an e-tag moiety that is unique within the set of probes. A photosensitizer reagent is incorporated into the cell, either in the membrane, the cytosol, or other appropriate location. The probes are then combined with the cells in suitable reaction containers. Each of the small molecules of the library is added to a respective container. The medium is then irradiated as described above. The medium from each of the containers is treated to separate and identify the e-tag reporters. The presence of one or more of the e-tag reporters is related to ability of a respective small molecule to regulate the covalent modification of the proteins.

Another method of use of electrophoretic probes in accordance with the present invention is depicted in FIG. 11. In this embodiment a post-translational event, namely, phosphorylation of kinase is employed. A cell membrane is shown having multiple receptors including receptor R on its surface. The antigen for specifically binding to receptor R is added and, if receptor R is present, the antigen binds to it as well as cofactor Co. Enzyme Ea binds to the above complex, which then activates Ea to convert P1 to its phosphorylated counterpart P1a. Kinase P2 binds to P1a to form an active complex. This system may be used to screen for inhibitors, such as, e.g., small molecules or drugs, of the activated complex. Accordingly, the reagents for this assay include each molecule to be screened as an inhibitor where each molecule is bound to a release-inducing reagent. The second reagent is antibody (Ab2) to the complex, e.g., to the P1a of the complex, where the antibody is releasably linked to multiple electrophoretic moieties. If one of the molecules being screened binds to and inhibits the activity of the complex, the release-inducing reagent is brought into proximity of the electrophoretic probes and the e-tag moieties are released, detected and/or quantitated.

The above approach may be employed also to screen proteins for binding ability to a particular receptor. In this approach consistent with the scheme of FIG. 11, drugs that have well-defined targets may be employed. Only if one or more of such targets are present by virtue of the protein binding to receptor R, will e-tag reporters be detected. As can be seen, the methods of the invention are versatile in which entity is the known and which is the unknown.

A variation of the scheme of FIG. 11 is depicted in FIG. 12. In this embodiment the release-inducing reagent is an antibody Ab1, which specifically binds to the active complex of P2a and P1 a. The second reagent is antibody Ab2 to which multiple e-tag moieties are releasably linked. Ligands L may be studied for their ability to bind to receptor R on the surface of a cell. If L does bind to R, the active complex of P2a and P1a will form. Antibodies Ab1 and Ab2 bind to the active complex, bringing the releasable linkage into close proximity with the release-inducing reagent. The e-tag reporters are released, detected and quantitated.

Figure 13A:
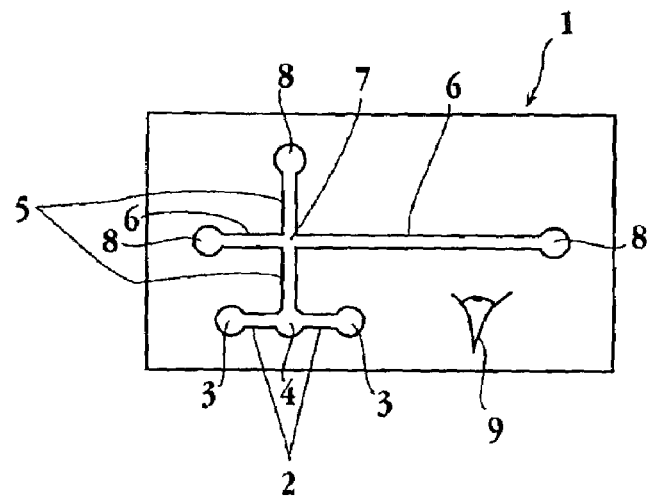
FIGS. 13A–C are schematic illustrations of a $CE^2$ Lab-Card™ device utilized in the present methods.
Figure 13B:
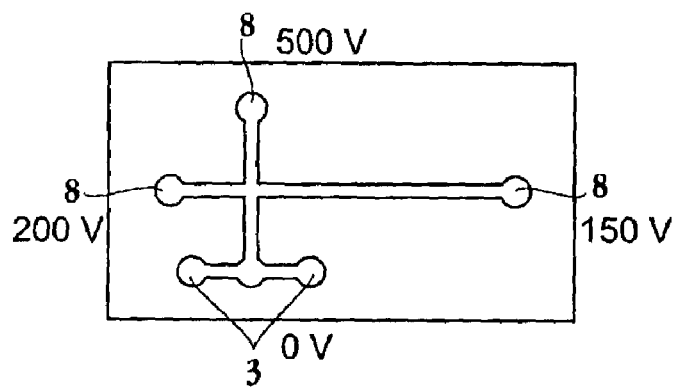
Figure 13C:
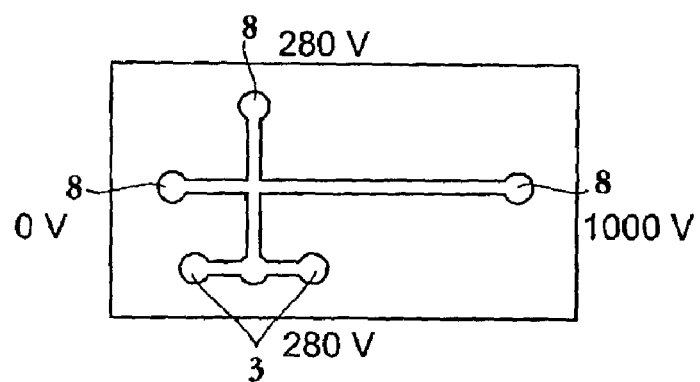

FIG. 13A depicts a hypothetical example of a protein-protein interaction pathway involving multiple phosphorylation events, to which the present methods and compositions may be applied. In this illustration, protein-protein binding is promoted by small molecules. FRAP results from the interaction of nutrients and mitogens with receptors on the surface of the cell. As can be seen in FIG. 13A, FKBP proteins bind to FRAP (binding event 1) in the presence of rapamycin resulting in 4E-BP1, which is involved in control of mRNA translation initiation. PP2A, which is a kinase activated by FRAP (binding event 2), yields p70S6K in the presence of calyculin-A, which leads to S6 protein binding (binding event 5). This latter protein is also involved in control of mRNA translation initiation. Another receptor, RTK, on the surface of a cell is acted upon by growth factor to produce kinase PI3K. In the presence of Wortmannin, PI3K is converted to PDK1 (binding event 6), which yields p70S6K leading to S6 protein. PDK1 also yields PKB (binding event 3), which in turn yields FRAP (binding event 4). The graphs in FIG. 13B show the results of assays wherein no drug is present or wherein either Wortmannin, Rapamycin or Calyculin is present, each conjugated to a release-inducing reagent and a second reagent is employed comprising an antibody for one of the proteins involved in a binding event releasably linked to an electrophoretic moiety The pathway above can assist in looking at the various binding events involved, at inhibitors of one or more of these binding events, at competitors in one or more of the binding events, at modulators of kinase activity, and so forth. With the methods and reagents of the invention one or more of the above may be monitored simultaneously in a single assay using multiple electrophoretic probes.

Analysis of Reaction Products

Methods for electrophoresis of are well known and are described, for example, in Krylov et al, Anal. Chem., 72: 111R-128R (2000); P. D. Grossman and J. C. Colburn, Capillary Electrophoresis: Theory and Practice, Academic Press, Inc., NY (1992); U.S. Pat. Nos. 5,374,527; 5,624,800; 5,552,028; ABI PRISM 377 DNA Sequencer User's Manual, Rev. A, January 1995, Chapter 2 (Applied Biosystems, Foster City, Calif.); and the like. A variety of suitable electrophoresis media are commercially available from Applied Biosystems and other vendors, including non-crosslinked media, for use with automated instruments such as the Applied Biosystems "3700" and "3100" Instruments, for example. Optimal electrophoresis conditions, e.g., polymer concentration, pH, temperature, voltage, concentration of denaturing agent, employed in a particular separation depends on many factors, including the size range of the compounds to be separated, their compositions, and the like. Accordingly application of the invention may require standard preliminary testing to optimize conditions for particular separations.

During or after electrophoretic separation, the electrophoretic tags are detected or identified by recording fluorescence signals and migration times (or migration distances) of the separated compounds, or by constructing a chart of relative fluorescent and order of migration of the electrophoretic tags (e.g., as an electropherogram). To perform such detection, the electrophoretic tags can be illuminated by standard means, e.g. a high intensity mercury vapor lamp, a laser, or the like. Typically, the electrophoretic tags are illuminated by laser light generated by a He—Ne gas laser or a solid-state diode laser. The fluorescence signals can then be detected by a light-sensitive detector, e.g., a photomultiplier tube, a charged-coupled device, or the like. Exemplary electrophoresis detection systems are described elsewhere, e.g., U.S. Pat. Nos. 5,543,026; 5,274,240; 4,879,012; 5,091,652; 6,142,162; or the like.

After completion of the reaction, which may be monitored, for example, by monitoring the change in signal such as, e.g., fluorescence as described above, or taking aliquots and assaying for total free e-tag reporters, the mixture may now be analyzed. Depending on the instrument, from one to four different fluorescers activated by the same light source and emitting at different detectable labels may be used. With improvements, five or more different fluorescers may be available, where an additional light source may be required. Electrochemical detection is described in U.S. Pat. No. 6,045,676.

In one embodiment of the presence of each of the cleaved e-tag reporters is determined by the fluorescent label contained in the e-tag moiety. The separation of the mixture of labeled e-tag reporters is typically carried out by electroseparation, which involves the separation of components in a liquid by application of an electric field, preferably, by electrokinesis (electrokinetc flow) or electrophoretic flow, or a combination of electrophoretic flow within electroosmotic flow, with the separation of the e-tag reporter mixture into individual fractions or bands. Electroseparation involves the migration and separation of molecules in an electric field based on differences in mobility. Various forms of electroseparation include, by way of example and not limitation, free zone electrophoresis, gel electrophoresis, isoelectric focusing, isotachophoresis, capillary electrochromatography, and micellar electrokinetic chromatography. Capillary electrophoresis involves electroseparation, preferably by electrokinetic flow, including electrophoretic, dielectrophoretic and/or electroosmotic flow, conducted in a tube or channel of about 1 to about 200 micrometer, usually, about 10 to about 100 micrometers cross-sectional dimensions. The capillary may be a long independent capillary tube or a channel in a wafer or film comprised of silicon, quartz, glass or plastic.

In capillary electroseparation, an aliquot of the reaction mixture containing the e-tag reporters is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

For a homogeneous assay, the sample, the first and second reagents, and ancillary reagents are combined in a reaction mixture supporting the cleavage of the linking region. The mixture may be processed to separate the e-tag reporters from the other components of the mixture. The mixture, with or without e-tag reporter enrichment, may then be transferred to an electrophoresis device, usually a microfluidic or capillary electrophoresis device and the medium modified as required for the electrophoretic separation. Where one wishes to remove from the separation channel intact e-tag reporter molecules, a ligand is bound to the e-tag reporter that is not released when the e-tag reporter is released. Alternatively, by adding a reciprocal binding member that has the opposite charge of the e-tag reporter, so that the overall charge is opposite to the charge of the e-tag reporter, these molecules will migrate toward the opposite electrode from the released e-tag reporter molecules. For example, one could use biotin and streptavidin, where streptavidin carries a positive charge. In the case of a peptide analyte, one embodiment would have cleavage at a site where the ligand remains with the peptide analyte. For example, one could have the e-tag moiety substituted for the methyl group of methionine. Using the pyrazolone of the modified methionine, one could bond to an available lysine. The amino group of the pyrazolone would be substituted with biotin. Cleavage would then be achieved with cyanogen bromide, releasing the e-tag reporter, but the biotin would remain with the peptide and any e-tag moiety that was not released from the binding member. Avidin is then used to change the polarity or sequester the e-tag moiety conjugated to the target-binding moiety for the analyte or target-binding moiety.

For capillary electrophoresis one may employ one or more detection zones to detect the separated cleaved labels. It is, of course, within the purview of the present invention to utilize several detection zones depending on the nature of the reactions, mobility-modifying moieties, and so forth.

There may be any number of detection zones associated with a single channel or with multiple channels. Suitable detectors for use in the detection zones include, by way of example, photomultiplier tubes, photodiodes, photodiode arrays, avalanche photodiodes, linear and array charge coupled device (CCD) chips, CCD camera modules, spectrofluorometers, and the like. Excitation sources include, for example, filtered lamps, LEDs, laser diodes, gas, liquid and solid-state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. No. 5,560,811 (column 11, lines 19–30), U.S. Pat. Nos. 4,675,300, 4,274,240 and 5,324,401, the relevant disclosures of which are incorporated herein by reference. Those skilled in the electrophoresis arts will recognize a wide range of electric potentials or field strengths may be used, for example, fields of 10 to 1000 V/cm are used with about 200 to about 600 V/cm being more typical. The upper voltage limit for commercial systems is about 30 kV, with a capillary length of about 40 to about 60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from about 180 to about 1500 nm, usually about 220 to about 800 nm, more usually about 450 to about 700 nm, to have low transmission losses. Suitable materials include fused silica, plastics, quartz, glass, and so forth.

Kits for Use of the e-tag Reagents

As a matter of convenience, predetermined amounts of reagents employed in the present invention can be provided in a kit in packaged combination. One exemplary kit for polypeptide analysis can comprise in packaged combination a first reagent comprising a cleavage-inducing moiety and an IMAC resin for binding to a binding site on the polypeptide that has undergone phosphorylation. The kit can further comprise one or more electrophoretic probes comprising a specific binding agent for a particular polypeptide cleavably linked to an e-tag reporter. For example, each of the e-tag probes may comprise a polypeptide-binding moiety such as an antibody cleavably linked to an e-tag moiety. The mobility-modifying moiety of each of the e-tag probes has a mobility that allows differentiation of one e-tag reporter from another and is unique to a particular protein of interest. The kits will include at least about 1, usually at least about 10, more usually at least about 20 and frequently at least about 50 or more different probes that can generate e-tag reporters that can be separated by their mobility. On the other hand, where the polypeptide itself is specifically cleaved to provide an e-tag moiety, the kit may include reagents wherein each reagent comprises a detection moiety linked to a moiety for binding to a specific cleaved e-tag moiety The kit may further comprise a device for conducting capillary electrophoresis as well as reagents that may be necessary to activate the cleavage-inducing moiety of the cleavage-inducing reagent. The kit can further include various buffered media, some of which may contain one or more of the above reagents.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

EXAMPLES

The invention is demonstrated further by the following syntheses and illustrative examples. Parts and percentages are by weight unless otherwise indicated. Temperatures are in degrees Centigrade (° C.) unless otherwise specified. The following preparations and examples illustrate the invention but are not intended to limit its scope. Unless otherwise indicated, peptides used in the following examples were prepared by synthesis using an automated synthesizer and were purified by gel electrophoresis or HPLC.

The following abbreviations have the meanings set forth below:
Tris HCl—Tris(hydroxymethyl)aminomethane-HCl (a 10×solution) from BioWhittaker, Walkersville, Md.
HPLC—high performance liquid chromatography
TLC—thin layer chromatography
BSA—bovine serum albumin from Sigma Chemical Company, St. Louis Mo.
EDTA—ethylene diamine tetra-acetate from Sigma Chemical Company
g—grams
mM—millimolar
FAM—carboxyfluorescein
EMCS—N-ε-maleimidocaproyloxy-succinimide ester
EDC—1-Ethyl-3-(3-dimethylaminopropyl)carbodiimide
NHS—N-hydroxysuccinimide
DCC—1,3-dicylcohexylcarbodiimide
DMF—dimethylformamide
Fmoc—N-(9-fluorenylmethoxycarbonyl)-

Conjugation of Photosensitizer Molecules to Assay Reagents

Photosensitizer molecules are conjugated to a metal affinity agent, a boronic acid containing agent, a hub molecule, and the like by various conventional methods and configurations. For example, an activated (NHS ester, aldehyde, sulfonyl chloride, etc) photosensitizer (Rose Bengal, phthalocyanine, etc.) can be reacted with reactive amino-group containing moieties (aminodextran, amino-group containing agents (with appropriate protection of metal binding sites), other small and large molecules). The formed conjugates can be used directly (for example the antibody-photosensitizer conjugate, Biotin-LC-photosensitizer, etc.) in various assays. Also, the formed conjugates can be further coupled with antibody (for example, aminodextran-photosensitizer conjugate containing 20–200 photosensitizers and 200–500 amino-groups can be coupled to periodate oxidized antibody molecules to generate the antibody-dextran-sensitizer conjugate) or with the antibody and a particle. For example, aminodextran-sensitizer conjugate containing 20–200 photosensitizers and 200–500 amino-groups can be coupled to carboxylated polystyrene beads by EDC coupling chemistry to form the photosensitizer-aminodextran-particle conjugate. Methods for incorporation of a photosensitizer into a particle are given in, e.g., U.S. Pat. No. 5,340,716. Then the Na-periodate oxidized antibody molecules can be reacted with the amino-groups of the aminodextran molecule, in presence of sodium cyanoborohydride, to generate the antibody-dextran-photosensitizer-particle conjugate, referred to herein as a "photosensitizer bead." It should be noted that instead of an antibody molecule, avidin or other molecules can be used also.

Conjugation of an e-tag Moiety and Release of an e-tag Reporter

Figure 14:
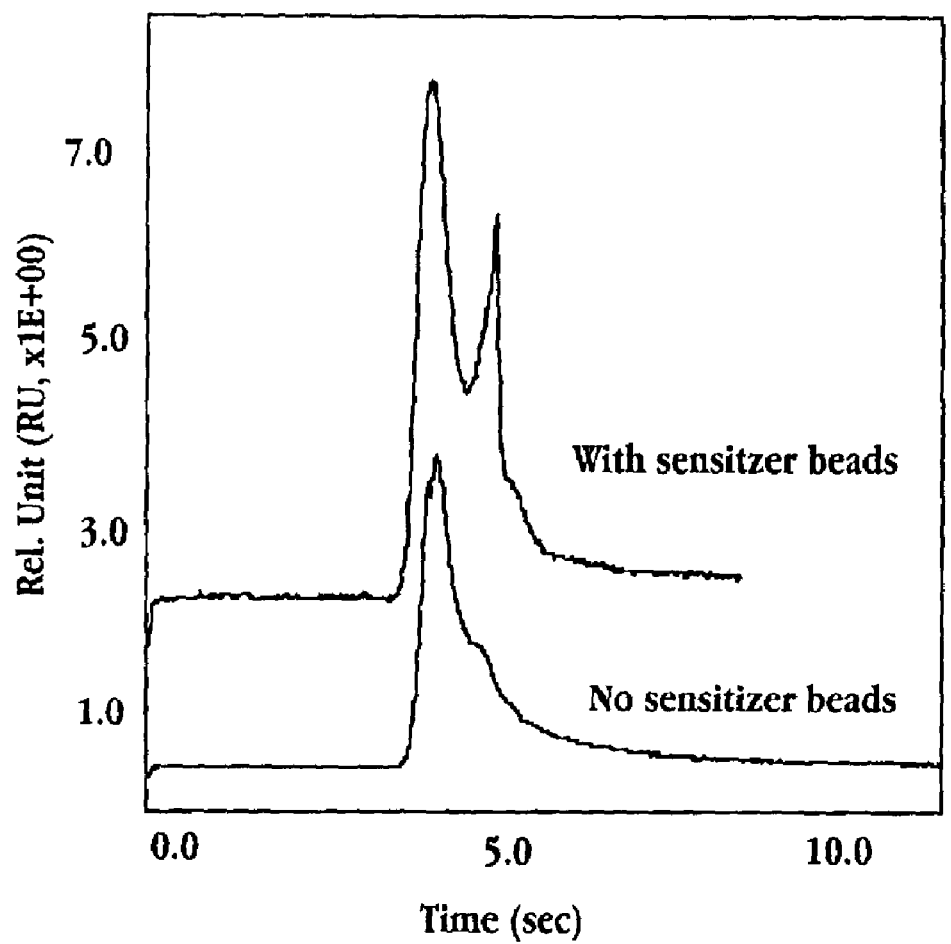
FIG. 14 shows two electropherograms demonstrating e-tag reporter analysis using a $CE^2$ LabCard.
Figure 15:
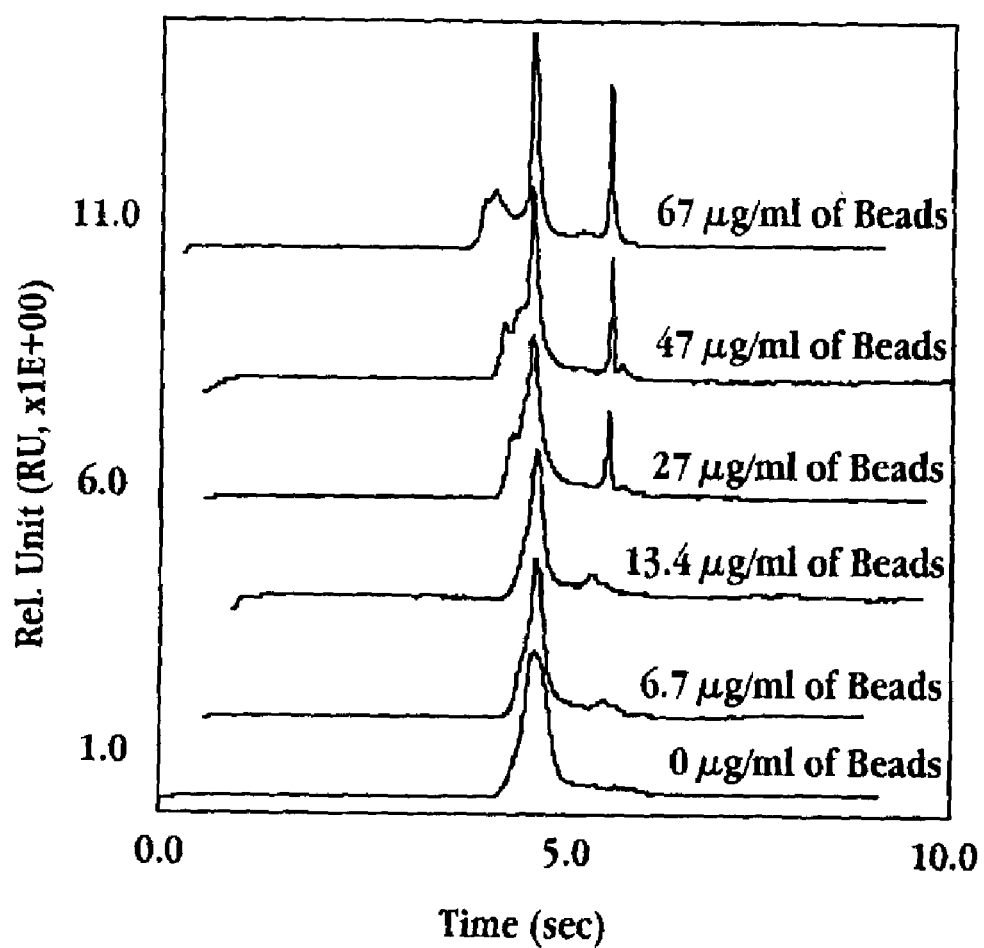
FIG. 15 shows multiple electropherograms demonstrating e-tag reporter analysis using a $CE^2$ LabCard.

FIG. 14 summarizes the methodology for conjugation of an e-tag moiety to an antibody, and the reaction of the resulting conjugate with singlet oxygen to produce a sulfinic acid moiety as the released e-tag reporter. FIG. 15 shows 14 e-tag reagents. Most of these target structures utilized 5- or 6-carboxyfluorescein (FAM) as starting material.

Preparation of Pro2, Pro4, and Pro6 through Pro13

Figure 16:
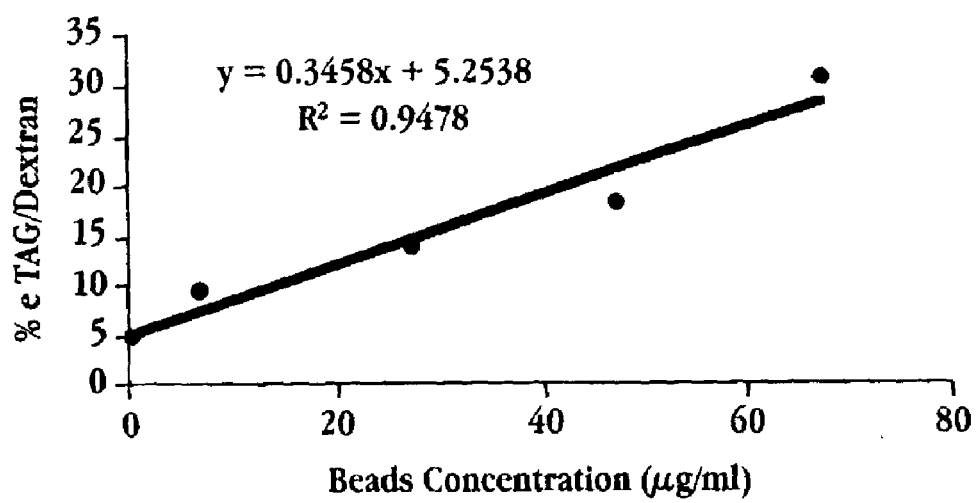
FIG. 16 depicts the linear calibration curve for the release of e-tag reporters as a function of the photosensitizer bead concentration.

The scheme outlined in FIG. 16A shows a five-step procedure for the preparation of the carboxyfluorescein-derived e-tag moieties, namely, Pro2, Pro4, Pro6, Pro7, Pro8, Pro9, Pro10, Pro11, Pro12, and Pro13. The first step involves the reaction of a 5- or 6-FAM with N-hydroxysuccinimide (NHS) and 1,3-dicylcohexylcarbodiimide (DCC) in DMF to give the corresponding ester, which was then treated with a variety of diamines to yield the desired amide, compound 1. Treatment of compound 1 with N-succinimidyl iodoacetate provided the expected iodoacetamide derivative, which was not isolated but was further reacted with 3-mercaptopropionic acid in the presence of triethylamine. Finally, the resulting β-thioacid (compound 2) was converted, as described above, to its NHS ester. The various e-tag moieties were synthesized starting with 5- or 6-FAM, and one of various diamines. The diamine is given $H_2N \wedge X \wedge NH_2$ in the first reaction of FIG. 16A. The regloisomer of FAM and the chemical entity of "X" within the diamine are indicated in the table below for each of the e-tag moieties synthesized.

| e-tag moiety | FAM | X |
| --- | --- | --- |
| Pro2 | 5-FAM | $C(CH_3)_2$ |
| Pro4 | 5-FAM | no carbon |
| Pro6 | 5-FAM | $(CH_2)_8$ |
| Pro7 | 5-FAM | $CH_2OCH_2CH_2OCH_2$ |
| Pro8 | 5-FAM | $CH_2CH_2OCH_2CH_2OCH_2CH_2OCH_2CH_2$ |
| Pro9 | 5-FAM | 1,4-phenyl |
| Pro10 | 6-FAM | $C(CH_3)_2$ |
| Pro11 | 6-FAM | no carbon |
| Pro12 | 6-FAM | $CH_2OCH_2CH_2OCH_2$ |
| Pro13 | 6-FAM | $CH_2CH_2OCH_2CH_2OCH_2CH_2OCH_2CH_2$ |

Synthesis of Compound 1

To a stirred solution of 5- or 6-carboxyfluorescein (0.5 mmol) in dry DMF (5 mL) were added N-hydroxysuccinimide (1.1 equiv.) and 1,3-dicylcohexylcarbodiimide (1.1 equiv.). After about 1 0 minutes, a white solid (dicyclohexylurea) started forming. The reaction mixture was stirred under nitrogen at room temperature overnight. TLC (9:1 $CH_2Cl_2$—MeOH) indicated complete disappearance of the starting material.

The supernatant from the above mixture was added dropwise to a stirred solution of diamine (2–5 equiv.) in DMF (10 mL). As evident from TLC (40:9:1 $CH_2Cl_2$—MeOH—$H_2O$), the reaction was complete instantaneously. The solvent was removed under reduced pressure. Flash chromatography of the resulting residue on Iatrobeads silica provided the desired amine (compound 1) in 58–89% yield. The $^1$H NMR (300 MHz, DMSO-$d_6$) of compound 1 was in agreement with the assigned structure.

Synthesis of Compound 2

To the amine (compound 1) (0.3 mmol) were sequentially added dry DMF (10 mL) and N-succinimidyl iodoacetate (1.1 equiv.). The resulting mixture was stirred at room temperature until a clear solution was obtained. TLC (40:9:1 $CH_2Cl_2$—MeOH—$H_2O$) revealed completion of the reaction.

The above reaction solution was then treated with triethylamine (1.2 equiv.) and 3-mercaptopropionic acid (3.2 equiv.). The mixture was stirred at room temperature overnight. Removal of the solvent under reduced pressure followed by flash chromatography afforded the β-thioacid (compound 2) in 62–91% yield. The structure of compound 2 was assigned on the basis of its $^1$NMR (300 MHz, DMSO-$d_6$).

Synthesis of Pro2, Pro4, and Pro6 through Pro13

To a stirred solution of the β-thioacid (compound 2) (0.05 mmol) in dry DMF (2 mL) were added N-hydroxysuccinimide (1.5 equiv.) and 1,3-dicylcohexylcarbodiimide (1.5 equiv.). The mixture was stirred at room temperature under nitrogen for 24–48 h (until all of the starting material had reacted). The reaction mixture was concentrated under reduced pressure and then purified by flash chromatography to give the target molecule in 41–92% yield.

Preparation of Pro1

The compounds of this reaction are shown in FIG. 16B. To a stirred solution of 5-iodoacetamidofluorescein (compound 4) (24 mg, 0.047 mmol) in dry DMF (2 mL) were added triethylamine (8 μL, 0.057 mmol) and 3-mercaptopropionic acid (5 μL, 0.057 mmol). The resulting solution was stirred at room temperature for 1.5 h. TLC (40:9:1 $CH_2Cl_2$—MeOH—$H_2O$) indicated completion of the reaction. Subsequently, N-hydroxysuccinimide (9 mg, 0.078 mmol) and 1,3-dicylcohexylcarbodiimide (18 mg, 0.087 mmol) were added. The reaction mixture was stirred at room temperature under nitrogen for 19 h at which time TLC showed complete disappearance of the starting material. Removal of the solvent under reduced pressure and subsequent flash chromatography using 25:1 and 15:1 $CH_2Cl_2$—MeOH as eluant afforded Pro1 (23 mg, 83%).

Preparation of Pro3

The compounds of this reaction are shown in FIG. 16C. To a stirred solution of 6-iodoacetamidofluorescein (compound 5) (26 mg, 0.050 mmol) in dry DMF (2 mL) were added triethylamine (8 μL, 0.057 mmol) and 3-mercaptopropionic acid (5 μL, 0.057 mmol). The resulting solution was stirred at room temperature for 1.5 h. TLC (40:9:1 $CH_2Cl_2$—MeOH—$H_2O$) indicated completion of the reaction. Subsequently, N-hydroxysuccinimide (11 mg, 0.096 mmol) and 1,3-dicylcohexylcarbodiimide (18 mg, 0.087 mmol) were added. The reaction mixture was stirred at room temperature under nitrogen for 19 h at which time TLC showed complete disappearance of the starting material. Removal of the solvent under reduced pressure and subsequent flash chromatography using 30:1 and 20:1 $CH_2Cl_2$—MeOH as eluant provided Pro3 (18 mg, 61%).

Preparation of Pro5

The compounds of this reaction are shown in FIG. 16D.

Synthesis of Compound 7

To a stirred solution of 5-(bromomethyl)fluorescein (compound 6) (40 mg, 0.095 mmol) in dry DMF (5 mL) were added triethylamine (15 µL, 0.108 mmol) and 3-mercaptopropionic acid (10 µL, 0.115 mmol). The resulting solution was stirred at room temperature for 2 days. TLC (40:9:1 $CH_2Cl_2$—MeOH—$H_2O$) indicated completion of the reaction. The reaction solution was evaporated under reduced pressure. Finally, flash chromatography employing 30:1 and 25:1 $CH_2Cl_2$—MeOH as eluant provided the β-thioacid (compound 7) (28 mg, 66%).

Synthesis of Pro5

To a solution of the acid (compound 7) (27 mg, 0.060 mmol) in dry DMF (2 mL) were added N-hydroxysuccinimide (11 mg, 0.096 mmol) and 1,3-dicylcohexylcarbodiimide (20 mg, 0.097 mmol). The reaction mixture was stirred at room temperature under nitrogen for 2 days at which time TLC (9:1 $CH_2Cl_2$—MeOH) showed complete disappearance of the starting material. Removal of the solvent under reduced pressure and subsequent flash chromatography with 30:1 $CH_2Cl_2$—MeOH afforded Pro5 (24 mg, 73%).

Preparation of Pro14

The compounds of this reaction are shown in FIG. 16E.

Synthesis of Compound 9

To 5-aminoacetamidofluorescein (compound 8) (49 mg, 0.121 mmol) were sequentially added dry DMF (4 mL) and N-succinimidyl iodoacetate (52 mg, 0.184). A clear solution resulted and TLC (40:9:1 $CH_2Cl_2$—MeOH—$H_2O$) indicated complete disappearance of the starting material.

The above reaction solution was then treated with triethylamine (30 µL, 0.215 mmol) and 3-mercaptopropionic acid (30 µL, 0.344 mmol). The resulting mixture was stirred for 2 h. Removal of the solvent under reduced pressure followed by flash chromatography using 20:1 and 15:1 $CH_2Cl_2$—MeOH as eluant gave the β-thioacid (compound 9) (41 mg, 62%). The structural assignment was made on the basis of $^1$NMR (300 MHz, DMSO-$d_6$).

Synthesis of Pro14

To a stirred solution of compound 9 (22 mg, 0.04 mmol) in dry DMF (2 mL) were added N-hydroxysuccinimide (9 mg, 0.078 mmol) and 1,3-dicylcohexylcarbodiimide (16 mg, 0.078 mmol). The resulting solution was stirred at room temperature under nitrogen for about 24 h. The reaction mixture was concentrated under reduced pressure and the residue purified by flash chromatography using 30:1 and 20:1 $CH_2Cl_2$—MeOH as eluant to give Pro14 (18 mg, 70%).

Example 1 e-Tag Reporter Assay for Protein Analysis

A. Labeling of Aminodextran (MW ~500,000) with an e-tag Moiety and Biotin

Aminodextran was used as a model for demonstrating e-tag reporter release in relation to a high molecular weight molecule, which also serves as a model for proteins. The number of amino groups for 10 mg aminodextran was calculated as $2\times10^{-8}$ moles. For a ratio of 1:4 biotin to e-tag moiety, the number of moles of biotin NHS ester employed was $1.85\times10^6$, and the number of moles of maleimide NHS ester was $7.4\times10^{-6}$. 10.9 mg of aminodextran was dissolved in 6 mL of 0.1% PBS buffer. 10 mg of Biotin-x-x NHS ester and 23.7 mg of EMCS were dissolved together in 1 mL of DMF and added in 50 µL portions at 30 min intervals to the aminodextran solution while it was stirring and keeping away from the light. After the final addition of the DMF solution, the mixture was kept overnight (while stirring and away from the light). Then, the mixture was dialyzed using a membrane with a molecular weight cut-off of 10,000 Daltons. The membrane was immersed in a beaker containing 2 L of water while stirring. The water was changed four times in a 2 h interval. The membrane was kept in the water overnight (while stirring and keeping away from the light). Then the solution was lyophilized and the lyophilized powder was used for e-tag moiety labeling.

B. Reaction of Biotin and Maleimide Labeled Aminodextran with the Moiety, SAMSA.

SAMSA [5-(((2-(and-3)-S-acetylmercapto)succinoyl)amino)fluorescein]was employed as an e-tag moiety to react with maleimide in the aminodextran molecule. For this purpose 0.3 mg (~$5.3\times10^{-9}$ moles) of biotin and EMCS labeled with aminodextran were dissolved in 10 µl of water. 1.1 mg of SAMSA (~$1.2\times10^{-6}$ moles) was dissolved in 120 µL of 0.1 M NaOH and incubated at room temperature for 15 min (for the activation of the thiol group). Then, the excess of NaOH was neutralized by the addition of 2 µL of 6M HCl, and the pH of the solution was adjusted to 7.0 by the addition of 30 µL of phosphate buffer (200 mM, pH 7.0). The activated SAMSA solution was added to the 10 µL solution of the labeled aminodextran and incubated for 1 h. The e-tag moiety-labeled aminodextran was purified with gel filtration using Sephadex G-25 (Amersham), and purified samples were collected.

C. The Release of e-tag Reporter from Labeled Aminodextran

Figure 17:
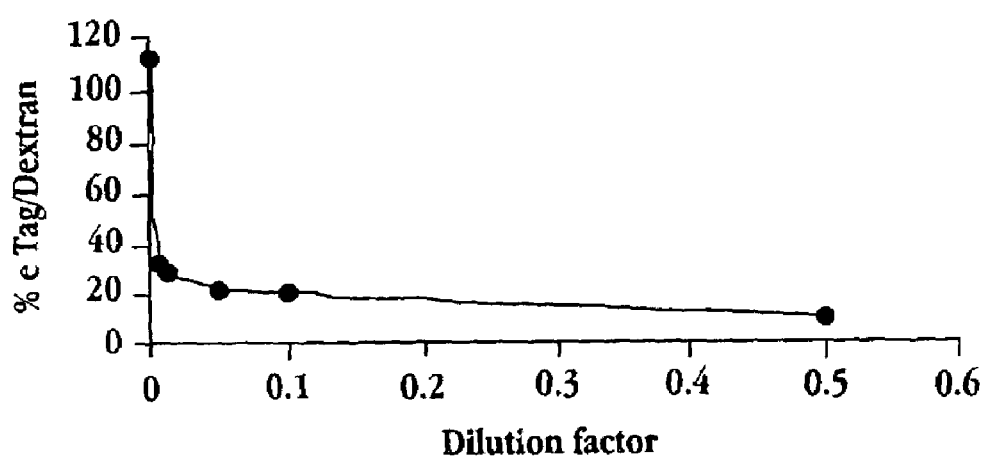
FIG. 17 shows a data curve of the effect of the concentration of labeled aminodextran on e-tag reporter release.

2 µL of streptavidin-labeled photosensitizer beads (100 µg/mL) were added carefully in the dark to 5 µL of purified labeled aminodextran and incubated in the dark for 15 min. Then the solution was irradiated for 1 min at 680 nm. The release of the e-tag reporter was examined be CE using $CE^2$ LabCard™ device (ACLARA BioSciences, Mountain View, Calif.). As shown in FIG. 17A, the $CE^2$ LabCard 1 consists of two parts: evaporation control and injection/separation. The evaporation control incorporates an evaporation control channel 2 (450 µm wide and 50 µm deep) with two replenishment buffer reservoirs 3 (2 mm in diameter) and the evaporation-controlled sample well 4 (1 mm diameter) in the middle of the evaporation control channel. The volume of the replenishment buffer reservoirs are 4.7 µL while the volume of the sample well is only 1.2 µL, and the volume of the channel 2 beneath the middle sample well is about 40 nL. The second part of the $CE^2$ device, which is used for injection and separation, consists of an injection microchannel 5 and a separation microchannel 6, intersecting at a junction 7, and having dimensions of 120 µm wide and 50 µm deep. Both ends of the separation channel and one end or the injection channel connect with buffer reservoirs 8, while the second end of the injection channel connects directly to the evaporation-controlled sample well 4. The channels are enclosed by laminating a film (MT40) to the LabCard™. A detector 9 is positioned 10 mm from the junction. After filling the $CE^2$ LabCard device with separation buffer (20 mM HEPES, pH 7.4 and 0.5% PEO), 300 nL of the assay mixture was added to the sample well 4. The sample was injected into the microchannel junction 7 by applying voltages to the buffer reservoirs as indicated in FIG. 17B. The sample was then separated as is shown in FIG. 17C.

Figure 18:
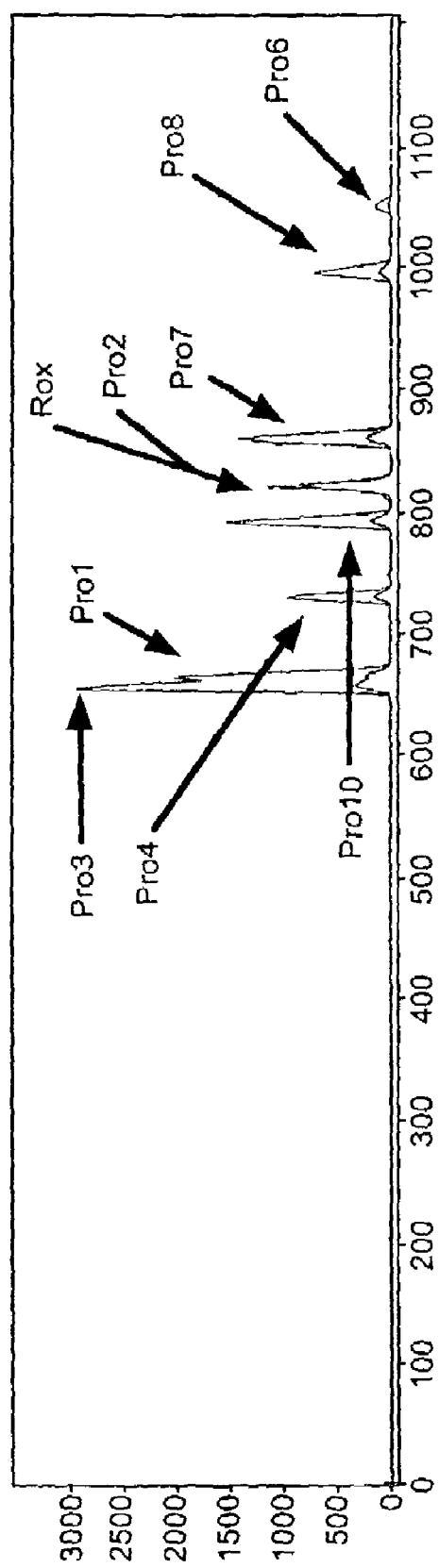
FIG. 18 shows the electrophoretic separation of 8 e-tag reporters on an ABI310.

FIG. 18 shows the electropherograms of purified labeled aminodextran with and without photosensitizer beads. The addition of the photosensitizer beads lead to the release of the e-tag reporter from the aminodextran using singlet oxygen produced by photosensitizer upon the irradiation at 680 nm. Experimental conditions: separation buffer 20 mM HEPES pH 7.4, and 0.5% PEO; voltage configurations as described in FIG. 17; assay mixture had 29 µg/ml streptavidin-labeled photosensitizer beads and irradiated for 1 min at 680 nm using 680±10 nm filter and a 150 W lamp. As shown, the addition of the photosensitizer beads leads to the release of the e-tag reporter from the aminodextran using singlet oxygen produced by the photosensitizer upon irradiation at 680 nm. In order to optimize the irradiation time, reaction mixtures containing photosensitizer beads were irradiated for different lengths of time ranging from 1 to 10 min. There is no significant increase in the e-tag reporter release for irradiation times longer than 1 min.

Figure 19:
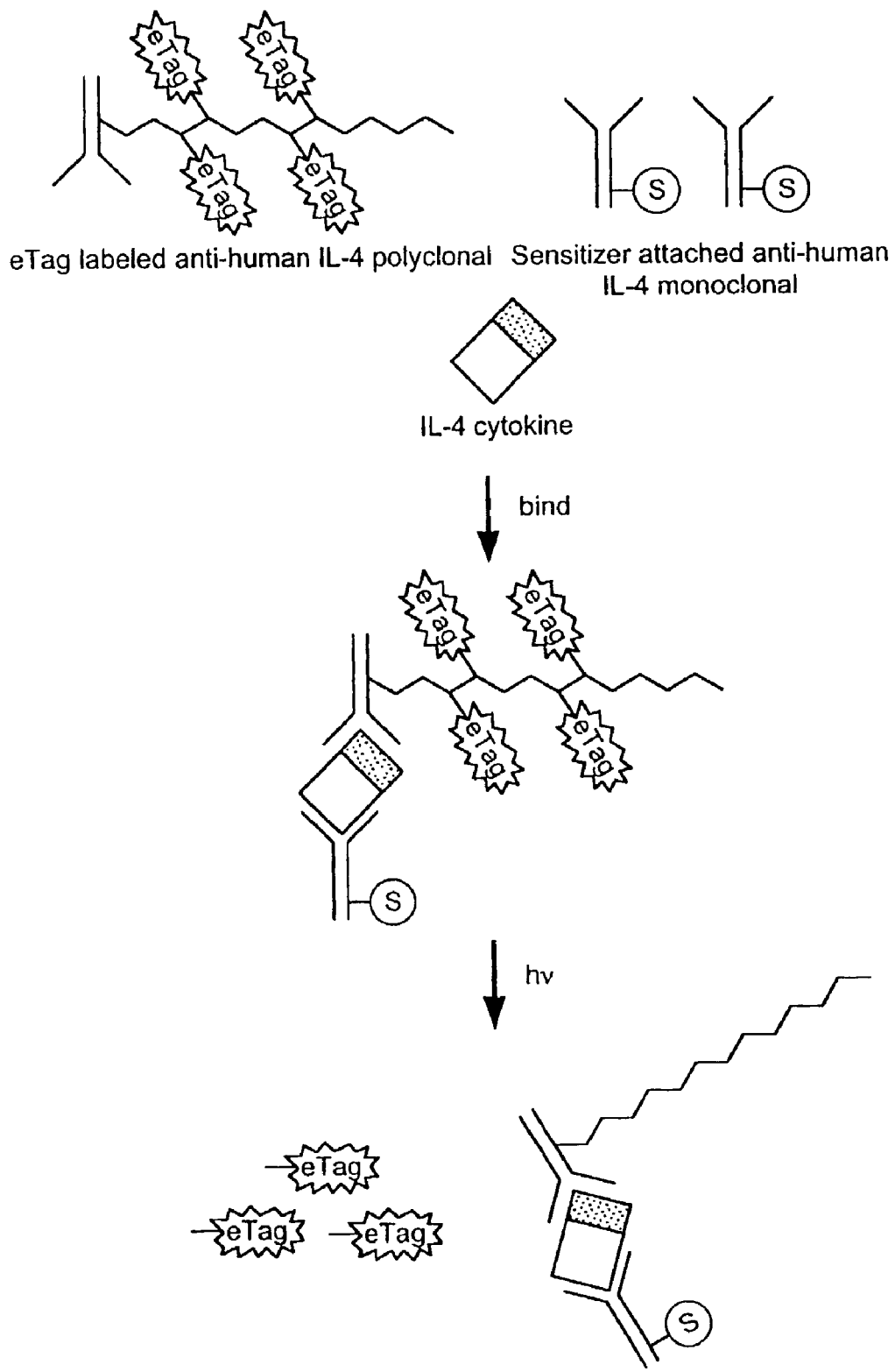
FIG. 19 is a cartoon depicting a sandwich assay for the quantification of cytokines IL-4 and IL-5.

FIG. 19 shows the effect of photosensitizer bead concentration on e-tag reporter release. The figure shows the separation of purified labeled aminodextran using different concentrations of photosensitizer beads. The higher concentration of photosensitizer beads leads to the higher release of e-tag reporters from the labeled aminodextran. Experimental conditions: separation buffer 20.0 mM HEPES pH 7.4, and 0.5% PEO; voltage configurations as described for FIG. 17; assay mixture was irradiated for 1 min at 680 nm using 680±10 nm filter and a 150W lamp.

Figure 20:
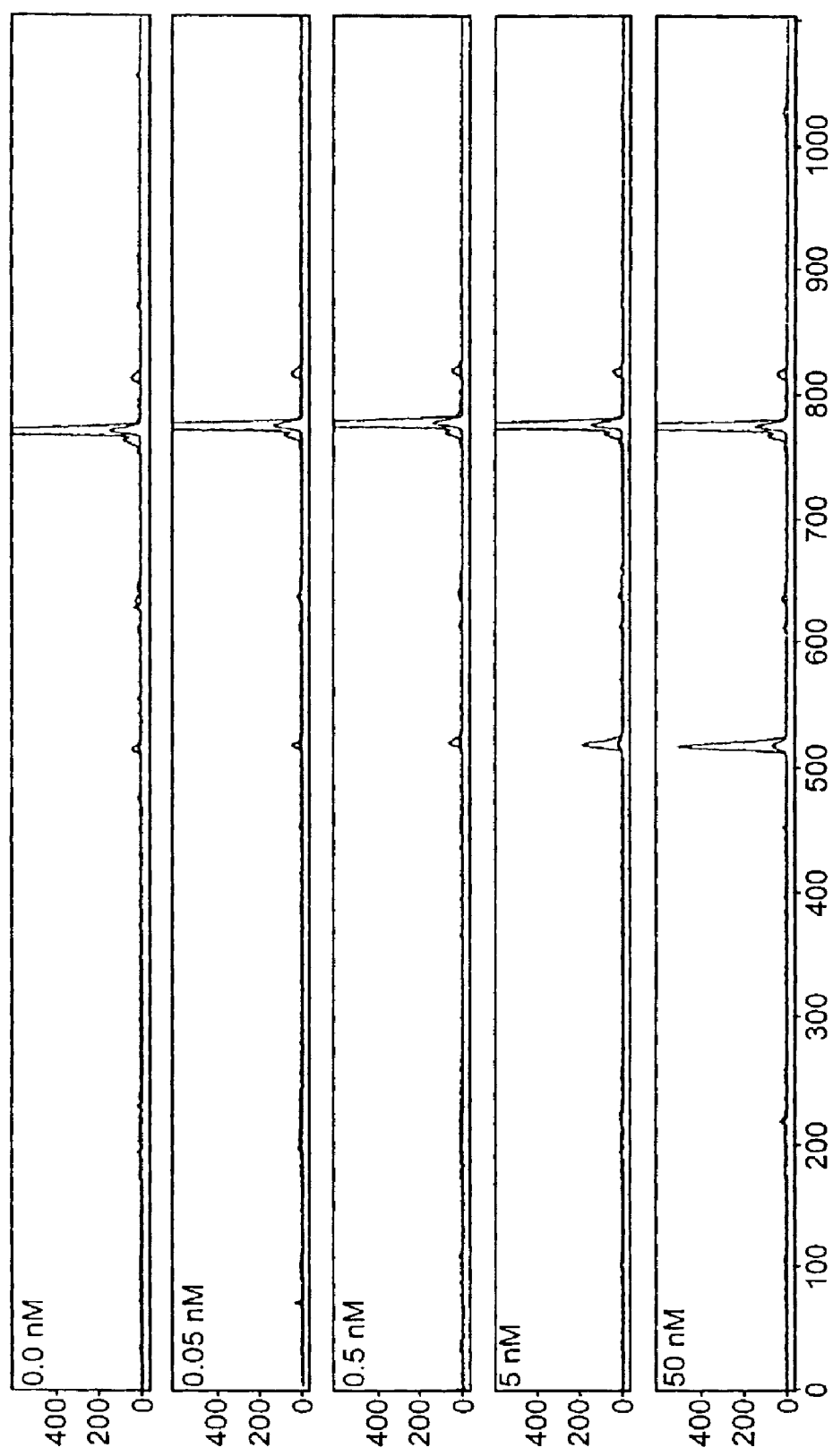
FIG. 20 shows a series of electropherograms demonstrating e-tag reporter (Pro1) analysis in an IL-4 titration study.

FIG. 20 depicts a linear calibration curve for the release of e-tag reporters as a function of photosensitizer bead concentration. Results were obtained using a $CE^2$ LabCard. Experimental conditions: separation buffer 20.0 mM HEPES pH 7.4, and 0.5% PEO; voltage configurations as described for FIG. 17; assay mixture was irradiated for 1 min at 680 nm using 680±10 nm filter and a 150 W lamp.

Figure 21:
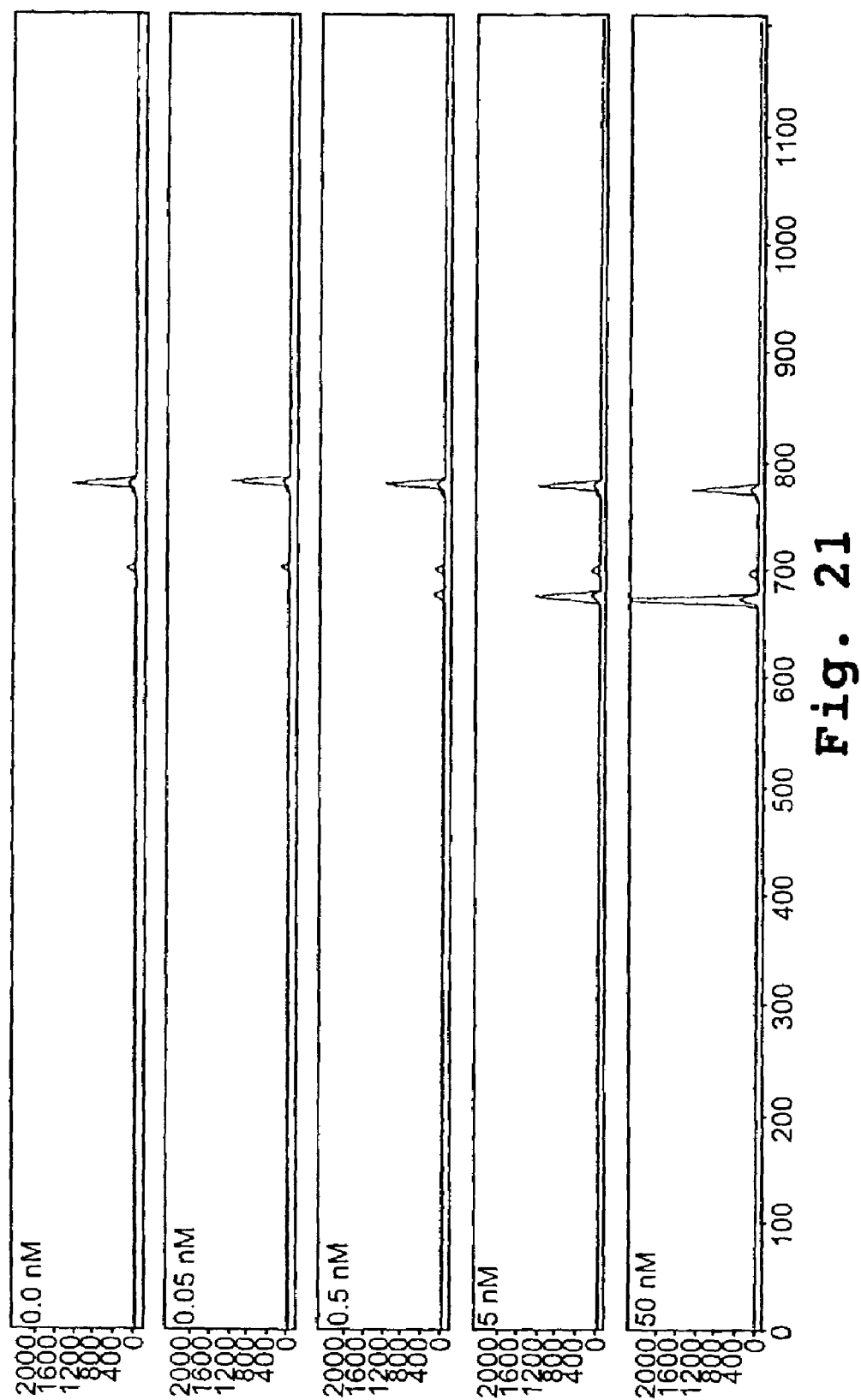
FIG. 21 shows a series of electropherograms demonstrating e-tag reporter (Pro10) analysis in an IL-6 titration study.

In addition, the effect of the concentration of labeled aminodextran on e-tag reporter release was also examined, with the results shown in FIG. 21. As demonstrated in this figure, a lower concentration of labeled aminodextran for a given concentration of photosensitizer beads leads to more efficient e-tag reporter release (or higher ratio of e-tag reporter released to the amount of labeled aminodextran). Results were obtained using a $CE^2$ LabCard. Experimental conditions: separation buffer 20.0 mM HEPES pH 7.4, and 0.5% PEO; voltage configurations as described for FIG. 17; assay mixture had 29 µg/ml of photosensitizer beads and was irradiated for 1 min at 680 nm using 680±10 nm filter and a 150 W lamp.

Example 2 e-tag Reporter Assay for Protein Analysis

A. Conjugation of e-tag Moieties to Antibodies.

Two different approaches for conjugation were employed. The first approach involved the direct attachment of e-tag moieties to the antibody, and the second approach involved attachment of e-tag moieties to dextran that was then attached to the antibody.

(A1) Direct Conjugation of e-tag Moieties to Antibodies.

E-tag moieties were synthesized with an NHS ester end that reacted with primary amines of the antibody to form a stable amide linkage. This resulted in a random attachment of e-tag moieties over the surface of the antibody. Modification with up to 6 to 12 NHS ester containing molecules per antibody molecule typically results in no decrease in antigen binding activity. Even higher ratios of NHS ester to antibody are possible with only slight loss of activity.

Protocol

1. Purified human IgG (purchased from Sigma-Aldrich) was diluted to 2 mg/ml in 1×PBS (0.1 M sodium phosphate, 0.15 M NaCl, pH 7.2).
2. NHS ester containing e-tag moieties was dissolved in DMF (dimethylformamide) to a final concentration between 10 to 20 nmols/µl DMF.
3. 500 µL of diluted human IgG (6.5 nmol) was mixed with either 1, 5, 25, or 50 µl of e-tag moiety (14, 68, 340, and 680 nmols respectively).
4. The solution was allowed to react for 2 hours on ice in the dark.
5. The e-tag moiety-conjugated antibody was purified by dialysis against 0.1×PBS (10 mM sodium phosphate, 15 mM NaCl, pH 7.2) for 20 hours at 4° C.

(A2) Conjugation of e-tag Moiety-Dextran to Antibodies.

In this second example, e-tag moieties were first attached to amine-containing dextran via an amide linkage essentially as described above. Polyclonal and some monoclonal antibodies contain carbohydrates in the Fc portion of the antibody. These polysaccharides can be periodate-oxidized to form reactive aldehyde residues. The amino-dextran containing e-tag moiety is then conjugated to the aldehyde residues of the oxidized antibodies through the formation of a Schiff base. This linkage is further stabilized by reduction to a secondary amine linkage with sodium cyanoborohydride.

The extremely large size of the amino-dextran (molecular weight of 500,000) containing 50 to 500 available aminogroups for conjugation to e-tag moieties allows for a significant increase in the number of e-tag moieties per antibody, resulting in signal amplification. Since the dextran is coupled through the carbohydrate on the Fc portion of the antibody, it is sufficiently removed from the antigen-binding site without comprising activity.

Protocol for Conjugation of e-tag Moieties to Amino-Dextran

1. Amino-dextran (500,000 mw with 500 amines/mole dextran) was dissolved in 90% DMF to a final concentration of 2 mg/ml (2 nmol amine/µl).
2. NHS ester containing e-tag moieties were dissolved in DMF (dimethylformamide) to a final concentration between 10 to 20 nmols/µl DMF.
3. 500 µl of amino-dextran (1000 nmol of amine) was mixed with either 500, 1000, or 2000 nmol e-tag moiety.
4. The solution was allowed to react for 2 hours on ice in the dark.
5. The e-tag moiety-conjugated amino-dextran was purified by dialysis against 0.1×PBS (10 mM sodium phosphate, 15 mM NaCl, pH 7.2) for 20 hours at 4° C.
6. Precipitate was removed by centrifugation at 14,000×g for 5 minutes.

Protocol for Oxidation of Antibodies with Sodium Periodate 1. 500 µl (2.8 nmol) of purified anti-human IL-4 polyclonal antibody (purchased from Pierce) was oxidized in the presence of 10 mM sodium periodate (Aldrich).
2. The solution was allowed to react for 30 minutes at room temperature in the dark.

3. Ethylene glycol is added to a final concentration of 100 mM and allowed to incubate for 10 minutes at room temperature.
4. The oxidized antibody was purified by dialysis against 0.1×PBS (10 mM sodium phosphate, 15 mM NaCl, pH 7.2) for 2 hours at 4° C.

Protocol for Conjugation of Periodate-Oxidized Antibody to e-tag Moieties Containing Amino-Dextran 1. 54 µl (300 pmol) of oxidized anti-human IL-4 polyclonal antibody is mixed with 300 pmol of e-tag moiety-conjugated amino-dextran in the presence of 200 mM sodium carbonate, pH 9.5.
2. The solution was allowed to react for 2 hours at room temperature in the dark.
3. Sodium cyanoborohydride (made fresh in 1 N NaOH) is added to a final concentration of 50 mM and allowed to react for 30 minutes at room temperature.
4. Unreacted aldehydes are blocked by the addition of 50 mM ethanolamine, pH 9.6 and allowed to react for 30 minutes at room temperature.
5. The conjugate was purified by dialysis against 0.1×PBS (10 mM sodium phosphate, 15 mM NaCl, pH 7.2) for 20 hours at 4° C.

B. The Release of e-tag Reporters from Labeled Aminodextran

Figure 22:
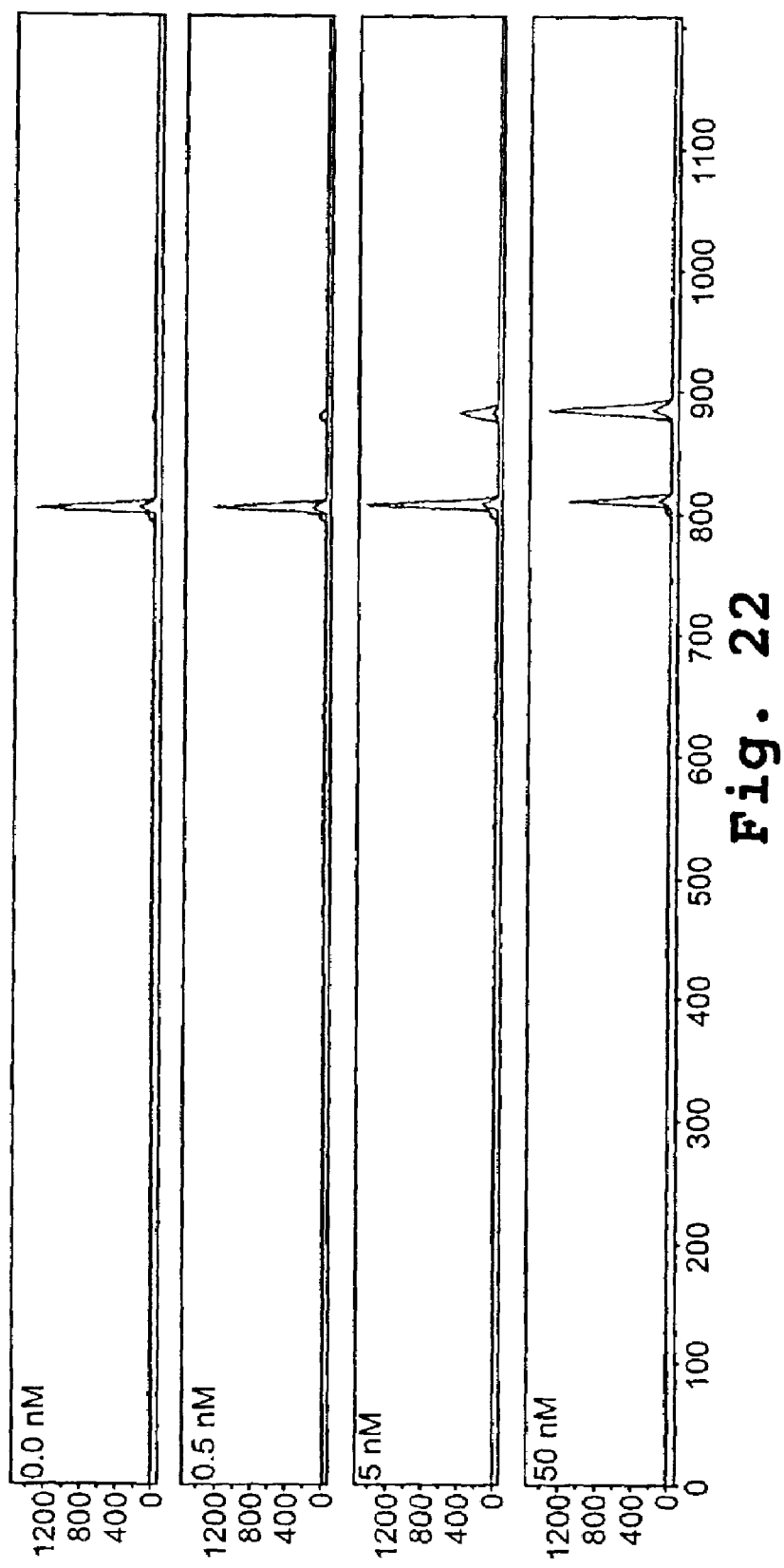
FIG. 22 shows a series of electropherograms demonstrating e-tag reporter (Pro8) analysis in an IFNγ titration study.

The procedure and device employed were substantially as discussed above for the SAMSA e-tag moiety. A total of 8 e-tag reporters were separated using ABI310. The separation conditions were as follows: 50 micron capillary, 47 cm long and 36 cm end-to-detection; separation buffer, POP-6 (PE Biosystems); injection 60 sec at 3.0 kV; separation voltage, 9.4 kV. The results are depicted in the electropherogram of FIG. 22.

C. Immunoassays with Antibodies Conjugated to e-tag Moieties.

Two types of immunoassays (direct and indirect or sandwich), developed from the conjugated e-tag moieties mentioned above, were carried out.

(C1) Sandwich Immunoassays for Cytokines.

Figure 23:
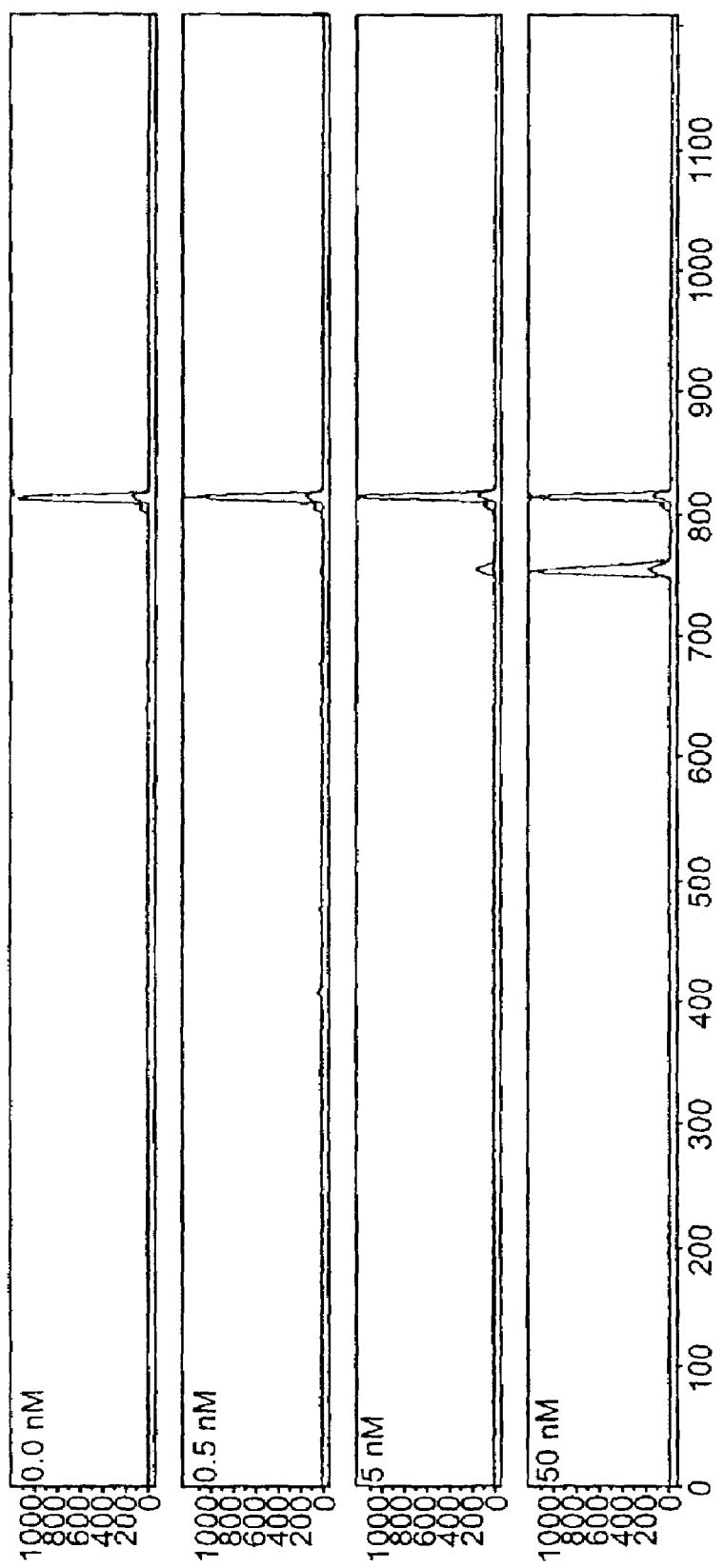
FIG. 23 shows a series of electropherograms demonstrating e-tag reporter (Pro7) analysis in an IFNα titration study.

A sandwich-type immunoassay was carried out (FIG. 23). The assay allows for the qualification and quantification of known cytokine antigens. In this assay, a matched pair of antibodies forms a sandwich around a cytokine antigen bringing the two antibodies in close proximity. One of these antibodies is conjugated with an e-tag moiety to yield an e-tag probe. The e-tag probes have a singlet oxygen labile linkage, which allows the release of the e-tag reporter after reaction with singlet oxygen. The second antibody is conjugated to a photosensitizer dye that produces singlet oxygen when irradiated at 680 nm. Due to the relatively short half-life of the singlet oxygen, only when the two antibodies form a sandwich does the singlet oxygen cleave the cleavable linkage of the e-tag probe.

Figure 24:
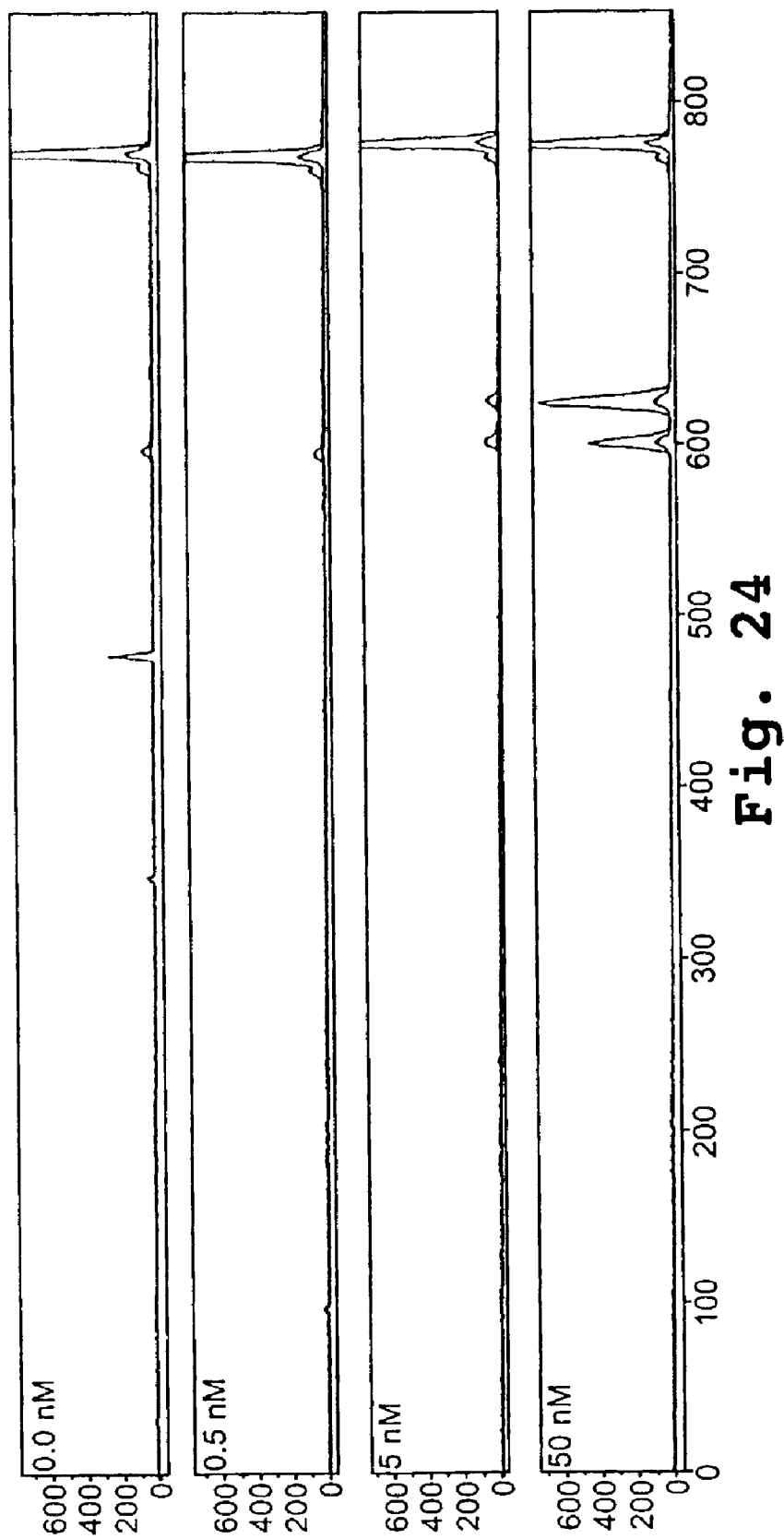
FIG. 24 shows a series of electropherograms demonstrating e-tag reporter (Pro4) analysis in an IL-10 titration study.

Protocol for a Sandwich Immunoassay for Cytokines 1. 10 µl of assay buffer (0.1×PBS, 40 mg/ml BSA) is mixed with 1 µl (100 nM) of biotin-labeled anti-human IL-4 monoclonal antibody (purchased from Pierce, catalogue number M-450-B) and 1 µl of cytokine IL-4 (Pierce, catalogue number R-IL-4–5) ranging in concentration from 0 to 500 nM.
2. The reaction was allowed to proceed for 30 minutes at room temperature.
3. 5 µl of 100 µg/ml streptavidin-labeled photosensitizer beads were added and the mixture was incubated for 15 minutes at room temperature in the dark.
4. To remove non-specific interactions of the e-tag probes with streptavidin, 2 µl of 5 µM biotin-DNP was added and incubated for 10 minutes at room temperature in the dark.
5. 1 µl of 400 nM anti-human IL-4 polyclonal antibody conjugated to an amino-dextran e-tag moiety was added and incubated for 30 minutes at room temperature in the dark.
6. The reaction mixture was then irradiated for 30s using a 150 watt lamp source with a optical filter of 680 DF+20 nm.
7. 1 µl of ROX T8 standard, 1:20 (from PE Biosystems), is then added and released e-tags were separated by capillary electrophoresis either on ABI310 or ACLARA plastic LabCard (ACLARA BioSciences, Inc. Mountain View, Calif.).
8. Separation conditions of the released e-tag reporters on ABI310 were as follows: 50 µm capillary, 47 cm long and 36 cm end-to-detection; separation buffer, POP-6; injection 60 s at 3.0 kV; separation Voltage, 9.4 kV. The results for IL-4 with the e-tag reporter Pro 1 are shown in FIG. 24.

Figure 25:
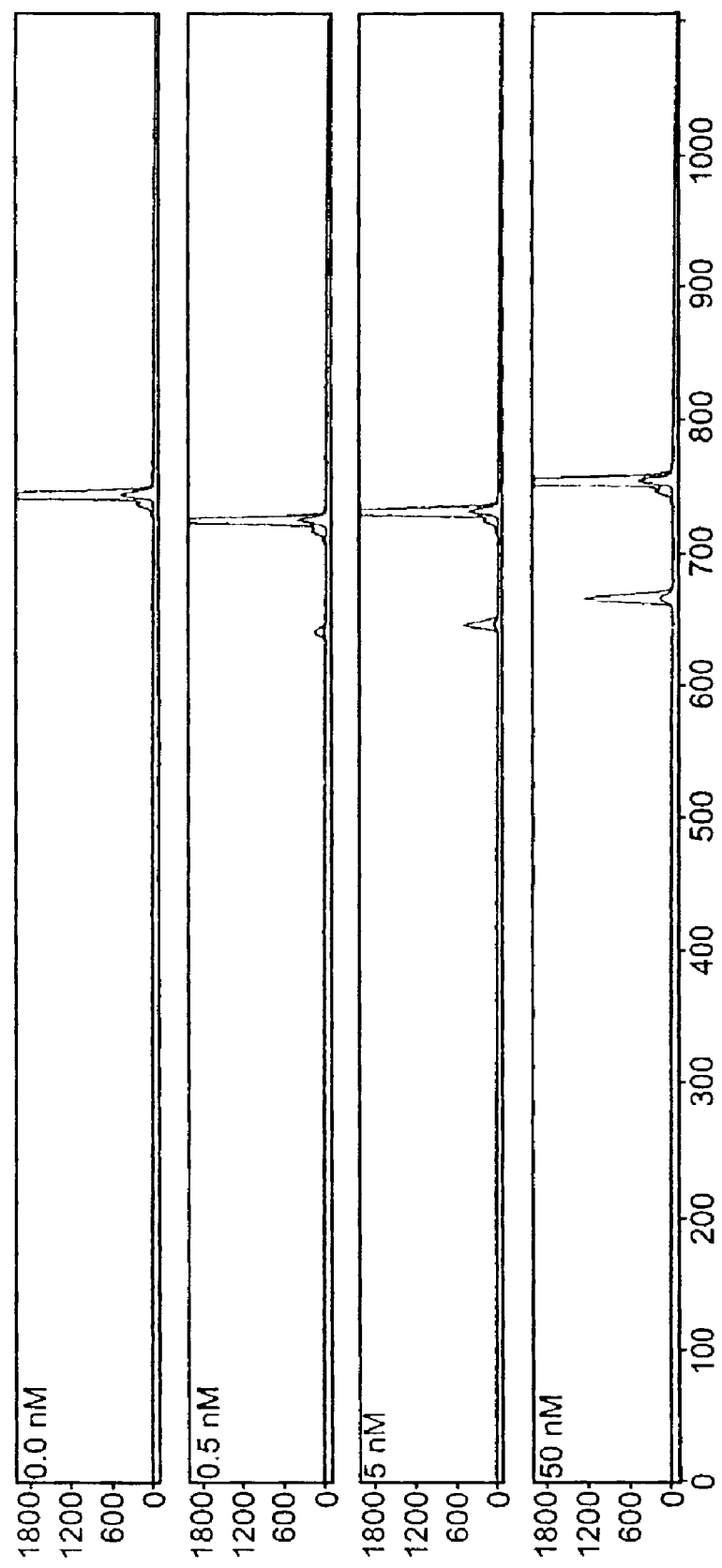
FIG. 25 shows a series of electropherograms demonstrating e-tag reporter (Pro2) analysis in an IL-8 titration study.
Figure 26:
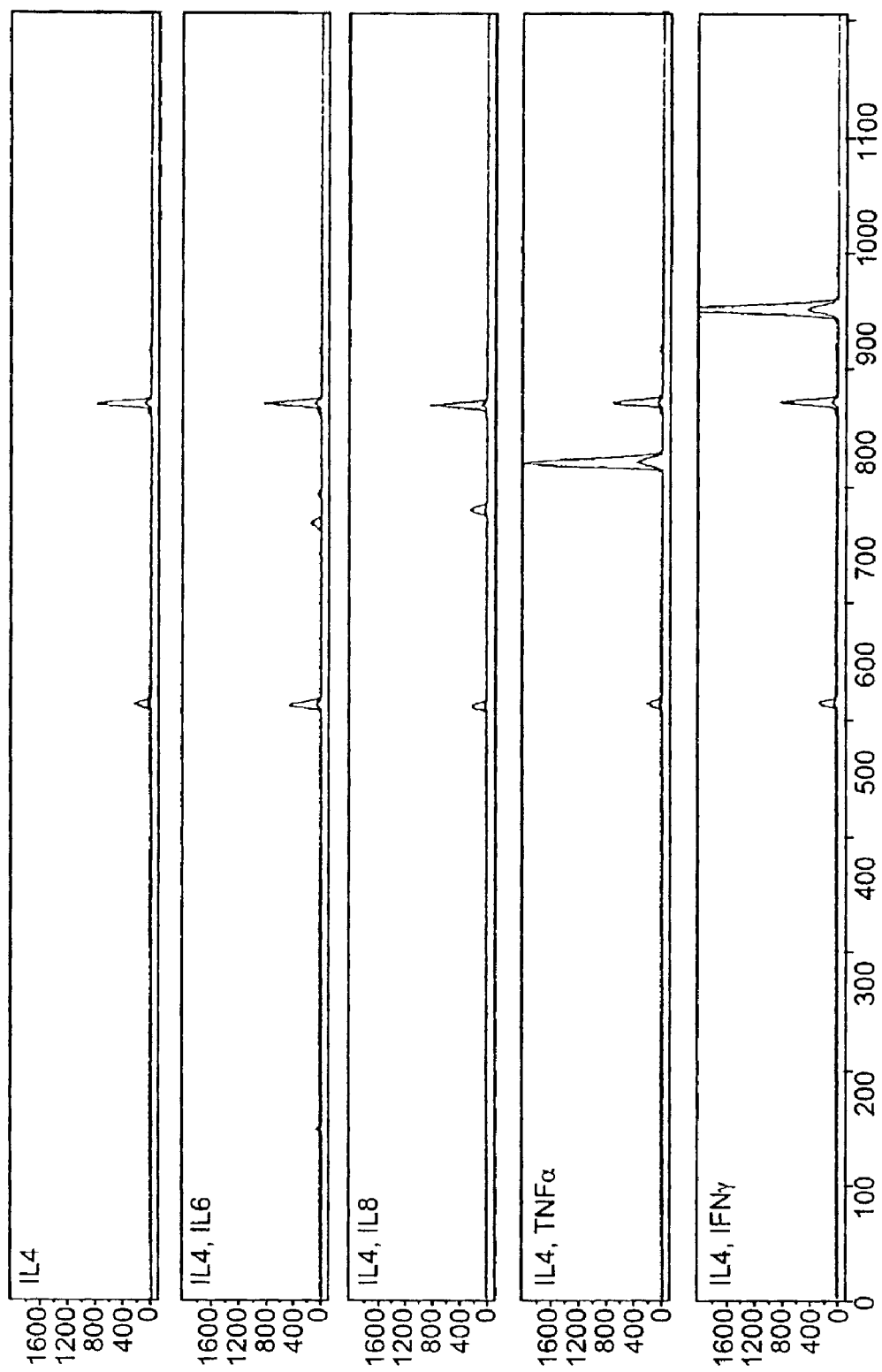
FIG. 26 depicts electropherograms demonstrating e-tag reporter analysis in singleplex and duplex cytokines studies.
Figure 27:
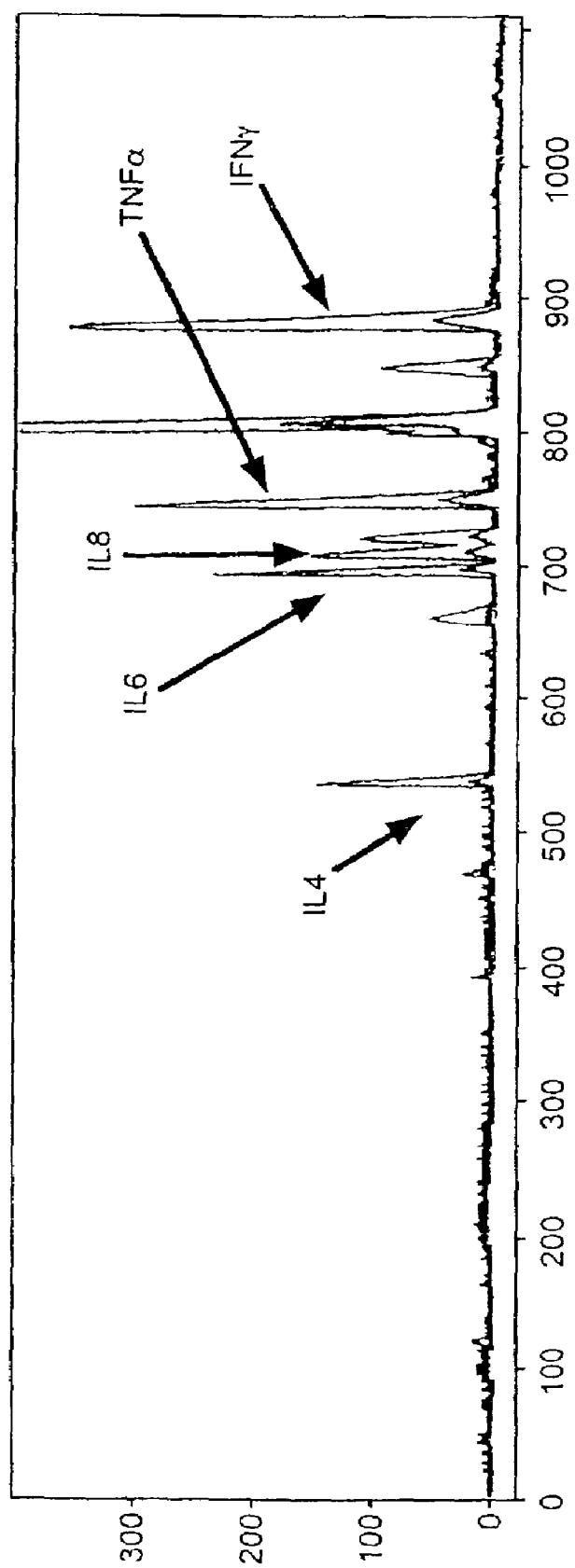
FIG. 27 depicts an electropherogram demonstrating e-tag reporter analysis in a multiplexed study of five cytokines.
Figure 28:
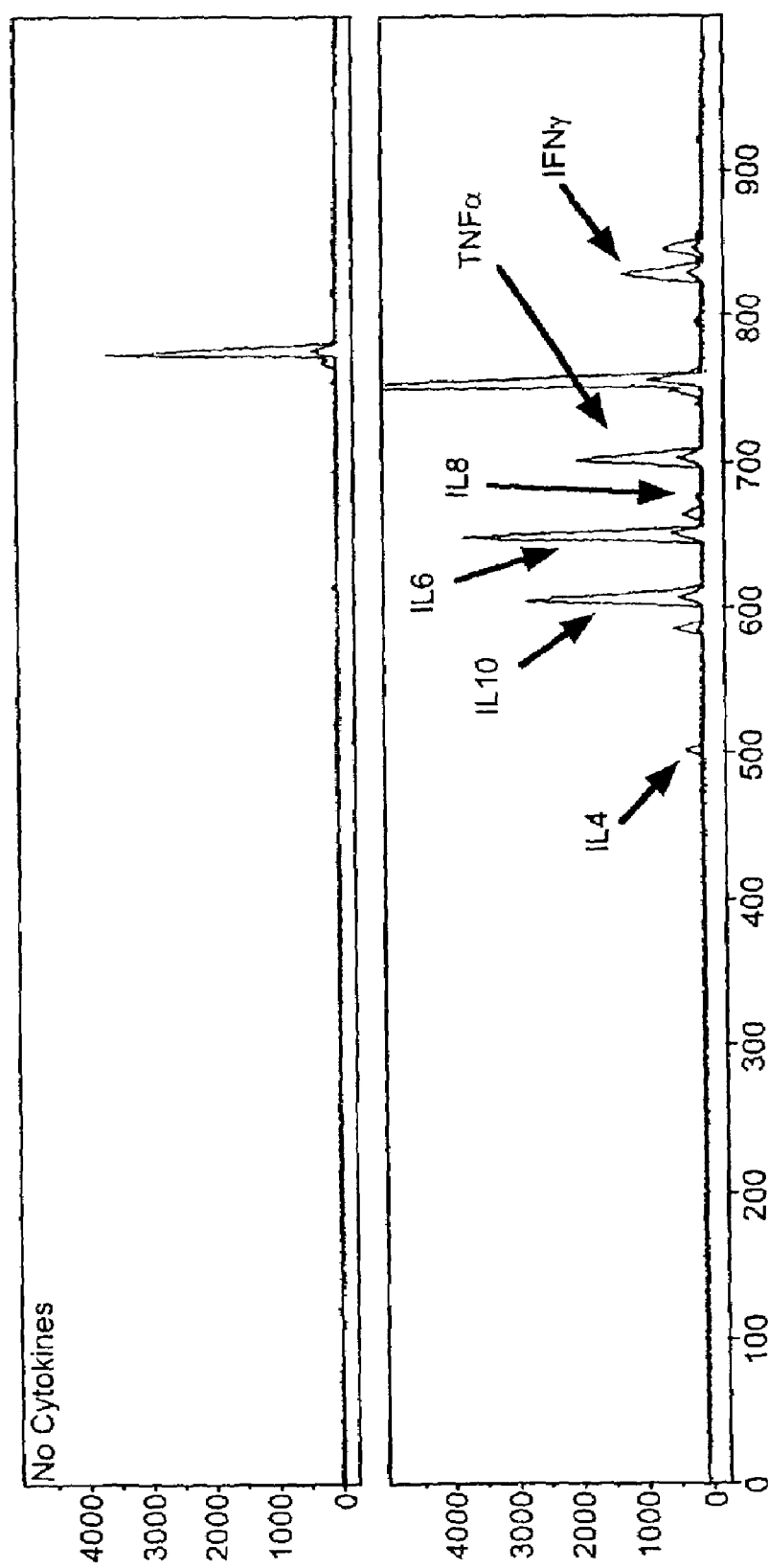
FIG. 28 depicts electropherograms demonstrating e-tag reporter analysis in a multiplexed cytokines study.
Figure 29:
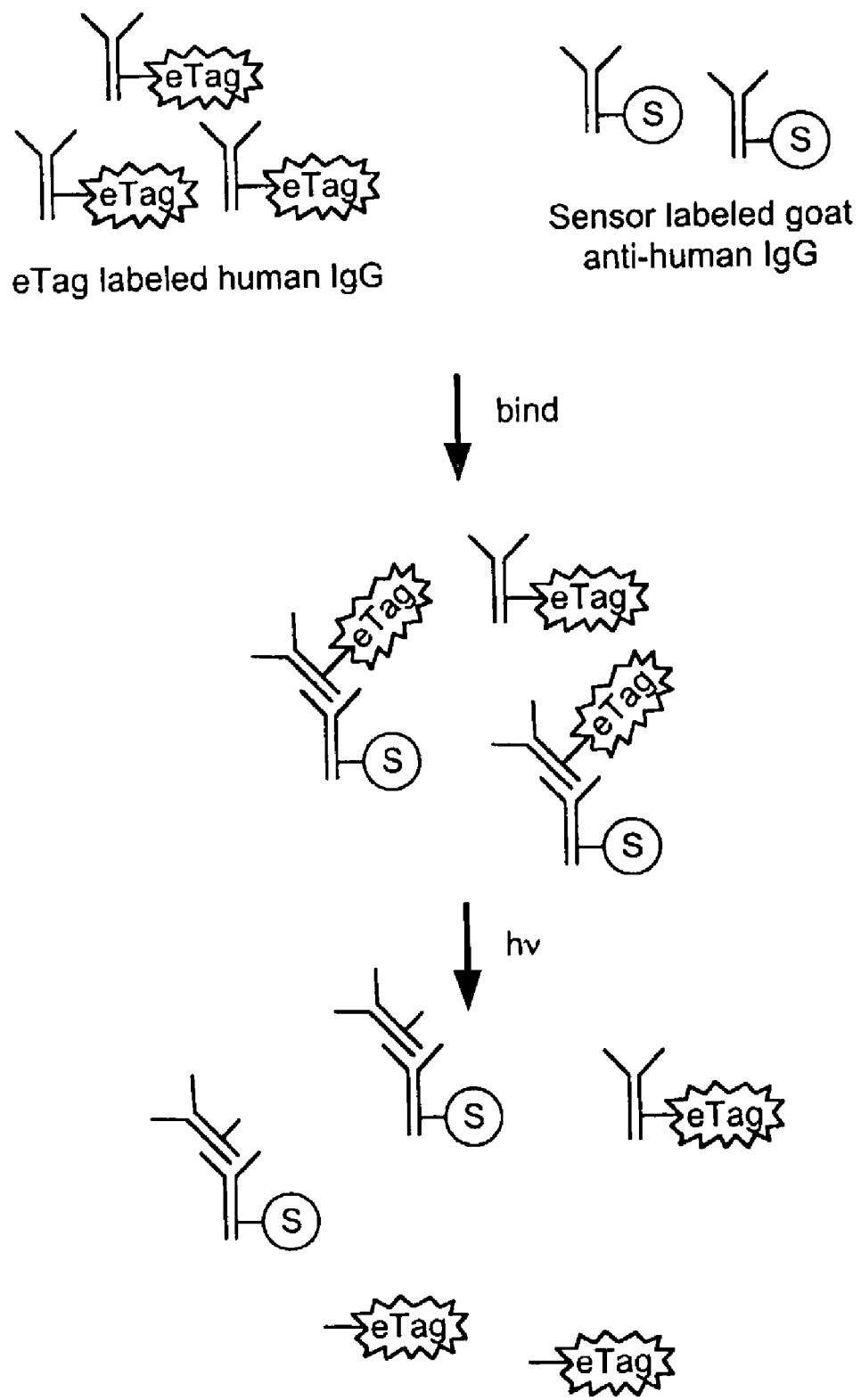
FIG. 29 is a cartoon depicting a homogeneous assay for the direct quantification of human IgG.

The above procedure was repeated for various cytokines and various e-tag moieties as follows: IL-6 was studied using e-tag moiety Pro 10 and the results are depicted in FIG. 25. IFNγ was studied using e-tag moiety Pro 8 and the results are depicted in FIG. 26. TNFα was studied using e-tag moiety Pro 7 and the results are depicted in FIG. 27. IL-10 was studied using e-tag moiety Pro 4 and the results are depicted in FIG. 28. IL-8 was studied using e-tag moiety Pro 2 and the results are depicted in FIG. 29.

Figure 30:
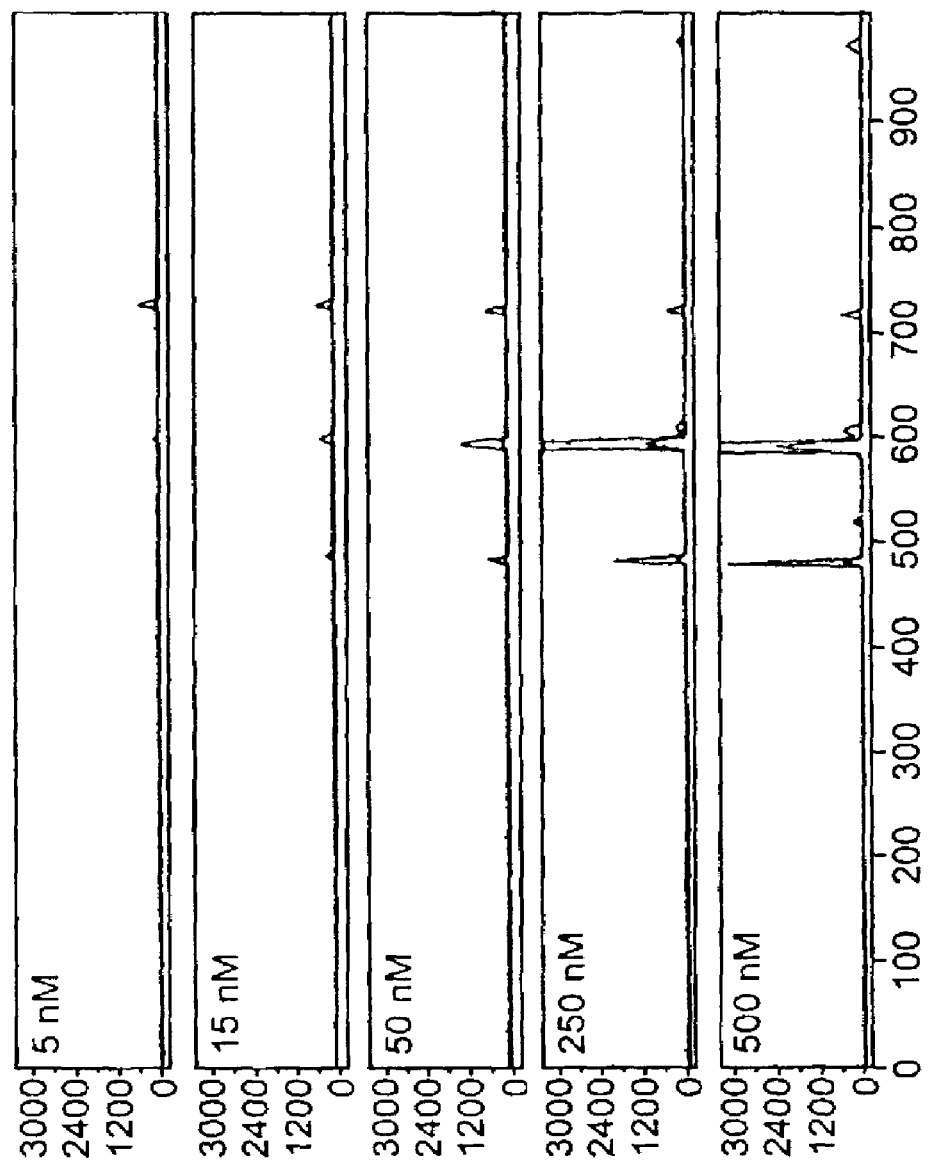
FIG. 30 depicts electropherograms demonstrating e-tag reporter analysis in a human IgG titration study.
Figure 31:
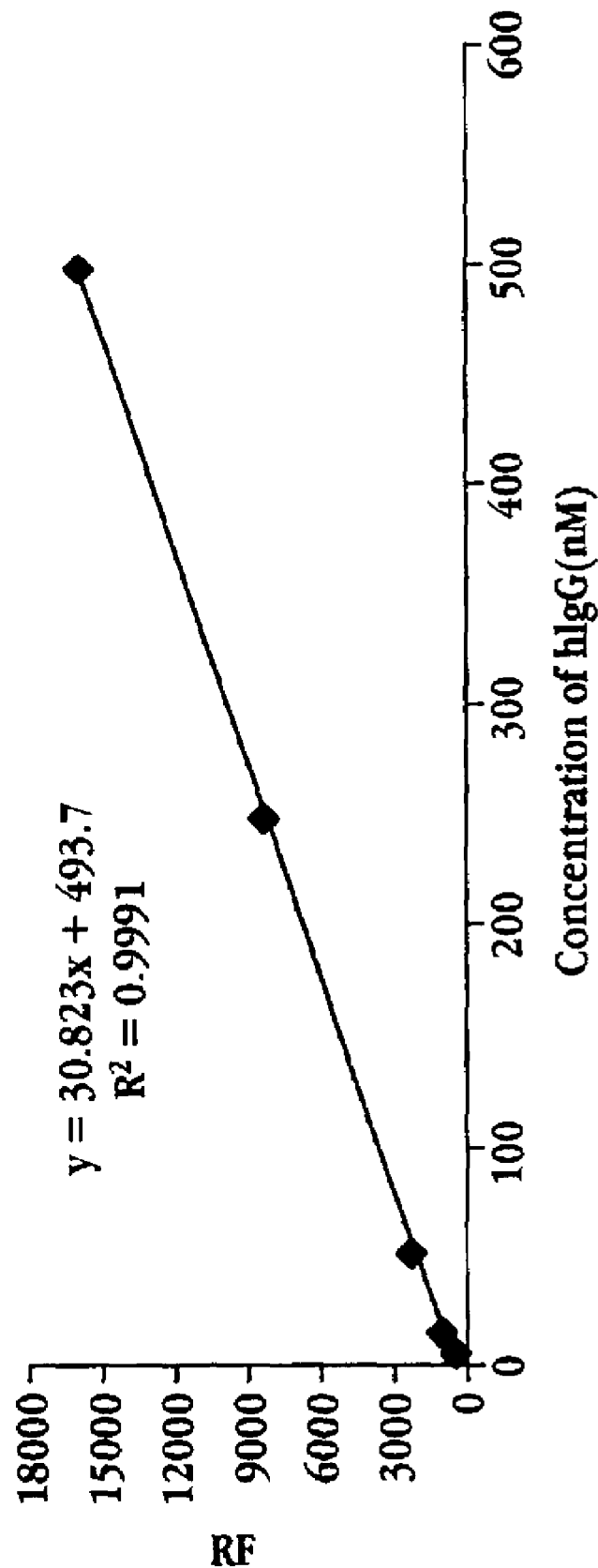
FIG. 31 depicts a calibration curve quantitating the results of FIG. 30.

IL-4 was studied as duplex reactions with other cytokines as follows: IL-4 and IL-6, IL-4 and IL-8, IL-4 and TNFα, and IL-4 and IFNγ. The results are depicted in FIG. 30. A multiplexed assay for five cytokines (IL-4, IL-6, IL-8, TNFα, and IFNγ) was carried out and the results are depicted in FIG. 31. A multiplexed assay for six cytokines (IL-4, IL-6, IL-8, IL-10, TNFα, and IFNγ) was conducted and the results are depicted in FIG. 32.

(C2) Direct Immunoassays for IgG.

In a direct immunoassay, the IgG antigen was conjugated with e-tag moieties to form e-tag probes. The e-tag probes have a singlet oxygen labile linkage, which allows the release of the e-tag reporter after reaction with singlet oxygen. The antibody is conjugated to a photosensitizer dye that produces singlet oxygen when irradiated at 680 nm. Due to the relatively short half-life of the singlet oxygen, only when the two antibodies bind does the singlet oxygen cleave the cleavable linkage to release an e-tag reporter (FIG. 33).

Protocol for Direct Immunoassay for Human IgG 1. 10 µl of assay buffer (0.1×PBS, 40 mg/ml BSA) is mixed with 1 µl (100 nM) of biotin-labeled anti-human IgG antibody and 1 µl of human IgG (from Sigma) labeled with an e-tag moiety ranging in concentration from 0 to 500 nM.
2. The reaction was allowed to react for 30 minutes at room temperature.
3. 5 µl of 100 µg/ml streptavidin-labeled photosensitizer beads were added and the mixture was incubated for 15 minutes at room temperature in the dark.
4. The reaction mixture was then irradiated for 30 sec using a 150 watt lamp source with a optical filter of 680 DF+20 nm.

5. 1 µl of ROX T8 standard is then added and released e-tag reporters are separated by capillary electrophoresis either on ABI310 or ACLARA plastic LabCard.

The results of various concentrations of human IgG are shown in FIG. 34. A calibration curve is depicted in FIG. 35.

It is evident from the results herein that the subject inventions provide powerful ways of preparing compositions for use in multiplexed determinations and methods for performing multiplexed determinations using such compositions. The methods provide for homogeneous and heterogeneous protocols, with proteins, as exemplary of other classes of compounds.

It is further evident from the above results that the subject invention provides an accurate, efficient and sensitive process, as well as compositions for use in the process, to perform multiplexed reactions. The protocols provide for great flexibility in the manner in which determinations are carried out and maybe applied to a wide variety of situations involving haptens, antigens, nucleic acids, cells, etc., where one may simultaneously perform a number of determinations on a single or plurality of samples and interrogate the samples for a plurality of events. The results of the determination are readily read in a simple manner using electrophoresis or mass spectrometry. Systems are provided where the entire process, after addition of the sample and reagents, may be performed under the control of a data processor with the results automatically recorded.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining the presence or absence of one or more target polypeptides in a sample suspected of containing the target polypeptides, the method comprising the steps of:
   a)—mixing the sample with a class-specific reagent and one or more electrophoretic probes, wherein the class-specific reagent comprises (i) a cleavage-inducing moiety having an effective proximity and (ii) an immobilized metal affinity chromatography (IMAC) resin that binds a phosphate group on the one or more target polypeptides, and wherein the one or more electrophoretic probes each comprises a binding moiety that specifically binds one of the target polypeptide(s) and one or more electrophoretic tags each attached thereto by a cleavable linkage, under conditions that permit the class-specific reagent and the one or more electrophoretic probes to bind to the one or more target polypeptides;
   b)—cleaving the cleavable linkage(s) of any of the one or more electrophoretic probes that are within the effective proximity of the cleavage-inducing moiety so that one or more electrophoretic tags are released; and
   c)—determining the presence or absence of the one or more target polypeptides based on the presence or absence of the released electrophoretic tag(s).

2. The method of claim 1 wherein said one or more target polypeptides is a plurality of target polypeptides.

3. The method of claim 2 wherein said cleavage-inducing moiety is a sensitizer that produces an active species.

4. The method of claim 3 wherein said sensitizer is a photosensitizer, said cleavable linkage is an oxidation-labile linkage, and said active species is selected from the group consisting of hydrogen peroxide, hydroxyl radical, superoxide anion, phenoxy radical, and singlet oxygen.

5. The method of claim 4 wherein said active species is singlet oxygen.

6. The method of claim 5 wherein said plurality of target polypeptides is in the range of from 2 to 100.

7. The method of claim 6 wherein said plurality of target polypeptides is in the range of from 5 to 50.

8. The method of claim 5 wherein said photosensitizer is selected from the group consisting of porphyrins, phthalocyanines, halogenated derivatives of a fluorescein dye, halogenated derivatives of a rhodamine dye, and naphthalocyanines.

9. The method of claim 5 wherein said cleavable linkage comprises an olefin, a thioether, a selenoether, a thiazole, an oxazole, or an imidazole.

10. The method of claim 5 wherein said electrophoretic probe is defined by the following formula: $T\text{-}(L\text{-}E)_k$ wherein:

T is a binding moiety specific for a target polypeptide, L is an oxidation-labile linkage, E is an electrophoretic tag, and k is an integer greater than or equal to 1.

11. The method of claim 10 wherein L is selected from the group consisting of olefins, thioethers, selenoethers, thiazoles, oxazoles, and imidazoles.

12. The method of claim 10 wherein E is a fluorescent, water-soluble organic compound having a molecular weight in the range of from about 150 to 2500 daltons.

13. The method of claim 10 wherein E has the form (M,D), wherein D is a fluorescent dye and wherein M is a mobility modifying moiety that is a bond or an organic molecule having up to 100 atoms other than hydrogen selected from the group consisting of carbon, oxygen, nitrogen, phosphorus, boron, and sulfur.

14. A kit for detecting the presence or absence of a plurality of target polypeptides in a sample, the kit comprising: a class-specific reagent comprising a cleavage-inducing moiety and an IMAC resin specific for a phosphate group on the one or more target polypeptides; and one or more electrophoretic probes each comprising a binding moiety specific for a target polypeptide and one of more electrophoretic tags attached by a cleavable linkage.

15. The kit of claim 14 wherein said cleavage-inducing moiety is a photosensitizer and said cleavable linkage is an oxidation-labile linkage.

16. The kit of claim 15 wherein said binding moieties of said one or more electrophoretic probes are antibody binding compositions.

17. The kit of claim 16 wherein said one or more electrophoretic probes are a plurality in the range of from 2 to 50.

18. The kit of claim 17 wherein each different electrophoretic probe is specific for a different target polypeptide.

19. The kit of claim 17 wherein each of said one or more electrophoretic probes is defined by the formula: $T\text{-}(L\text{-}E)_k$ wherein: T is said binding moiety specific for a target polypeptide, L is said oxidation-labile linkage, E is an electrophoretic tag, and k is an integer greater than or equal to 1.

20. The method of claim 3 wherein said sensitizer is a photosensitizer.

21. The method of claim 3 wherein said cleavable linkage is an oxidation-labile linkage.

22. The method of claim 3 wherein said active species is selected from the group consisting of hydrogen peroxide, hydroxyl radical, superoxide anion, phenoxy radical, and singlet oxygen.

* * * * *

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: metal binding peptide

<400> SEQUENCE: 1

Gly His His Pro His Gly
1               5

<210> SEQ ID NO 2
<211> LENGTH: 11
<212> TYPE: PRT
<213> ORGANISM: Artificial Sequence
<220> FEATURE:
<223> OTHER INFORMATION: metal binding peptide

<400> SEQUENCE: 2

Gly His His Pro His Gly His His Pro His Gly
1               5                   10

<210> SEQ ID NO 3
<211> LENGTH: 16
<212> TYPE: PRT
<213> ORGANISM: Artificial Sequence
<220> FEATURE:
<223> OTHER INFORMATION: metal binding peptide

<400> SEQUENCE: 3

Gly His His Pro His Gly His His Pro His Gly His His Pro His Gly
1               5                   10                  15

<210> SEQ ID NO 4
<211> LENGTH: 26
<212> TYPE: PRT
<213> ORGANISM: Artificial Sequence
<220> FEATURE:
<223> OTHER INFORMATION: metal binding peptide

<400> SEQUENCE: 4
```

```
Gly His His Pro His Gly His His Pro His Gly His His Pro His Gly
1               5                   10                  15

His His Pro His Gly His His Pro His Gly
            20                  25
```